United States Patent
Spitzer et al.

(10) Patent No.: US 6,636,185 B1
(45) Date of Patent: *Oct. 21, 2003

(54) HEAD-MOUNTED DISPLAY SYSTEM

(75) Inventors: Mark B. Spitzer, Sharon, MA (US);
Ronald Gale, Sharon, MA (US);
Jeffrey Jacobsen, Hollister, CA (US)

(73) Assignee: Kopin Corporation, Taunton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/703,271

(22) Filed: Oct. 31, 2000

Related U.S. Application Data

(63) Continuation of application No. 08/295,826, filed as application No. PCT/US93/02312 on Mar. 12, 1993, now Pat. No. 6,140,980, and a continuation-in-part of application No. PCT/US93/01322, filed on Feb. 12, 1993, and a continuation-in-part of application No. 07/985,285, filed on Dec. 4, 1992, now Pat. No. 5,331,149, and a continuation-in-part of application No. 07/971,352, filed on Nov. 4, 1992, now abandoned, and a continuation-in-part of application No. 07/874,588, filed on Apr. 24, 1992, now Pat. No. 5,376,561, and a continuation-in-part of application No. 07/851,178, filed on Mar. 13, 1992, now abandoned.

(51) Int. Cl.⁷ .................................. G09G 1/06
(52) U.S. Cl. .......................... 345/8; 359/630
(58) Field of Search .................. 345/6–8; 359/54, 359/55, 59, 630; 351/201, 212; 396/51

(56) References Cited

U.S. PATENT DOCUMENTS

| | | | |
|---|---|---|---|
| 3,375,375 A | 3/1968 | Abbey et al. | 250/216 |
| 3,923,370 A | 12/1975 | Mustram | 359/630 |
| 3,967,253 A | 6/1976 | Tsuruishi | 340/173 |

(List continued on next page.)

FOREIGN PATENT DOCUMENTS

| | | |
|---|---|---|
| DE | 2 715 446 | 10/1978 |
| EP | 0 344 881 A2 | 12/1989 |
| EP | 0 408 344 A3 | 1/1991 |
| EP | 0 474 474 A2 | 3/1992 |
| EP | 0 486 318 A1 | 5/1992 |
| EP | 0 539 907 A2 | 5/1993 |
| FR | 2 522 804 | 9/1983 |
| FR | 2 612 351 | 9/1988 |
| JP | 54-93378 | 7/1979 |
| JP | 60-46019 | 3/1985 |
| JP | 1-259580 | 10/1989 |
| WO | 91/04508 | 4/1991 |
| WO | WO 92/16075 | 9/1992 |

OTHER PUBLICATIONS

Handschy, M., et al., "Ferroelectric Liquid–Crystal Devices for High–Resolution Imaging" *SID International Symposium Digest of Technical Papers,* Anaheim, May 6–10, 1991, No. vol. 22, pp 246–249.

Sumiyoshi, K., et al., "Device Layer Transferred Poly–S1 TFT Array for High Resolution Liquid Crystal Projector", *Proceedings of the International Electron Devices Meeting,* Washington, Dec. 3–6, 1989, pp. 165–168.

Spangler, L., et al., "A Technology for High–Performance Single–Crystal Silicon–on–Insulator Transistors", *IEEE Electron Device Letters,* vol. EDL–08, No. 4, Apr. 1, 1987, pp. 137–139.

Katz, Warren, "Low Cost Helmet Mounted Display and Eye Tracking Concepts," Mak Technologies, Inc. (1991).

Dutta, et al., A Novel Binarily Detectable High–Speed Optical Position–Sensitive Device (BPSD), *Journal of Lightwave Technology,* 10(3) :391–395 (1992).

Matsuda, Tetsuro, "The LCD Challenge to Cathode Ray Tubes," *JEE,* pp. 57–58, 60–61 (1988).

Ahrenkiel, et al., "Minority–Carrier Lifetime in GaAs Thin Films," *Apl. Phys. Lett* 55 (7) :598–599 (1988).

*Primary Examiner*—Amare Mengistu
(74) *Attorney, Agent, or Firm*—Hamilton, Brook, Smith & Reynolds, P.C.

(57) ABSTRACT

A head mounted display system including a high resolution active matrix display which reduces center of gravity offset in a compact design. The active matrix display can be either a liquid crystal display or a light emitting display.

30 Claims, 35 Drawing Sheets

U.S. PATENT DOCUMENTS

| | | | | |
|---|---|---|---|---|
| 4,028,725 A | 6/1977 | Lewis | | 358/103 |
| 4,034,401 A | 7/1977 | Mann | | 358/93 |
| 4,109,145 A | 8/1978 | Graf | | 250/201 |
| 4,181,405 A | 1/1980 | Cohen | | 350/174 |
| 4,287,809 A | 9/1981 | Egli et al. | | 89/41 |
| 4,361,384 A | 11/1982 | Bosserman | | 350/174 |
| 4,568,159 A | 2/1986 | Baldwin | | 351/209 |
| 4,636,866 A | 1/1987 | Hattori | | 358/236 |
| 4,852,988 A | 8/1989 | Velez et al. | | 351/210 |
| 4,884,219 A | 11/1989 | Waldren | | 364/514 |
| 4,933,755 A | 6/1990 | Dahl et al. | | |
| 4,962,998 A | 10/1990 | Iino | | 345/7 |
| 5,093,567 A | 3/1992 | Stavely | | 250/221 |
| 5,206,749 A | 4/1993 | Zavracky et al. | | 359/59 |
| 5,258,325 A | 11/1993 | Spitzer et al. | | 437/86 |
| 5,300,788 A | 4/1994 | Fan et al. | | 257/13 |
| 5,317,236 A | 5/1994 | Zavracky et al. | | 315/169.3 |
| 5,331,149 A | * 7/1994 | Spitzer et al. | | 250/221 |
| 5,583,335 A | 12/1996 | Spitzer et al. | | 250/221 |
| 5,825,456 A | * 10/1998 | Tabata et al. | | 351/201 |
| 5,873,003 A | * 2/1999 | Inoue et al. | | 396/51 |
| 6,140,980 A | * 10/2000 | Spitzer et al. | | 345/8 |
| 6,206,523 B1 | * 3/2001 | Hino | | 351/212 |
| 6,315,413 B1 | * 11/2001 | Shimmick et al. | | 351/212 |
| 6,366,388 B1 | * 4/2002 | Hampp | | 359/241 |
| 6,369,953 B2 | * 4/2002 | Melville et al. | | 359/630 |
| 6,409,345 B1 | * 6/2002 | Molebny et al. | | 351/121 |

* cited by examiner

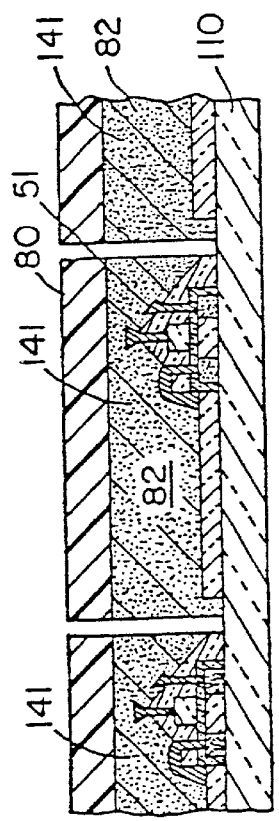
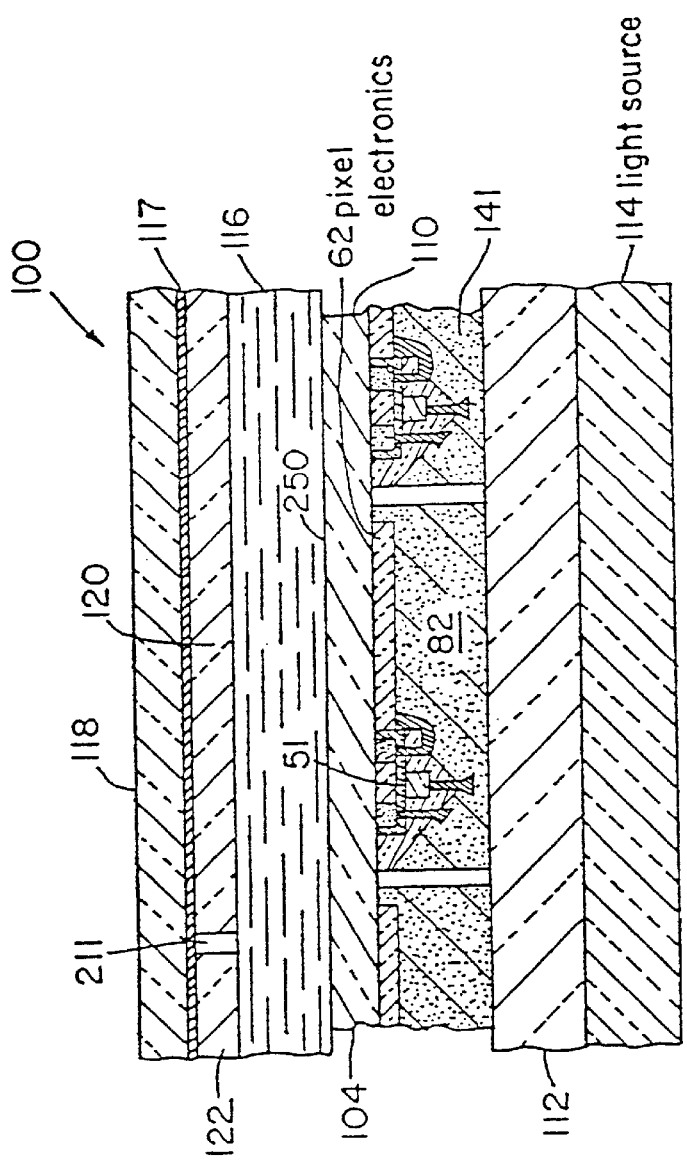
FIG. 5A
FIG. 5B

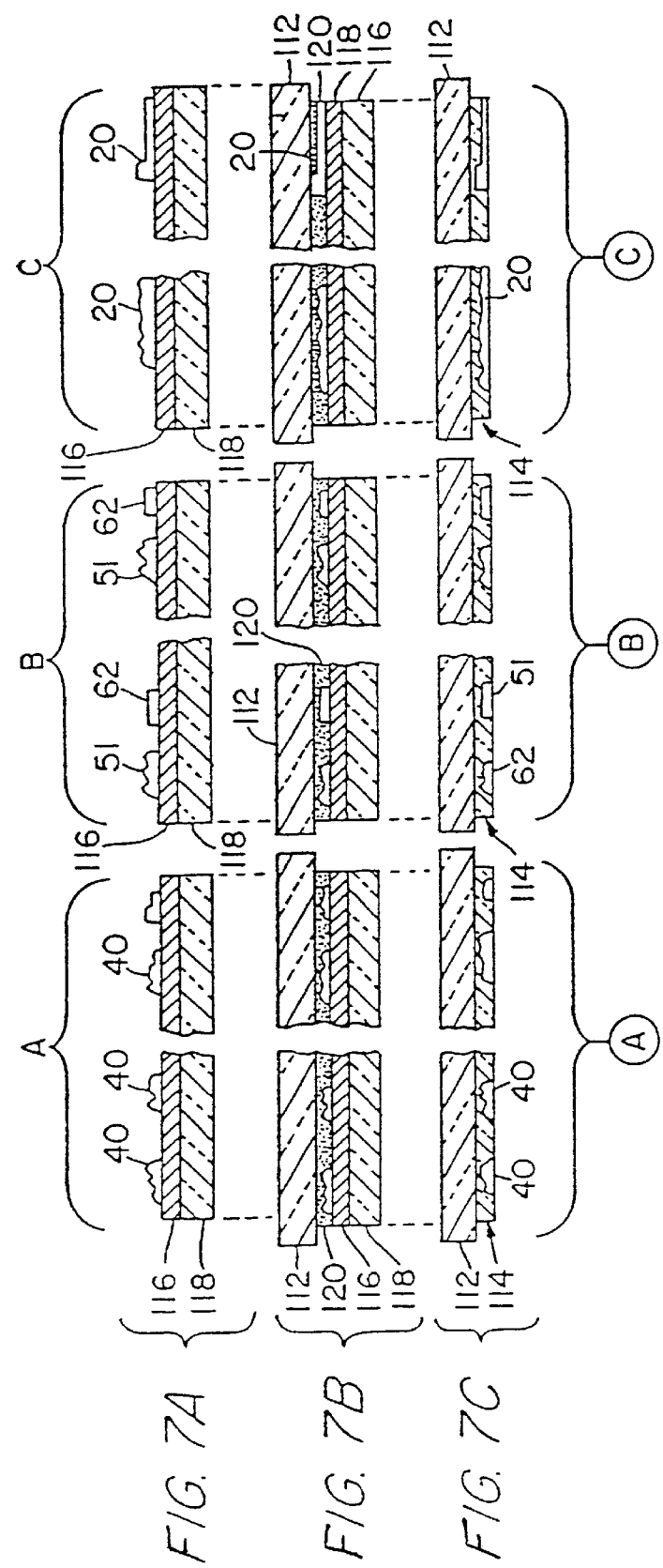

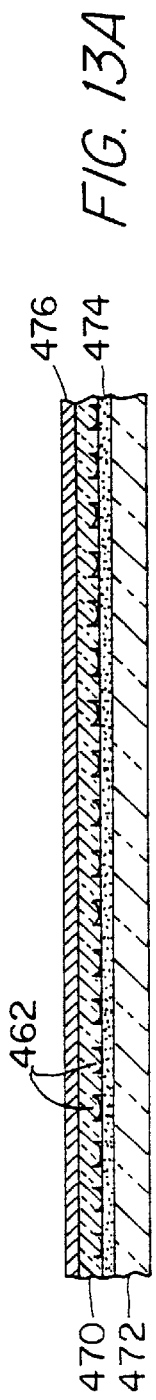
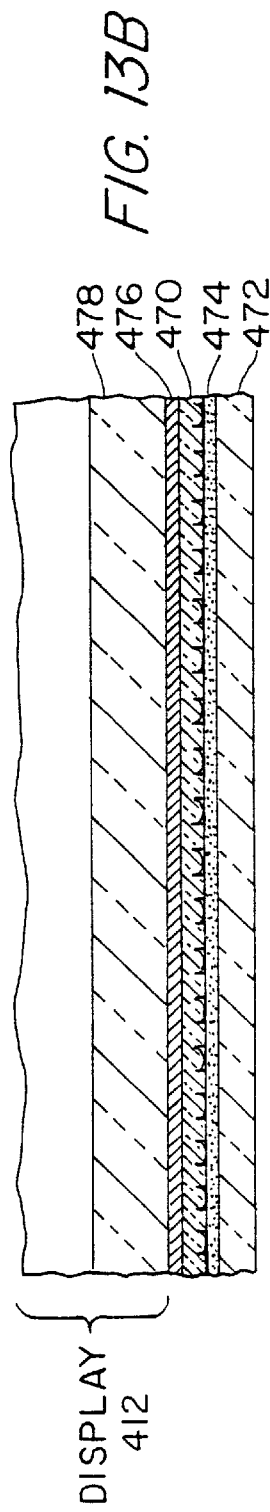
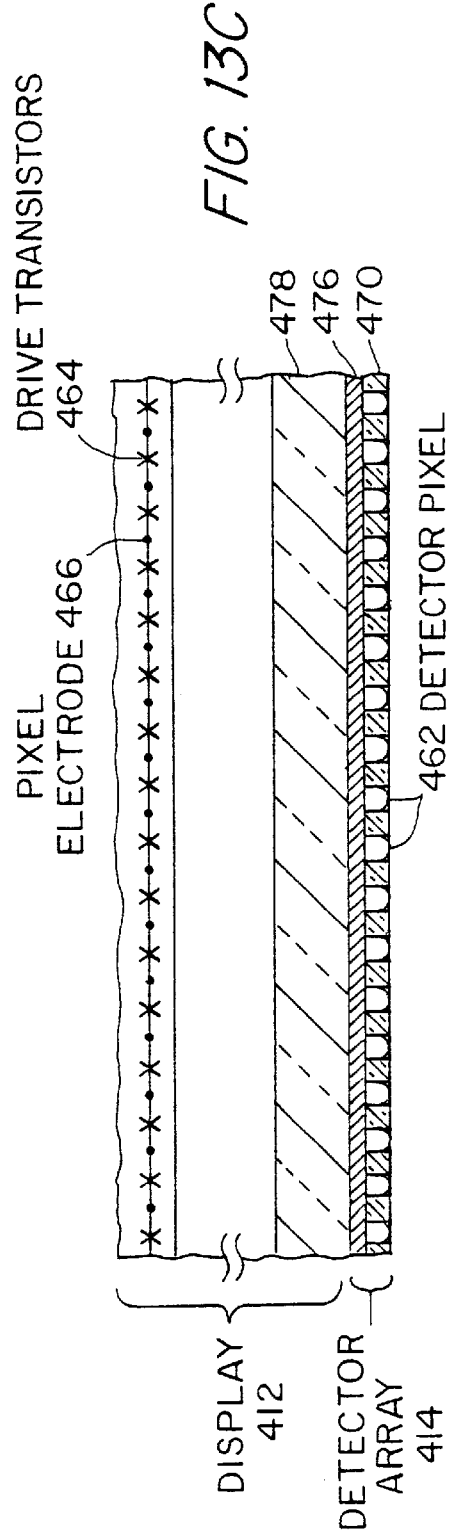
FIG. 13A
FIG. 13B
FIG. 13C

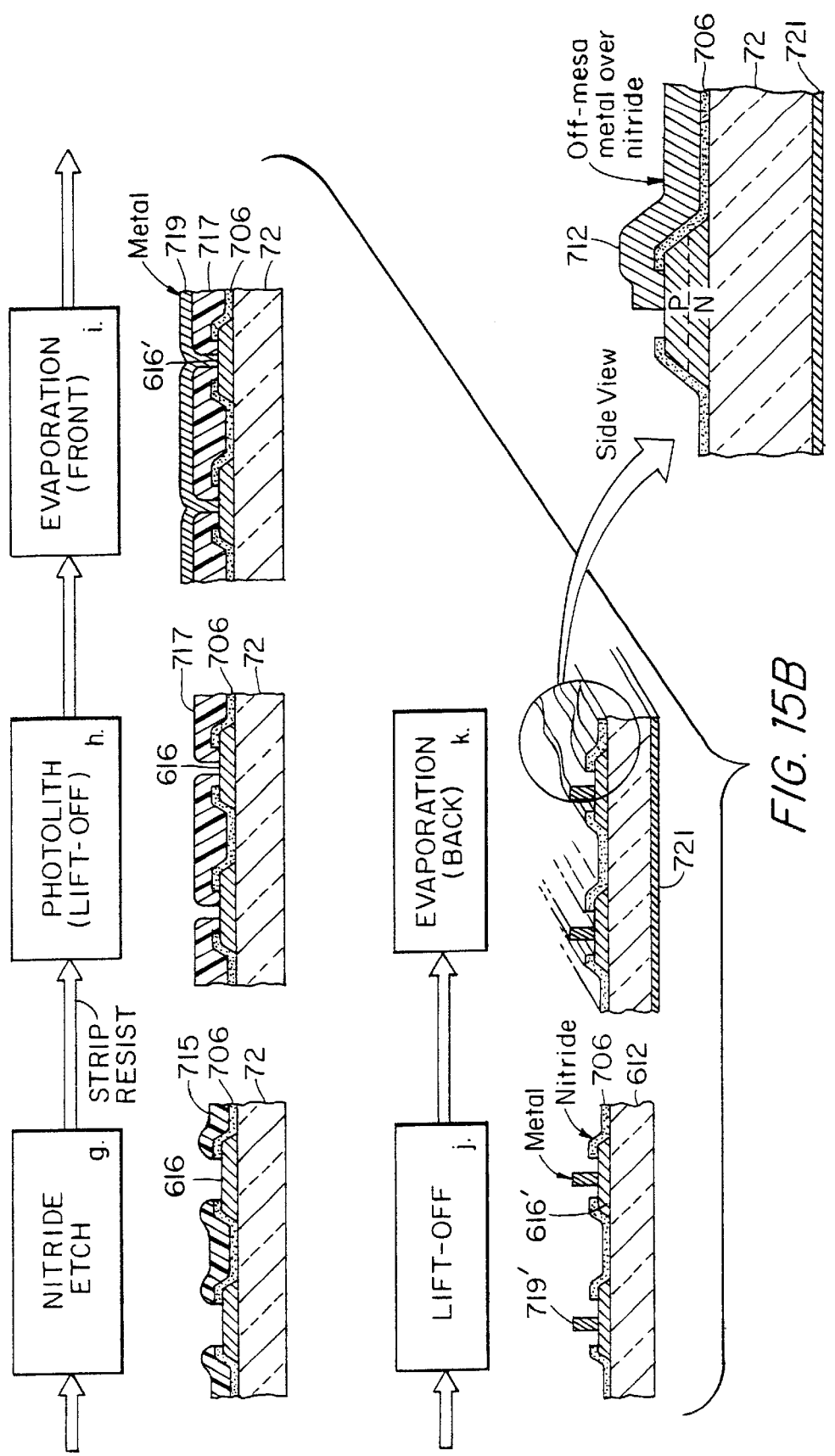

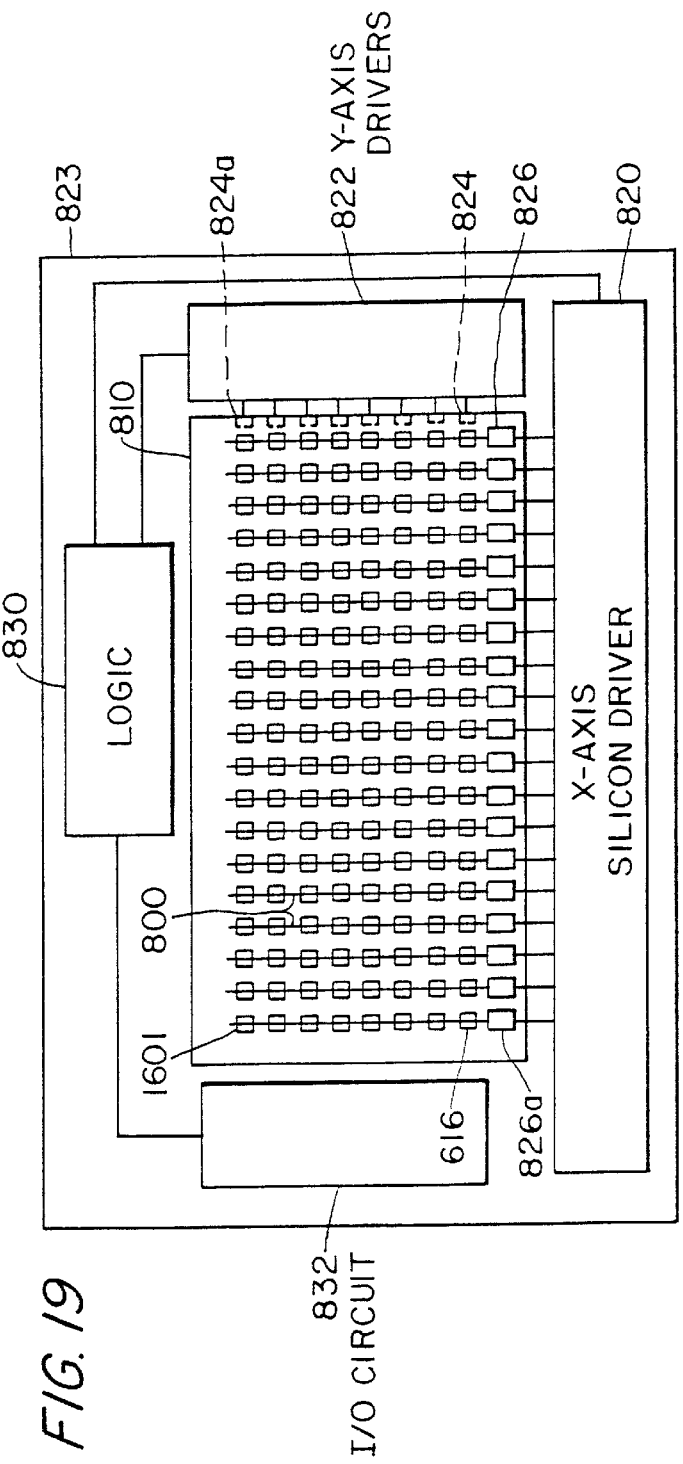
FIG. 19
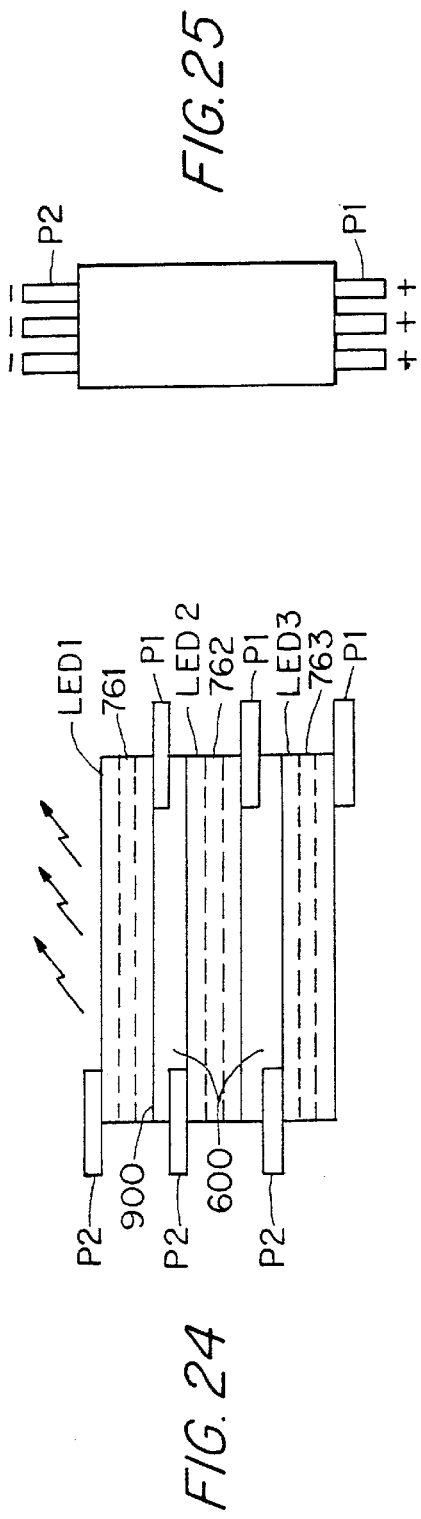
FIG. 25
FIG. 24

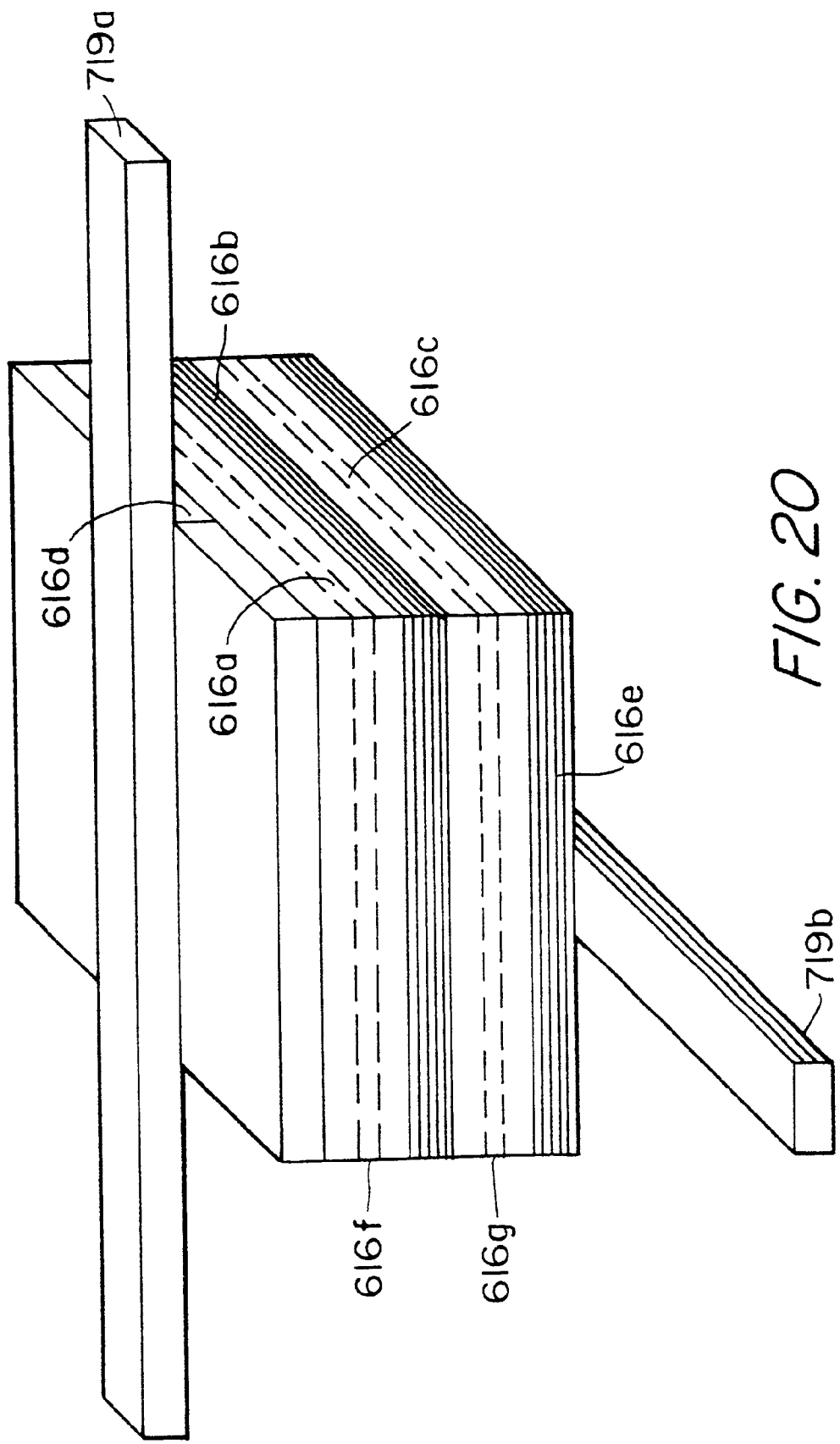

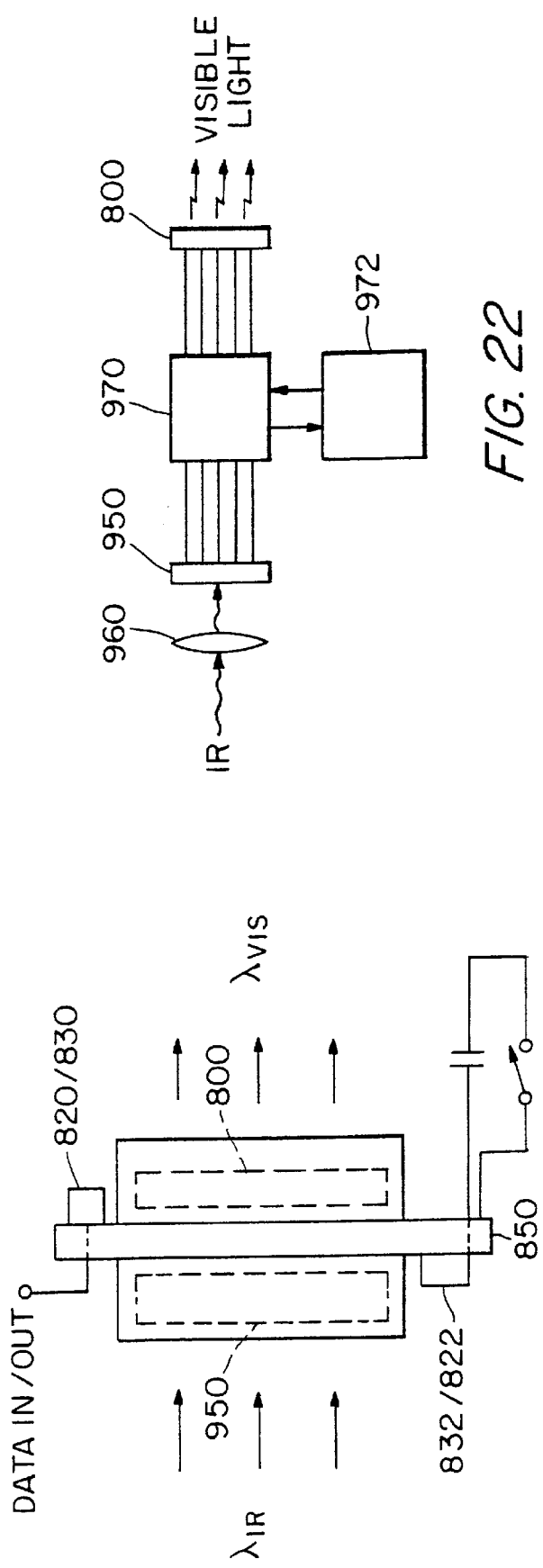
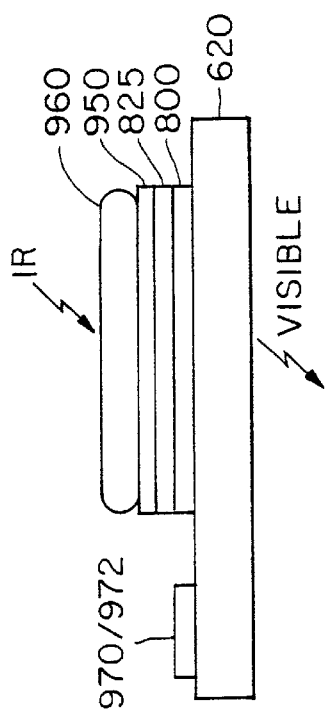
FIG. 22
FIG. 23
FIG. 21

HEAD-MOUNTED DISPLAY SYSTEM

RELATED APPLICATIONS

This is a continuation of U.S. application Ser. No. 08/295,826, filed on Feb. 2, 1995, (now U.S. Pat. No. 6,140,980, issued Oct. 31, 2000) which is a U.S. National Phase Application of PCT/US93/02312, filed Mar. 12, 1993 and is continuation-in-part of U.S. application Ser. No. 07/851,178, filed Mar. 13, 1992 (abandoned) and is a continuation-in-part of U.S. application Ser. No. 07/874,588, filed Apr. 24, 1992 (now U.S. Pat. No. 5,376,561) and is a continuation-in-part of U.S. application Ser. No. 07/971,352, filed Nov. 4, 1992 (abandoned) and is a continuation-in-part of U.S. application Ser. No. 07/985,285, filed Dec. 4, 1992 (now U.S. Pat. No. 5,331,149) and is a continuation-in-part of International Application No. PCT/US93/01322, filed Feb. 12, 1993.

BACKGROUND OF THE INVENTION

Head mounted display systems have been developed for a number of different applications including use by aircraft pilots and for simulation. Head mounted displays are generally limited by their resolution and by their size and weight. Existing displays have relatively low resolution and are positioned at a relatively large distance from the eye. Of particular importance, is to keep the center of gravity of the display from extending upward and forward from the center of gravity of the head and neck of the wearer, where it will place a large torque on the wearer's neck and may bump into other instruments during use. There is a continuing need to present images to the wearer of a helmet mounted display in a high-resolution format similar to that of a computer monitor. The display needs to be as non-intrusive as possible, leading to the need for a lightweight and compact system.

Head mounted displays can also utilize eye tracking systems in flight control, flight simulation and virtual imaging displays. Eye control systems generate information based on the position of the eye with respect to an image on a display. This information is useful for a variety of applications. It can be used to enable the viewer to control "hands-free" movement of a cursor, such as a cross-hair on the display.

Apparatus for detecting the orientation of the eye or determining its line-of-sight (LOS) are called occulometers or eye trackers and are well known in the art. (See for example U.S. Pat. Nos. 4,109,145, 4,034,401 and 4,028,725).

SUMMARY OF THE INVENTION

In accordance with the present invention a head mounted display is preferably either an electroluminescent (EL) or an active matrix liquid crystal display (AMLCD) comprising thin film transistor (TFT) driving elements formed of single crystal silicon and then transferred to a transparent glass substrate. Each TFT circuit is connected to an electrode which defines a picture element (pixel) of the display. The head mounted display system can also include a detector array comprising thin film integrated optical diode detectors is formed of III–V materials and transferred directly onto a flat panel active matrix display.

In a preferred embodiment of a direct view eye tracking dispaly, the detectors are positioned such that each is completely above the drive transistors of the active matrix circuit i.e., adjacent to the pixel area and therefore do not block any of the display's light output. The light output from the display, either infrared or visible, is used to determine the position of the eye. No additional optics, such as, fiber optics to/from remote displays are required in this approach. The chief advantage is that the integrated eyetracker/display can be inserted in a helmet-mounted optical system without physical modification to the helmet or optics. This advantage results from the fundamental reciprocity of the axial light rays that are used to determine the eye position. An axial ray, is a light ray that emanates from the display and travels through the optical axis of the eye, normal to the retina. These rays, when reflected by the retina, can travel back to the display along the same optical path (in accordance with the optical reciprocity theorem). Except for divergence of the rays, the reflected rays return to the vicinity of the emitting pixel. In this way, the detector can identify the area of the display that is sighted by the user. Software in a computer then provides a cursor at this location.

In another alternative embodiment, instead of using the visible scene from the display, some of the frames in the display are used for brief presentation of an interlaced eyetracker pattern. If the repetition rate of the test pattern is sufficiently infrequent, the user (viewer) will not perceive its presence. This pattern can consist of a single pixel being illuminated or can have some other geometric pattern. Light from a single lit pixel enters the eye through the pupil and is reflected from the retina. The path of the reflected light clearly depends on the position of the eye. On the reverse path back to the display panel, the reflected light undergoes spreading or convergence depending upon the optical system. As it returns to the plane of the display, it strikes the photodetectors. A pattern will appear in the output of the photodetector array that depends on the position of the eye and the nature of the optical system. This pattern is interpreted by a computer and correlated to the position of the eye.

The present invention uses a single-crystal material to produce a high-density active matrix array in a head mounted optical support system that provides for closeness of the display to the eye, compactness of the array and provides the desired level of resolution. With a density of 400 lines per centimeter, for example, a 1.27 centimeters display in accordance with the invention will fit into a system only 1.52 centimeters in depth. This system is more compact, has lighter weight, and a lower cost than existing head mounted displays.

To get the display system as close as possible to the eye and as compact as possible, a short focal length lens system must be used. The focal lengths of simple lenses are limited by lens geometry, where the thickness of the lens is less than the lens diameter. Thus, a simple lens has a shorter focal length as well as a small diameter. For the most compact system, the smallest possible lens that focuses the display image is used. The lens size is defined by the object size, which in this case is the size of the display element.

Since resolution needs to be increased while size needs to be decreased, the pixel density of the display needs to increase. Existing displays have pixel densities of about 120 lines per centimeter and are about 4.1 centimeters in diameter. Using a 3.81 centimeter lens, where the minimum focal length for a standard 3.81 centimeter lens is about 3.05 centimeters, results in a lens with a center thickness of over 1.52 centimeters. The use of this lens results in a lens-to-display distance of about 3.3 centimeters, which is the minimum depth of an existing head-mounted display for this geometry.

The present system, by increasing the pixel density to at least 200 lines per centimeter, and preferably to over 400 lines per centimeter, provides for a lens-to-display distance of less than one inch.

The lens-to-display distance is preferably in the range of 1.0–2.2 centimeters.

The display can be a transmission type display with the light source directly adjacent the light valve active matrix or the light source can be positioned above the head or to one or both sides of the head of the user such that the light can be coupled to the light valve active matrix by one or more reflective elements. Fiber optics can also be employed to provide a back light source for the display or to deliver images from the display into the user's field of view.

Alternatively, the display can be an emission type device such as an active matrix electroluminescent display or an active matrix of light emitting diodes (LEDs).

Additional embodiments of the invention include a projected view active matrix display in which different polarization components of light are separated, one component being directed to the left eye, and another component being directed to the right eye. This provides a more efficient optical system in which more light from the source is used to provide the desired image.

Another preferred embodiment utilizes an active matrix display in which the pixel size increases across the display to provide a wide angle field of view display.

The display can be fabricated as a visor with a number of displays which are tiled together and positioned on a flat or curved plastic visor.

BRIEF DESCRIPTION OF THE DRAWINGS

FIGS. 5A and 5B are cross-sectional schematic process views of a portion of the AMLCD.

FIGS. 7A–7D is a process flow sequence illustrating transfer and bonding of a silicon an oxide (SOI) structure to a glass superstrate and removal of the substrate.

FIGS. 13A–13C are cross-sectioned views showing important steps in the process of forming the eye-tracker device of the invention.

FIGS. 15A–15B is a process flow diagram of the main steps in fabricating an LED bar in accordance with a mesa etch isolation process with a corresponding schematic sectional view of a wafer structure so processed shown beneath each step.

FIG. 16 is a cross-sectional side view of a wafer during step k of FIG. 15b.

FIG. 19 is a plan view of an X-Y addressable LED array mounted on a silicon substrate with associated silicon electronic circuitry.

FIG. 20 is a perspective view of a LED pixel from an X-Y addressable LED array embodiment of the invention.

FIG. 21 is a schematic side view of an IR to visible light converter embodiment of the invention.

FIG. 22 is a schematic diagram of the converter of FIG. 21.

FIG. 23 is a side view of an alternate embodiment of FIG. 21.

FIG. 24 is a side view of a pixel of a tri-color X-Y addressable LED array.

FIG. 25 is a plan view of the array of FIG. 24.

DETAILED DESCRIPTION OF THE INVENTION

I. Tiled Active Matrix Liquid Crystal Display

Figure 1:
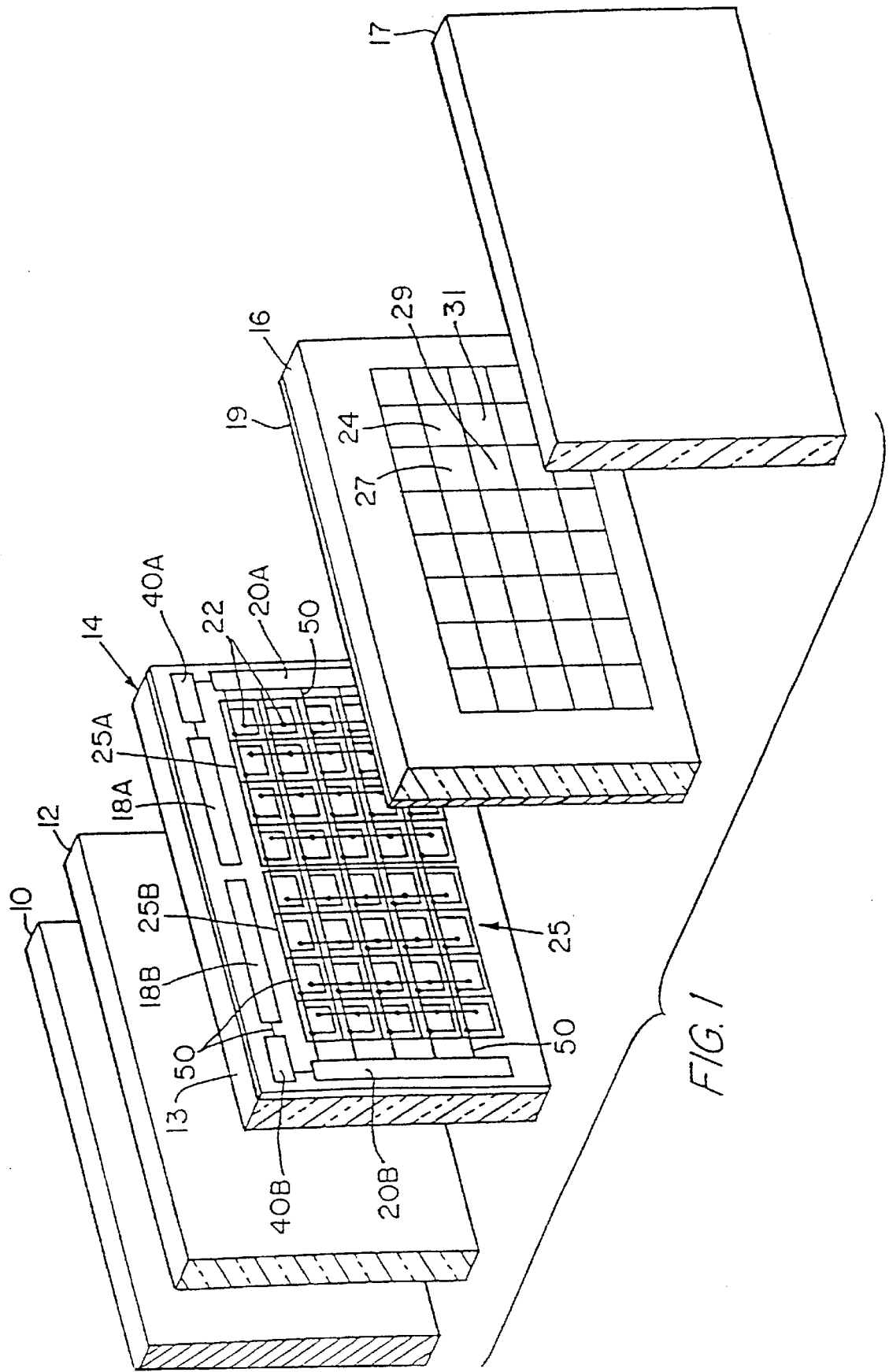
FIG. 1 is a perspective view of a high density circuit module in the form of an active matrix liquid crystal display (AMLCD).

A preferred embodiment of the invention for fabricating complex hybrid multi-function circuitry on common module substrates is illustrated in the context of an AMLCD for a head mounted display, as shown in FIG. 1. The basic components of the AMLCD comprise a light source 10, such as a flat fluorescent or incandescent white lamp, or an electroluminescent lamp having white, or red, blue and green phosphors, a first polarizing filter 12, a circuit panel 14, an optional filter plate 16 and a second polarizing filter 17, which form a layered structure. Note that filter plate 16 is not needed f or a black and white display or where the red, green and blue colors are provided by the lamp at the appropriate pixel. A liquid crystal material 23, such as a twisted nematic is placed between the circuit panel 14 and the filter plate 16.

Figure 2A:
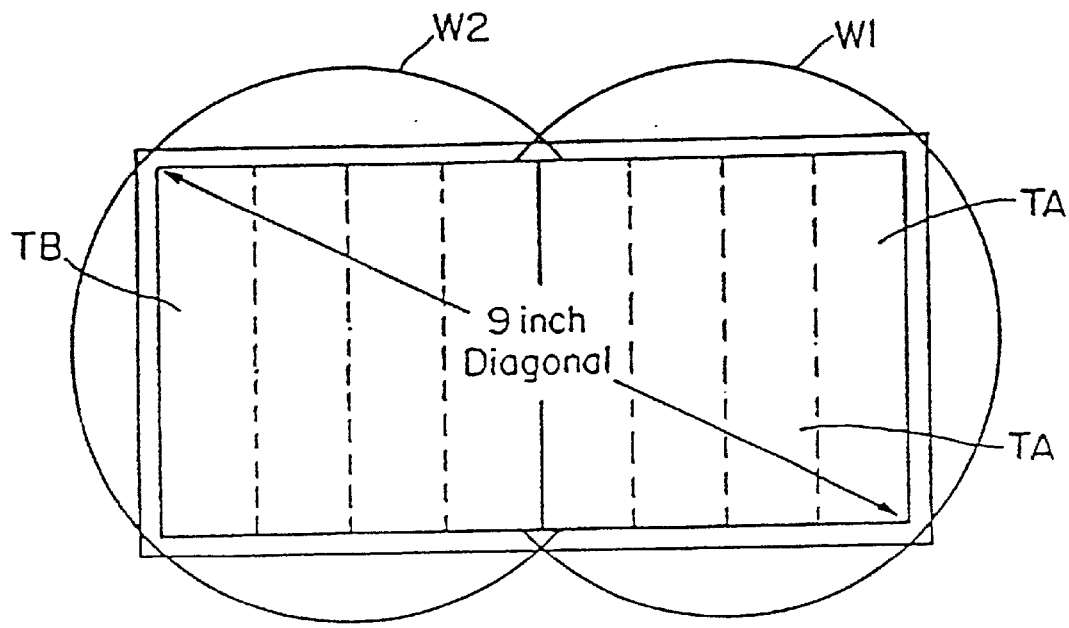
FIG. 2A is a schematic illustrating how two six inch wafers can be used to form tiles for a 4×8 inch AMLCD.
Figure 2B:
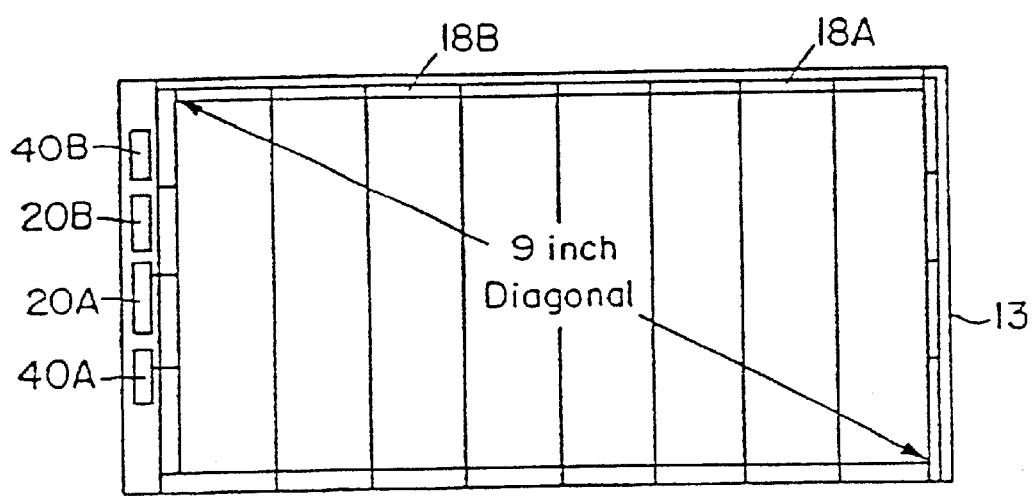
FIG. 2B shows the tiles of FIG. 2A applied to a glass substrate for forming an AMLCD.

Circuit panel 14 consists of a transparent common module body 13 formed, for example, of glass upon which is transferred a plurality of common multifunction circuits comprising control logic circuits 40A and 40B and drive circuits 18A and 18B, 20A and 20B, and array circuit 25A and 25B. Preferably, the logic and drive circuits which require high speed operation are formed in tiles of x-Si. The array circuits may be formed in $\alpha$-Si material, or poly-Si, or preferably in x-Si, to achieve lower leakage in the resultant TFT's and, hence, better grey scale. Higher speed is also achieved in x-Si. Displays as large as a 4×8 inch active matrix LCD array can be formed from two standard 6-inch diameter Si wafers W1 and W2 as shown in FIG. 2A. Array circuit 25A is formed on wafer W1 and 1-inch by 4-inch tiles TA are transferred from the wafer W1 to the substrate 14. Note that the transfer can be accomplished using either a single or double transfer process, as will be described in detail below. Each tile is registered against another using micropositioning equipment and manipulators capable of micron scale accuracy. Similarly, tiles TB are transferred from wafer W2 to form array 25B on substrate or common module body 13 (See FIG. 2B).

Logic circuits 40A and 40B and drive circuits 18A, 18B, 20A, 20B are formed on other suitable substrates (not shown) and tiled and transferred in like manner to common substrate 13 and registered opposite the arrays 25A, 25B, as shown in FIG. 1. Conductive interconnections 50 are then made between the drive circuits and the individual pixels 22 and the logic control circuits 40A and 40B. In this manner, a 1280 by 1024 addressable array of pixels 22 are formed on the substrate 13 of circuit panel 14. Each pixel 22 is actuated by voltage from a respective drive circuit 18A or B on the X-axis and 20A or B on the Y-axis. The X and Y drive circuits are controlled by signals from control logic circuits 40A and B. Each pixel 19 produces an electric field in the liquid crystal material 23 disposed between the pixel and a counterelectrode (not shown) formed on the back side of the color filter plate 16.

The electric field formed by pixels 22 causes a rotation of the polarization of light being transmitted across the liquid crystal material that results in an adjacent color filter element being illuminated. The color filters of filter plate system 16 are arranged into groups of four filter elements, such as blue 24, green 31, red 27, and white 29. The pixels associated with filter elements can be selectively actuated to provide any desired color for that pixel group.

Figure 3:
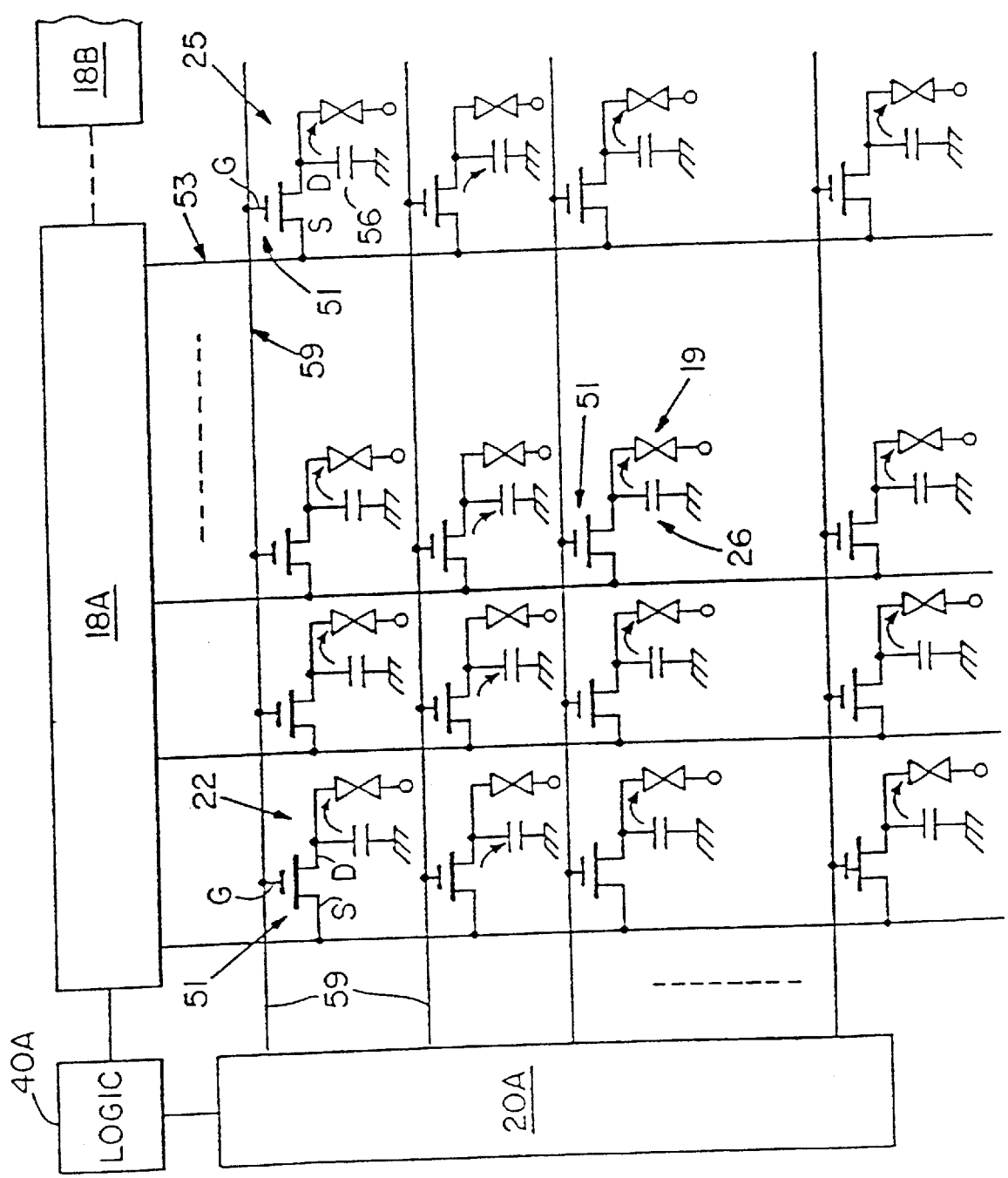
FIG. 3 is a circuit diagram illustrating the driver system for the AMLCD of FIG. 1.

A typical drive and logic circuit that can be used to control the array pixels 22 is illustrated in FIG. 3. Drive circuit 18A receives an incoming signal from control logic 40A and sends a signal to each source electrode of a TFT 51 in one of the columns selected by logic circuit 40A through interconnect line 53. Y-drive circuit 20A controlled by logic circuit 40A energizes a row buss 59 extending perpendicular to column buss 53 and applies a voltage pulse to each gate G of TFT's 51 in a selected row. When a TFT has a voltage pulse on both its gate and source electrode current flows through an individual transistor 51, which charges capacitor 56 in a respective pixel 22. The capacitor 56 sustains a charge on the pixel electrode adjacent to the liquid crystal material (shown schematically at 19) until the next scan of the pixel array 25. Note that the various embodiments of the invention may, or may not, utilize capacitors 56 with each pixel depending upon the type of display desired.

II. Transfer Processes

The array circuits 25A and 25B and logic 40A,40B and drive circuits 18A,18B may be formed and transferred by a number of processes. The basic steps in a single transfer process are: forming of a plurality of thin film Si circuits on Si substrates, dicing the thin film to form tiles, and transferring the tiles to a common module substrate by "tiling." Tiling can also be employed in fabricating III–V material circuits or hybrid Si and III–V material circuits or circuit components, which can be stacked to provide compact modules.

Tiling involves the steps of transferring, registering the transferred tiles, and adhering the registered tiles. The Si substrates are then removed and the circuits on the tiles are interconnected. The double transfer approach, described in detail below in connection with FIGS. 4A–4L is similar except that the Si-substrate is removed after dicing and the thin film is transferred to an intermediate transfer body or carrier before ultimate transfer to the common module body.

Assuming an Isolated Silicon Epitaxy (ISE) process is used, the first step is to form a thin-film precursor structure of silicon-on-insulator (SOI) film. An SOI structure, such as that shown in FIG. 4A, includes a substrate 32 of Si, a buffer layer 30, of semi-insulating Si and an oxide 34 (such as, for example, $SiO_2$) that is grown or deposited on buffer layer 30, usually by Chemical Vapor Deposition (CVD). An optional release layer 36 of material which etches slower than the underlying oxide layer 34 is then formed over the oxide 34.

For example, a silicon oxy-nitride release layer, comprising a mixture of silicon nitride ($S_3N_4$) and silicon dioxide ($SiO_2$) may be a suitable choice. Such a layer etches more slowly in hydrofluoric acid than does $SiO_2$ alone. This etch rate can be controlled by adjusting the ratio of N and 0 in the silicon oxy-nitride ($SiO_xN_y$) compound.

A thin essentially single crystal layer 38 of silicon is then formed over the release layer 36. The oxide (or insulator) 34 is thus buried beneath the Si surface layer. For the case of ISE SOI structures, the top layer is essentially single-crystal recrystallized silicon, from which CMOS circuits can be fabricated.

Note that for the purposes of the present application, the term "essentially" single crystal means a film in which a majority of crystals show a common crystalline orientation and extend over a cross-sectional area in a plane of the film for at least 0.1 cm$^2$, and preferably, in the range of 0.5–1.0 cm$^2$, or more. The term also includes completely single crystal Si. The thin films can have thicknesses in the range of 0.1–20 microns and preferably in the range 0.1–1.0 microns.

Figure 4A:
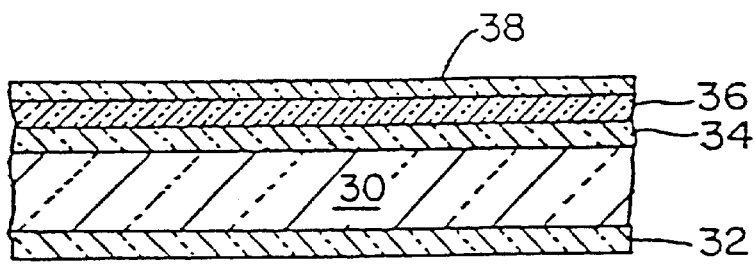
FIGS. 4A–4L is a preferred process flow sequence illustrating the fabrication of the a portion of the circuit panel for the AMLCD of FIG. 1.
Figure 4B:
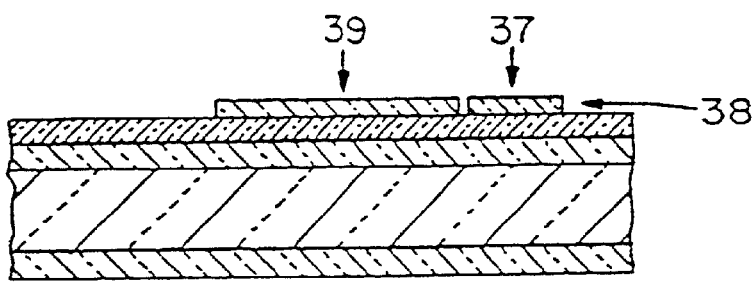
Figure 4C:
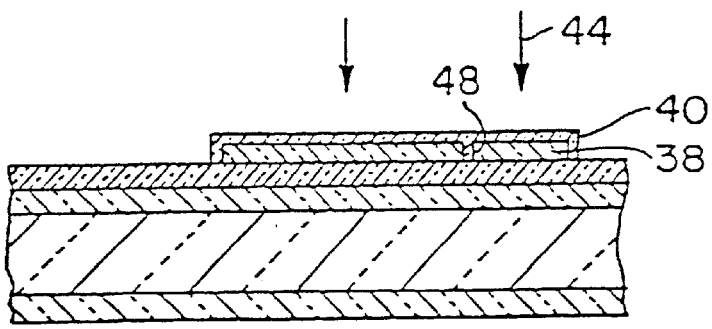

The use of a buried insulator provides devices having higher speeds than can be obtained in conventional bulk (Czochralski) material. Circuits containing in excess of 1.5 million CMOS transistors have been successfully fabricated in ISE material. An optional capping layer (not shown) also of silicon nitride may also be formed over layer 36 and removed when active devices are formed. As shown in FIG. 4B, the film 38 is patterned to define active circuits, such as a TFT's in region 37 and a pixel electrode region at 39 for each display pixel. Note that for simplification, only one TFT 51 and one pixel electrode 62 is illustrated (FIG. 4H). It should be understood that an array of 1280 by 1024 such elements can in practice be formed on a single 6-inch wafer.

A plurality of arrays may be formed on a single six-inch wafer, which can then applied to the display as tiles and interconnected. Alternatively, the plurality of pixel matrices from one wafer can be separated and used in different displays. The plurality may comprise one large rectangular array surrounded by several smaller arrays (to be used in smaller displays). By mixing rectangular arrays of different areas, such an arrangement makes better use of the total available area on a round wafer.

An oxide layer 40 is then formed over the patterned regions including an insulator region 48 formed between the two regions 37, 39 of each pixel.

The intrinsic crystallized material 38 is then implanted 44 (at FIG. 4C) with boron or other p-type dopants to provide a n-channel device (or alternatively, an n-type dopant for a p-channel device).

Figure 4D:
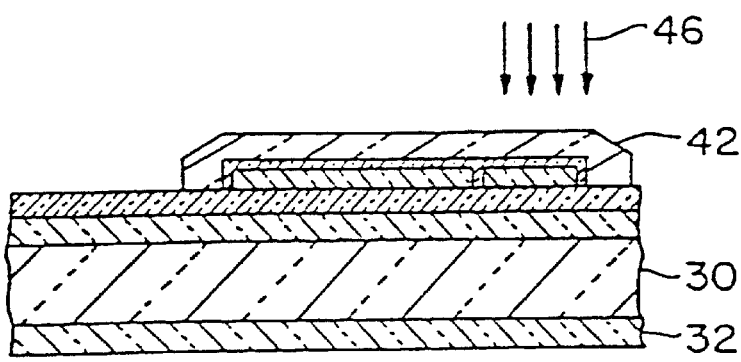
Figure 4E:
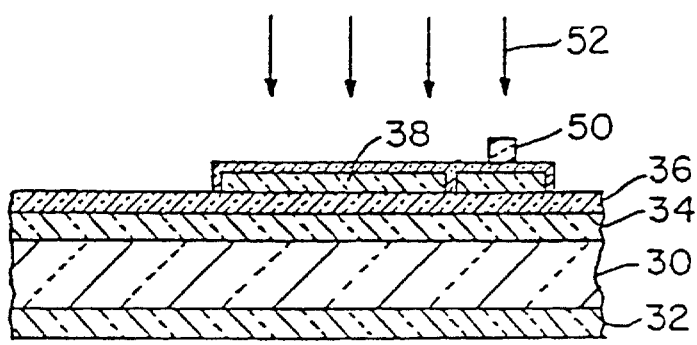
Figure 4F:
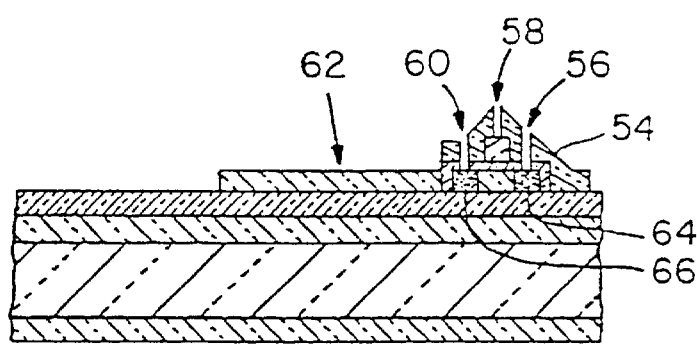
Figure 4G:
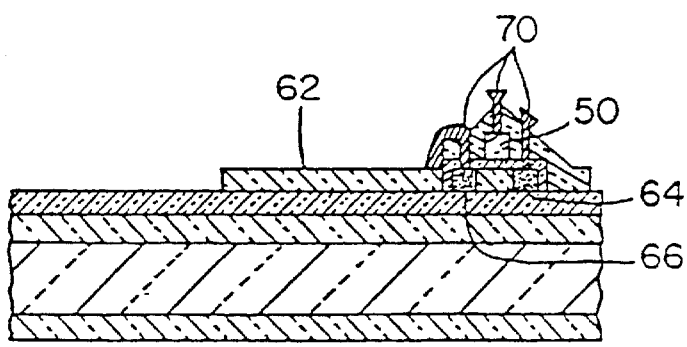
Figure 4H:
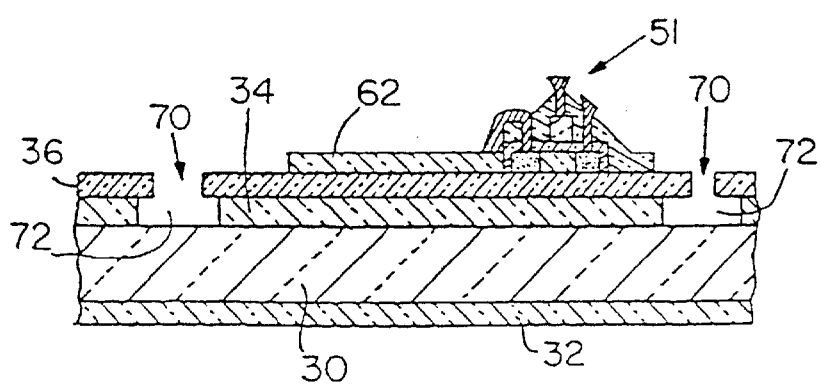

A polycrystalline silicon layer 42 is then deposited over the pixel and the layer 42 is then implanted 46, through a mask as seen in FIG. 4D, with an n-type dopant to lower the resistivity of the layer 42 to be used as the gate of the TFT. Next, the polysilicon 42 is patterned to form a gate 50, as seen in FIG. 4E, which is followed by a large implant 52 of boron to provide p+ source and drain regions 66, 64 for the TFT on either side of the gate electrode. As shown in FIG. 4F, an oxide 54 is formed over the transistor and openings 60, 56, 58 are formed through the oxide 54 to contact the source 66, the drain 64, and the gate 50. A patterned metallization 71 of aluminum, tungsten or other suitable metal is used to connect the exposed pixel electrode 62 to the source 66 (or drain), and to connect the gate and drain to other circuit panel components.

The devices have now been processed and the circuits may now be tested and repaired, as required, before further processing occurs.

The next step in the process is to transfer the silicon pixel circuit film to a common module, either directly, or by a double transfer from substrate to carrier and then to the common module. A double transfer approach is illustrated in FIGS. 4H–4L. To separate a circuit tile from the buffer 30 and substrate 37, a first opening 70 (in FIG. 4H) is etched in an exposed region of release layer 36 that occurs between tiles. Oxide layer 34 etches more rapidly in HF than nitride layer 36, thus a larger portion of layer 34 is removed to form cavity 72. A portion of layer 36 thus extends over the cavity 72.

Figure 4I:
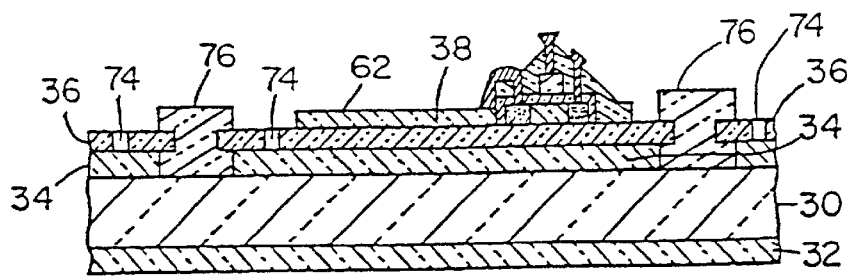
Figure 4J:
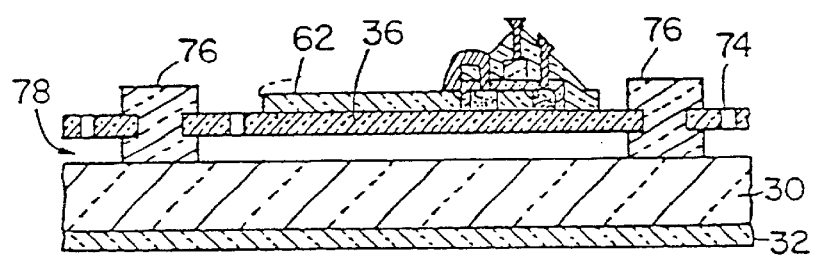
Figure 4K:
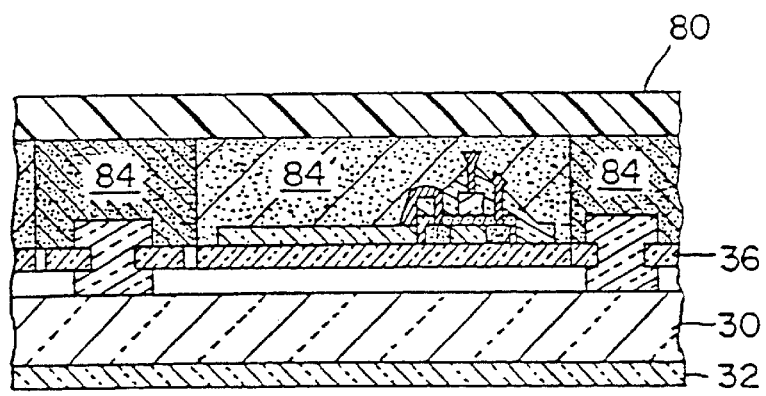
Figure 4L:
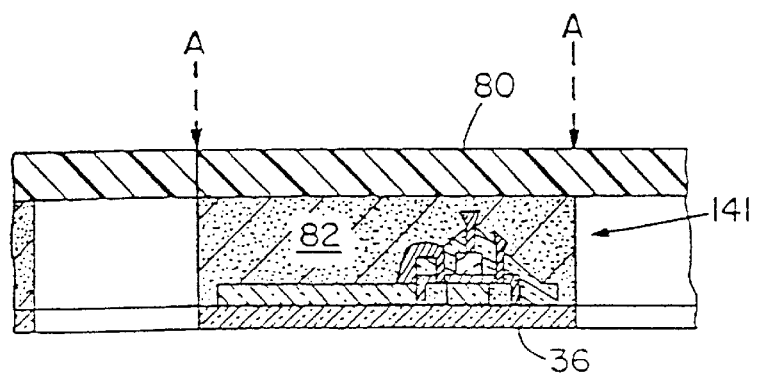

In FIG. 4I, a support post 76 of oxide is formed to fill cavity 72 and opening 70, which extends over a portion of layer 36. Openings or via holes 74 are then provided through layer 36 such that an etchant can be introduced through holes 74, or through openings 78 etched beneath the release layer 36, to remove layer 34 (See FIG. 4J). The remaining release layer 36 and the circuitry supported thereon is now held in place relative to substrate 32 and buffer 30 with support posts 76.

Next, an epoxy 84 that can be cured with ultraviolet light is used to attach an optically transmissive superstrate 80 to the circuitry, and layer 36. The buffer 30 and substrate 32 is then patterned and selectively exposed to light such that regions of epoxy 84' about the posts 76 remain uncured while the remaining epoxy 84' is cured (See FIG. 4K). The buffer 30 and substrate 32 and posts 76 are removed by cleavage of the oxide post and dissolution of the uncured 84 epoxy to provide the thin film tile structure 141, shown in FIG. 4L mounted on carrier 80.

To form the final display panel, the edges of the carrier 80 are trimmed to coincide with the tile borders. The nitride release layer 36 is removed by etching.

As shown in FIG. 5A, a plurality of tile structures 141 are then sequentially registered with one another and adhered to a common module body 110 using a suitable adhesive (not shown). Common module body 110 is preferably patterned with interconnect metallization on the surface facing the tile structure 141 for interconnecting individual tile circuitry with each other. Next, insulation and alignment layers, spacers, a sealing border and bonding pads for connections (not shown) are bonded onto the periphery of the common module body 110. A screen printing process can be used to prepare the border. As shown in FIG. 5B, a plate 117 containing the color filters 120 and the counterelectrode (not shown) is bonded to the periphery thin film circuit tiles 141 with the sealing border after insertion of spacers (not shown). The display is filled with the selected liquid crystal material 116 via a small filling hole or holes extending through the border. This filling hole is then sealed with a resin or epoxy. First and second polarizer films 118, 112 or layers are then bonded to both sides and connectors (not shown) are added. Finally, a white light source 114, or other suitable light source, is bonded to polarizer 112.

Pixel electrodes 62 are laterally spaced from each other. Each pixel has a transistor 51 and a color filter 120 or 122 associated therewith. A bonding element or adhesive 82 and optically transmissive superstrate 110, such as glass or plastic completes the structure. Body 110 is preferably a low temperature glass that can have a thickness preferably of about 200 to 1000 microns.

In an alternative CLEFT process, thin single-crystal films, are grown by chemical vapor-deposition (CVD), and separated from a reusable homoepitaxial substrate.

The films removed from the substrate by CLEFT are "essentially" single-crystal, of low defect density, are only a few microns thick, and consequently, circuit panels formed by this process have little weight and good light transmission characteristics.

The CLEFT process, illustrated in U.S. Pat. No. 4,727,047, involves the following steps: growth of the desired thin film over a release layer (a plane of weakness), formation of metallization and other coatings, formation of a bond between the film and a second substrate, such as glass (or superstrate), and separation along the built-in-plane of weakness by cleaving. The substrate is then available for reuse.

The CLEFT process is used to form sheets of essentially single crystal material using lateral epitaxial growth to form a continuous film on top of a release layer. For silicon, the lateral epitaxy is accomplished either by selective CVD or, preferably, a lateral recrystallization or ISE process, or other recrystallization procedures. Alternatively, other standard deposition techniques can be used to form the necessary thin film of essentially single crystal material.

One of the necessary properties of the material that forms the release layer is the lack of adhesion between the layer and the semiconductor film. When a weak plane has been created by the release layer, the film can be cleaved from the substrate without any degradation. As noted in connection with FIGS. 4A–4C, the release layers can comprise multi-layer films of $Si_3N_4$ and $SiO_2$. Such an approach permits the $SiO_2$ to be used to passivate the back of the CMOS logic. (The $Si_3N_4$ is the layer that is dissolved to produce the plane of weakness.) In the CLEFT approach, the circuits are first bonded to the glass, or other transfer substrate, and then separated, resulting in simpler handling as compared to, for example, UV-cured tape.

The plane of weakness is key to obtaining uniform cleaving between the circuits and the substrate. This plane may be formed by creating a pattern of carbon on the surface of the wafer so that only a small fraction of the underlying semiconductor surface is exposed. These exposed portions are used as nucleation cites for the epitaxial film. If the growth conditions are properly chosen, the film will grow laterally faster than vertically, leading to lateral overgrowth of the single crystal film. Within 1 $\mu$m of vertical growth, the film becomes continuous and of high quality. However, the carbon layer is weak and, combined with the small fraction of exposed semiconductor areas where the film is strongly attached to the substrate, creates a plane of weakness. This plane can be used reliably and reproducibly to separate the film from the substrate. The substrate may be reused. These processes have been used to transfer a wide range of GaAs and Si circuits to alternative substrates such as glass, ceramic, and other materials, without harm to the active circuitry.

In the ISE process, the oxide film is strongly attached to the substrate and to the top Si film which will contain the circuits. For this reason, it is necessary to reduce the strength of the bond chemically. This requires use of a release layer that is preferentially dissolved with an etchant without complete separation to form a plane of weakness in the release layer. The films can then be separated mechanically after the glass is bonded to the circuits and electrodes.

Mechanical separation may be accomplished by bonding the upper surface of the Si film to a superstrate, such as glass, using a transparent epoxy. The film and glass are then bonded with wax to glass plates about 5 mm thick that serve as cleaving supports. A metal wedge is inserted between the two glass plates to force the surfaces apart. Since the mask has low adhesion to the substrate, the film is cleaved from the substrate but remains mounted In the glass. The substrate can then be used for another cycle of the CLEFT process, and the device processing may then be completed on the back surface of the film. Note that since the device remains attached to a superstrate, the back side can be subjected to standard wafer processing, including photolithography.

Figure 6:
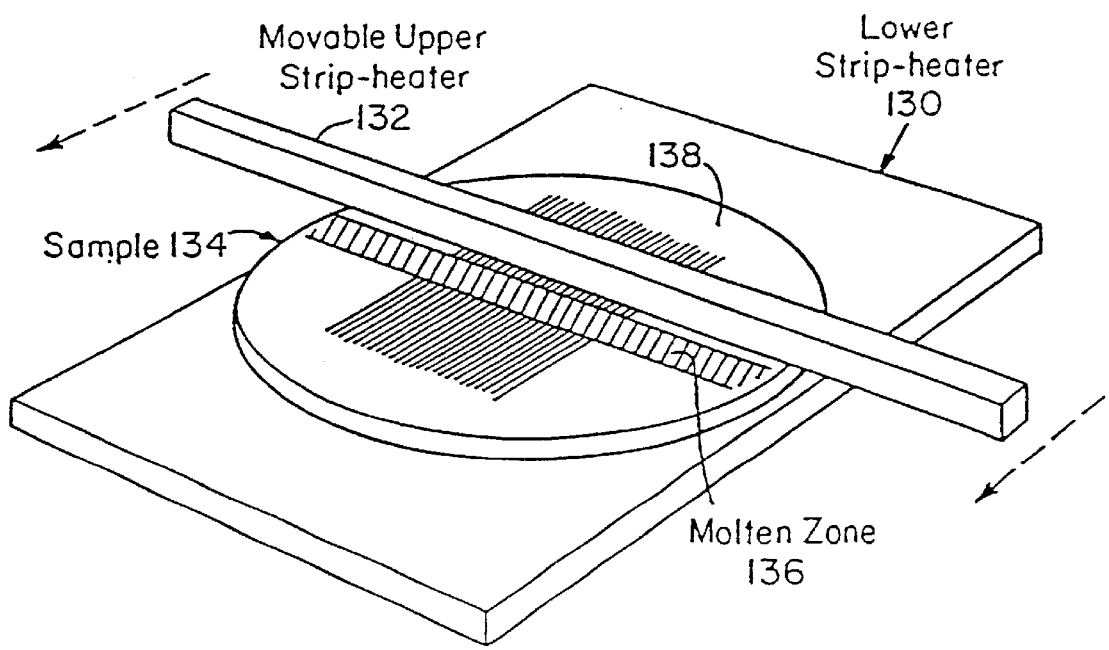
FIG. 6 illustrates in a perspective view a preferred embodiment of a system used for recrystallization.

One embodiment of the invention utilizes a recrystallization system, shown schematically in FIG. 6 to form the essentially single crystal Si thin film. A sample wafer 134 is formed of poly Si, formed on $SiO_2$, formed on an Si wafer. A capping layer 138 is formed over the poly Si. The wafer temperature is then elevated to near the melting point by a lower heater 130. An upper wire or graphite strip heater 132 is then scanned across the top of the sample 134 to cause a moving melt zone 136 to recrystallize or further crystallize the polycrystalline silicon. The lateral epitaxy is seeded from small openings formed through the lower oxide. The resultant single crystal film has the orientation of the substrate.

A number of unique devices and circuits have been formed using the above processing techniques. These techniques have been used to transfer CMOS active matrix LCD circuitry from ISE wafers to glass, and have yielded excellent displays with single crystal Si active matrix circuits. Silicon circuitry has been transferred to glass and shows no important changes in transistor characteristics after transfer. The technique has also been proved with III–V compound semiconductor circuits. For example, GaAs and AlGaAs monolithic series-connected photovoltaic energy converters have been made for power down a fiber application that yield exceptional performance. Also, two-dimensional multiplexed AlGaAs LED arrays (with over 32 K pixels) have been made by transfer and two-sided processing and exhibit extremely high LED density as well as performance. The development of this broad range of Si and III–V circuits indicates the general applicability of the transfer process to a wide range of devices and circuits.

III. Alternate Adhesion and Transfer Processes

Figure 7D:
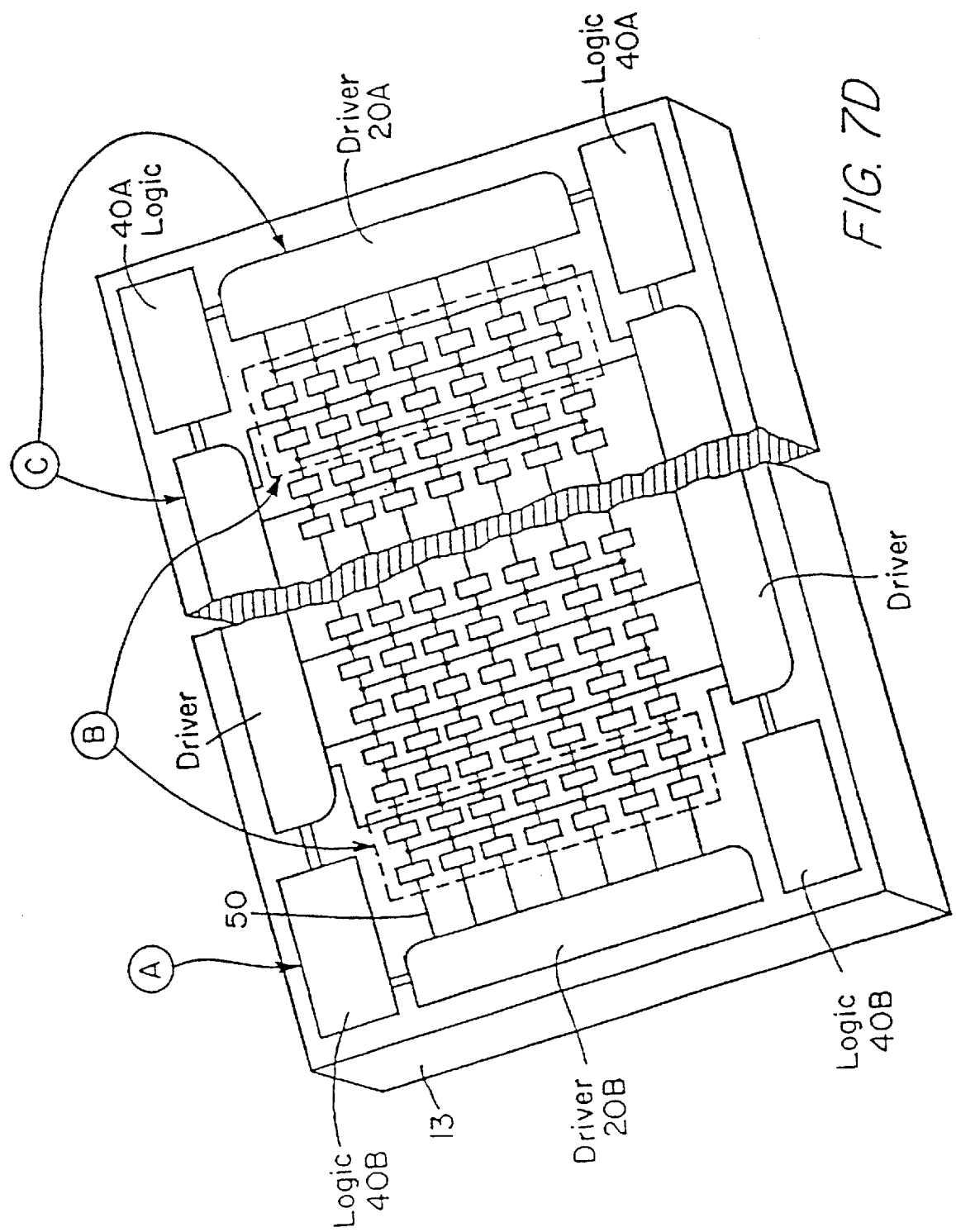

FIGS. 7A–7D illustrate an alternate preferred double transfer process for adhering and transferring tiles of circuits of thin films of silicon to a common module body. The starting structure is a silicon wafer 118 upon which an oxide layer 116 and a thin film of poly-Si, $\alpha$-Si or x-Si 114 is formed using any of the previously described processes such as ISE or CLEFT. A plurality of circuits, such as pixel electrodes, TFT's, Si drivers and Si logic circuits, are then formed in the thin film. FIG. 7A shows three such wafers, I, II, III. In wafer I, logic circuits 40 are formed. In wafer II, pixel electrodes 62 and TFT's 51 are formed. In wafer III, driver circuits 20 are formed. A wafer, or individual tiles diced from the wafer, is attached to a superstrate transfer body 112, such as glass or other transparent insulator, using an adhesive 120. The adhesive can comprise commercially available epoxies.

The wafer, or tile, is then cleaned and the native oxide 118 is etched off the back surface. Depending on the thickness of the wafer, it may take up to 5 hours to etch the Si 118 and oxide 116 layers. The solution etches silicon very rapidly, i.e. 2 to 3 microns/min., and uniformly if the wafers are held horizontally in the solution with the etching surface face up. The acid has a very low etch rate on oxide, so that as the substrate is etched away and the buried oxide is exposed, the etching rate goes down. The observer can monitor the process and to stop the etch in the buried oxide layer 116' without punching through to the thin silicon layer 114 above it. Wafers up to 25 mils thick and oxides as thin as 4000 Å have been successfully etched using this process. An alternative etchant is hydrazine, which has a much higher etch rate selectivity or ethylene diamine pyrocatacol (EDP).

When the silicon is completely gone, the vigorous bubbling, which is characteristic of silicon etching abruptly stops, signalling that the etching is complete.

The thin films 114 transferred to the respective glass superstrates 112 are now rinsed and dried. If not already provided with circuits 40, 51, 62 or 20, the films 114 can be backside circuit processed, if desired.

After all the necessary circuits are formed, as above, on transfer bodies 112, they may now be diced and tiled onto a common module body 13 (FIG. 7D) to perform a combined function, such as an AMLCD. The system can then be mounted on a helmet or head-mountable frame for direct or indirect viewing by the user.

The logic circuits 40 of transfer body 118 in col. A, FIG. 7C, are transferred to the border of module body 13, while the driver circuits 20 from the transfer body 118 in col. C, FIG. 7C, are disposed on the border between the logic circuits 40A and 40B.

Tiles of pixel electrodes 62 and TFT's 51 are formed by dicing or etching and are registered with respect to each other and pre-formed wiring 50 on module body 13, as shown in FIG. 7D.

After all the circuits are registered and adhered to the module body, the transfer body 118 and the epoxy 120 is removed using a suitable etchant, such as HF for the case of a glass transfer body.

Interconnection of circuits is achieved during registration or by direct laser writing where necessary. Also, if desired, the film can be transferred to another substrate and the first glass superstrate and adhesive can be etched off, allowing access to the front side of the wafer for further circuit processing.

Figure 8A:
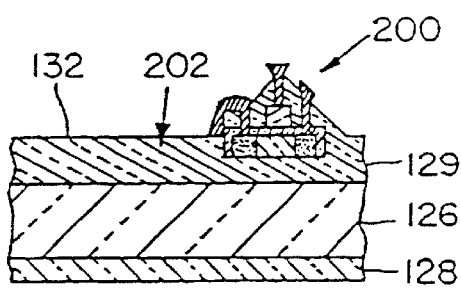
FIGS. 8A and 8B is a process flow sequence illustrating an alternative transfer process in which a GeSi alloy is used as an intermediate etch step layer.
Figure 8B:
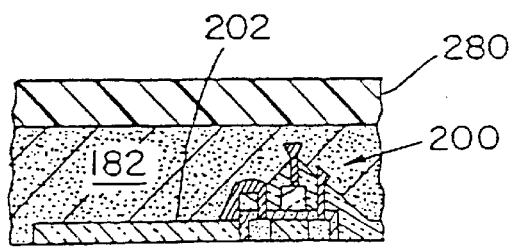

FIGS. 8A and 8B illustrate an alternative one-step silicon thin film transfer process in which GeSi is used as an intermediate etch stop layer. In this process, Si buffer layer 126 is formed on an x-Si substrate 128 followed by a thin GeSi layer 129 and a thin α-Si, poly-Si, or x-Si device or circuit layer 132; using well-known CVD or MBE growth systems.

The layer 132 is then IC processed in the manner previously described in connection with FIGS. 4E–H, to form circuits, such as TFT's 200 and pixel electrodes 202 (FIG. 8A). Next, the processed wafers, or tiles from the wafer, are mounted on a common module glass (or other) support 280 using an epoxy adhesive of the type previously mentioned in connection with FIGS. 7A–7B. The epoxy fills in the voids formed by the previous processing and adheres the front face to the superstrate 280.

Next, the original Si substrate 128 and Si buffer 126 are removed by etching, which does not affect the GeSi layer 129 (FIG. 8B). Finally, the GeSi layer 124 is removed by brief submersion in a suitable etch.

IV. Eye Tracker Embodiment

Figure 9:
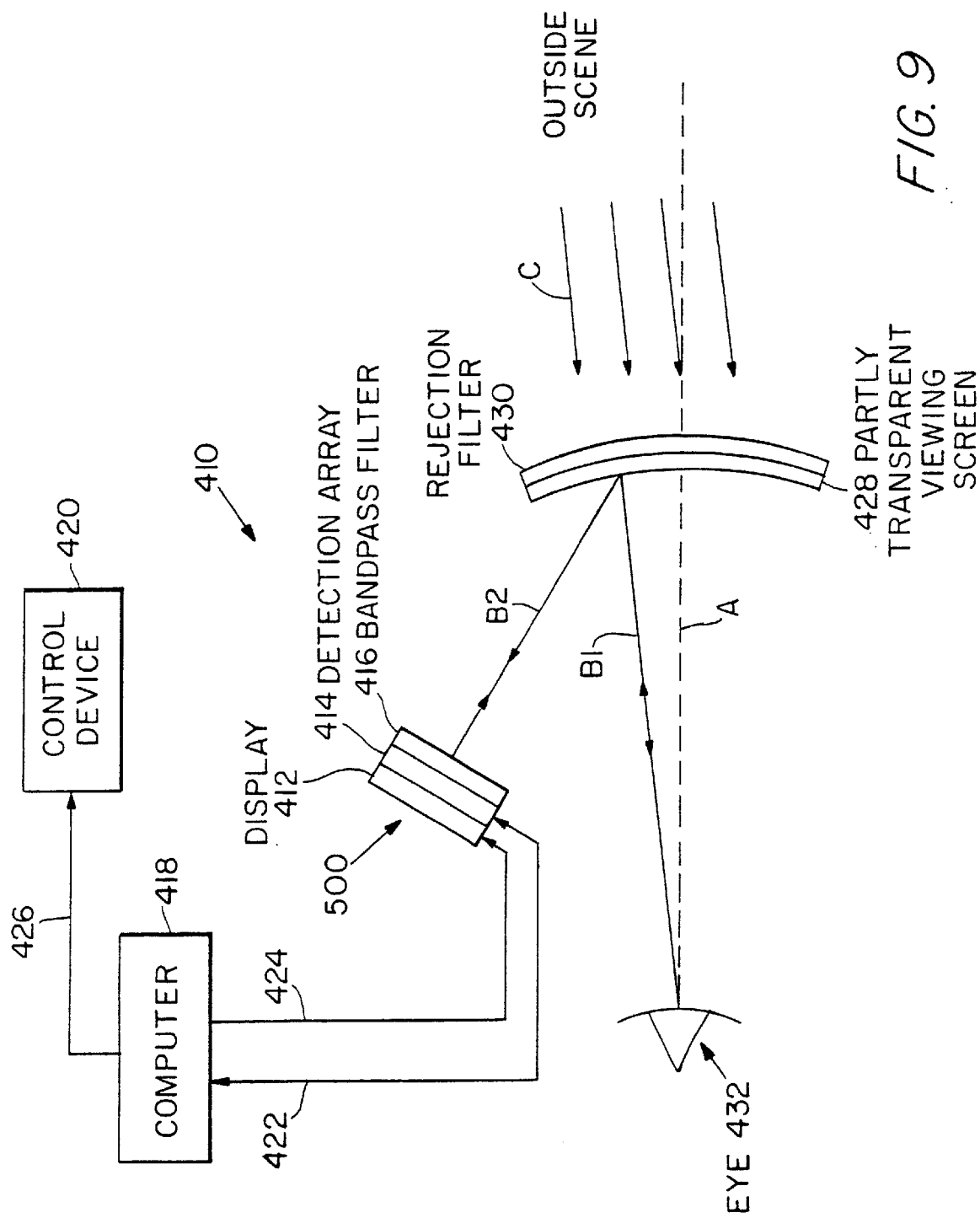
FIG. 9 is a schematic diagram of an eye tracking system of the invention.

Referring now to the schematic diagram of FIG. 9, it may be seen that the present invention relates to an eye tracking system 410 that combines a flat panel display device 412 with an array of optical detectors 14 to form an eye tracker device 500. The flat panel display device is used as a monolithic substrate and light source for determining the position of the eye 432. The detector array 414 is aligned and transferred onto the active matrix electronics of the flat panel device. A test pattern and software in computer 418 analyzes the sensed data generated by the detector on display and determines the position of the eye.

Light from display 412 is used to project an image onto viewing screen 428 for viewing by the eye(s) 432 of a viewer. The image to be displayed is generated in computer 418 and is coupled as an electrical input video signal to display 412 along line 424. Image light rays from display 412 pass through detector array 14 and are projected onto screen 428 where they may be superimposed on external images from an outside scene formed by light rays C.

A video signal source provides video signals to the display device 412. The video signal source can be any analog or digital video signal source including a Video Graphics Array (VGA) adaptor, National Television Systems Committee (NTSC) composite video source high-resolution professional display adapters, Charge-Coupled-Devices (CCD), or other similar sources. In a preferred embodiment a CCD camera is mounted on the head mounted system so as to generate an image of the surroundings of the user and which is linked to the display of the head mounted system. This permits the user to look in a particular direction and receive an image on his/her display or viewing screen from the surrounding area. The display can be programmed to overlay selected images onto the sensed image. The eye tracker can be used to enhance the resolution of the image region that the user's eyes are directed upon. Horizontal and vertical synchronization signals from the video signal source are provided to a video interface. Red-Green-Blue (RGB) video signal components, if supplied by the video signal source, are provided to an encoder. If discrete red, green and blue signals are not supplied by the video source (e.g., NTSC composite video signal), then a single video signal must be supplied by the video source.

The display device 412 operates as a multi-frequency display device. Typically, video signals from the video signal source will not be synchronized to a fixed frequency. For example, a VGA adaptor generates synchronization signals that vary depending on the particular video mode in which the adaptor is operating. A standard VGA adaptor may generate a vertical synchronization frequency between about 56 and 70 Hz and a horizontal synchronization frequency between about 15 and 35 kHz. For professional display purposes (e.g., CAD/CAM) the vertical and horizontal synchronization frequency may be higher than described. To handle current high resolution displays, the display device 412 must adapt to vertical synchronization frequencies up to about 100 Hz and horizontal synchronization frequencies up to about 66 kHz. Consequently, the display device 412 adapts to changes in the synchronization frequencies.

A light ray emanating from a particular pixel of display 412 is shown as line B2. This ray is reflected by the screen 428 (line B1) onto the eye optics (not shown) and on to the macula (not shown) of eye 432. The axial rays of greatest importance will impinge on the fovea of the eye, the most sensitive part of the macula. These rays return to the display in the vicinity of the original pixel because reflection from the fovea is approximately normal to the retina and therefore nearly axial. Non-axial rays which will impinge on the retina beyond the fovea will not be reflected back along the axial optical path and will not return to the detector array 414.

The viewing screen 428 can comprise, for example, the visor of a heads-up helmet mounted optical system for pilots and the integrated detector/display can be inserted in a helmet-mounted optical system without physical modification to the helmet or optics. Additionally, no physical contact with the eye is required.

Once the axial rays B1, B2 return to the display, the detector array 14 identifies the portion of the array from which the axial ray emanated, by generating a voltage signal by a detector pixel located in the array nearest the returned ray. That portion of the array is, of course, the part of the display focussed on by the user. A test pattern from computer 418 is then interlaced with the display image to enable initial determination of the eye's position. Software, in computer 418, provides a cursor image for display 412 which is projected on screen 428 at the line-of-sight location. This cursor is interlaced to provide constant feedback to the detector array 414. The interlace frequency can be adjusted to make the cursor visible or not visible to the user.

Figure 10:
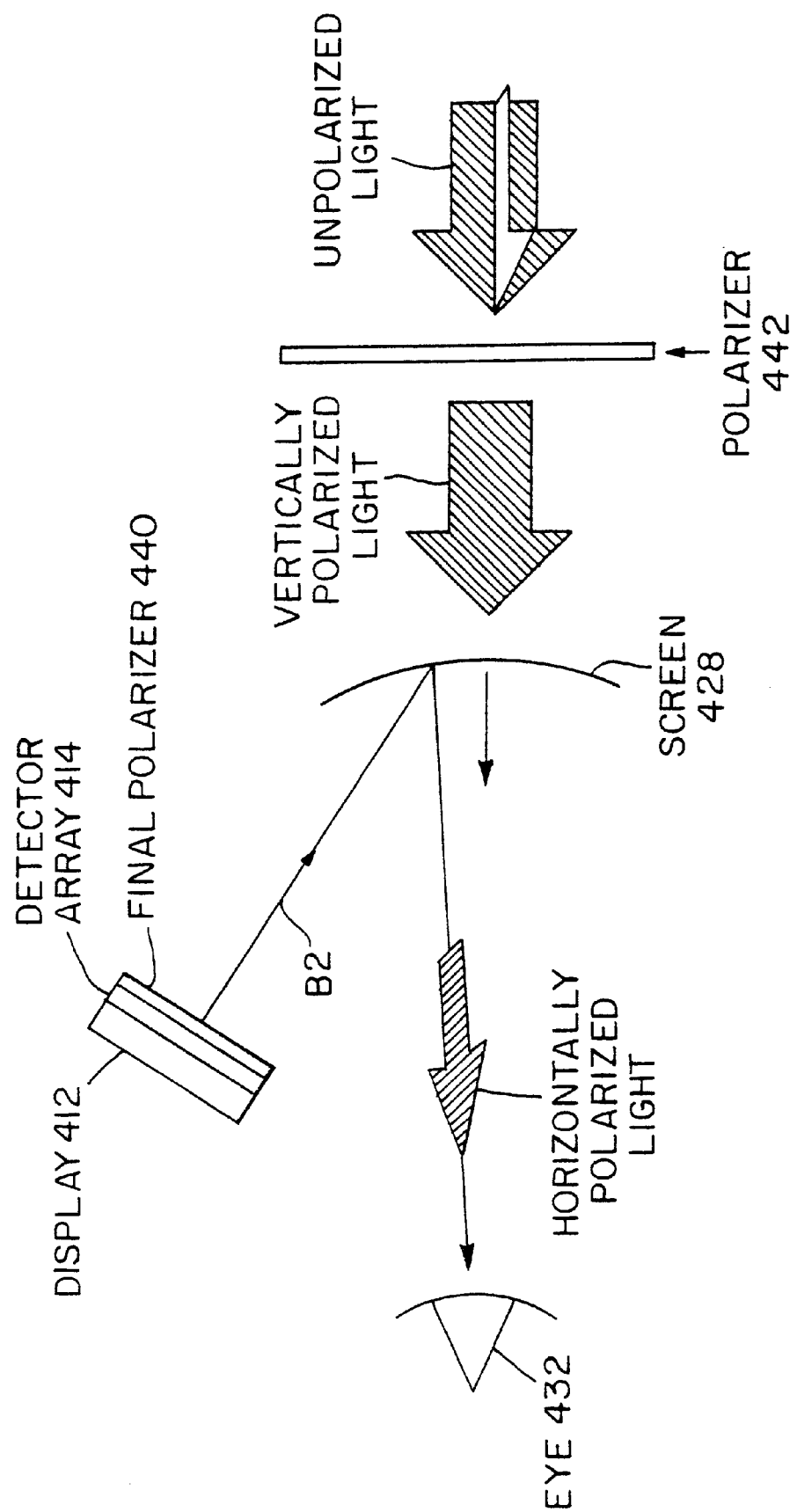
FIG. 10 is a schematic of an alternate embodiment of an eye tracking system of the invention.

For the case of a partially transparent system of FIG. 9 in which scenes from the surroundings are superimposed on the display image, the detector array 414 is provided with a narrow band pass filter overlay to reject all wavelengths except the wavelength of the cross hair or cursor, which must be one of the display primary colors. Suppose for example that the selected color is primary red. In this case, a narrow band red rejection filter 430 is placed on the outside of the screen 428, and a narrow red bandpass filter 416 is placed over the pixels of the detector array 414. In this way, the detector array 414 only receives light originating from the display. A second method of accomplishing the same result is to use polarizing filters as shown in FIG. 10. In this case the flat panel display 412 is an AMLCD light valve helmet or head mounted display (HMD), having a polarizer 440 on its output face. The polarized nature of the light from the display 440, combined with a 90° crossed polarizer 442 on the screen 428, prevents unwanted light from the outside scene from propagating to the detector array. Further partially transparent imaging systems are described below in connection with FIGS. 37A–37C.

Another alternative is to chop or rapidly blink the video signals from computer 418 for the cursor presentation so that software in the computer can subtract the background light. Yet, another alternative that can be used with LCD displays is to use infrared light that can pass through the red filters of the LCD. But this approach requires an IR rejection filter on the front of the viewing screen. It can be seen from the above that there are a number of methods of using the display 412 to provide a signal for the detector array 414, without interference from outside light.

Figure 11:
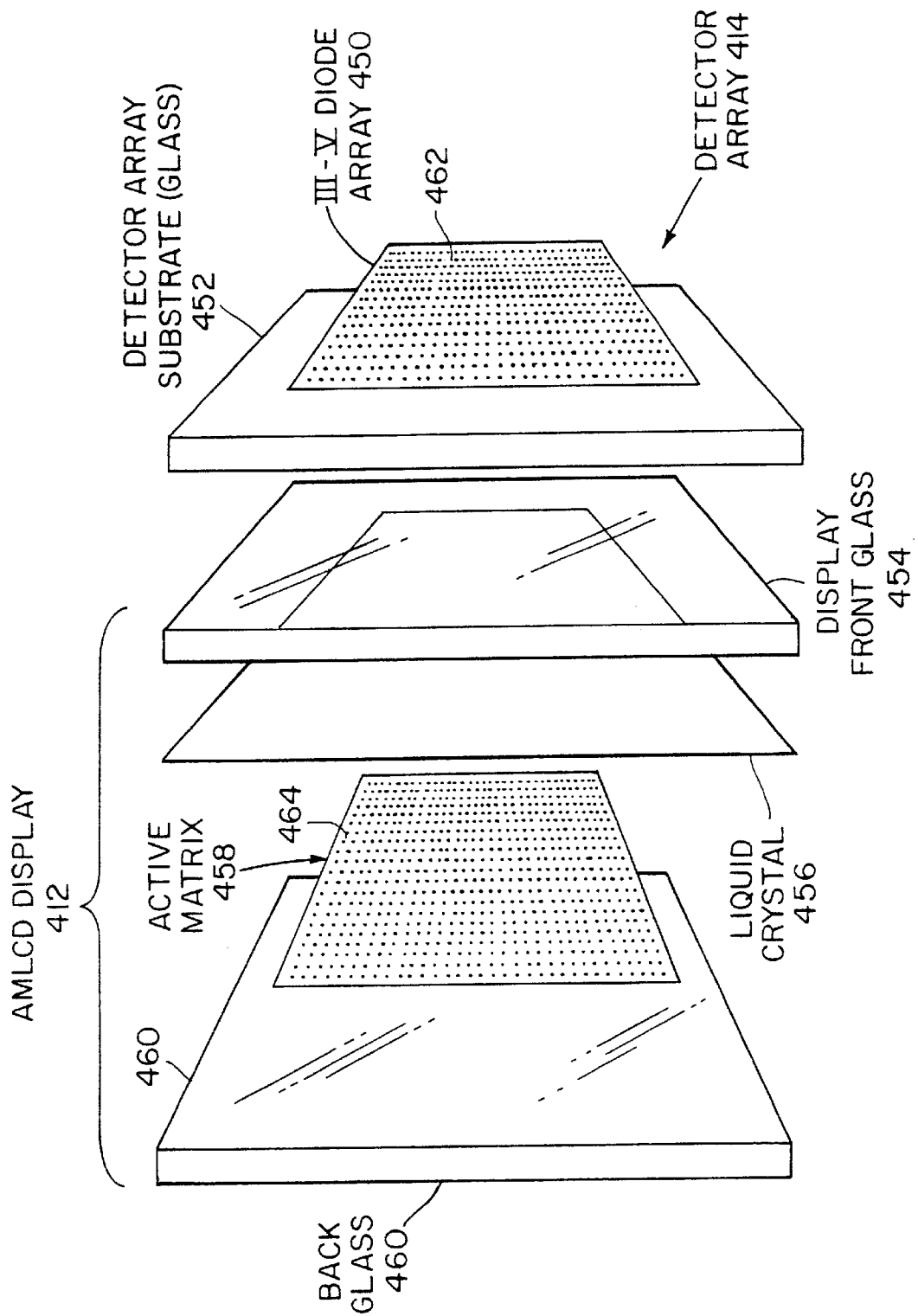
FIG. 11 is an exploded view of the integrated display/detector array panel (eye-tracker) of the invention.

An exploded view of an AMLCD display and monolithic detector array 414 in accordance with the invention is illustrated in FIG. 11. Note that a complete eye-tracker package can be made without substantially changing the overall dimensions of the display. As shown in FIG. 11, a detector array 414 is formed of a III–V diode array 450 transferred to a glass substrate 452 or directly above and onto front glass 454 of an active matrix LCD display 412. The detector pixels 462 are positioned so that each is completely above the drive transistors 464 of the active matrix circuit and therefore do not block any of the display's light output from pixel electrodes 464. (See FIG. 12). The detector row and column interconnects (not shown) are positioned directly above the display row and columns, so that the interconnect wires do not block any light.

Figure 12:
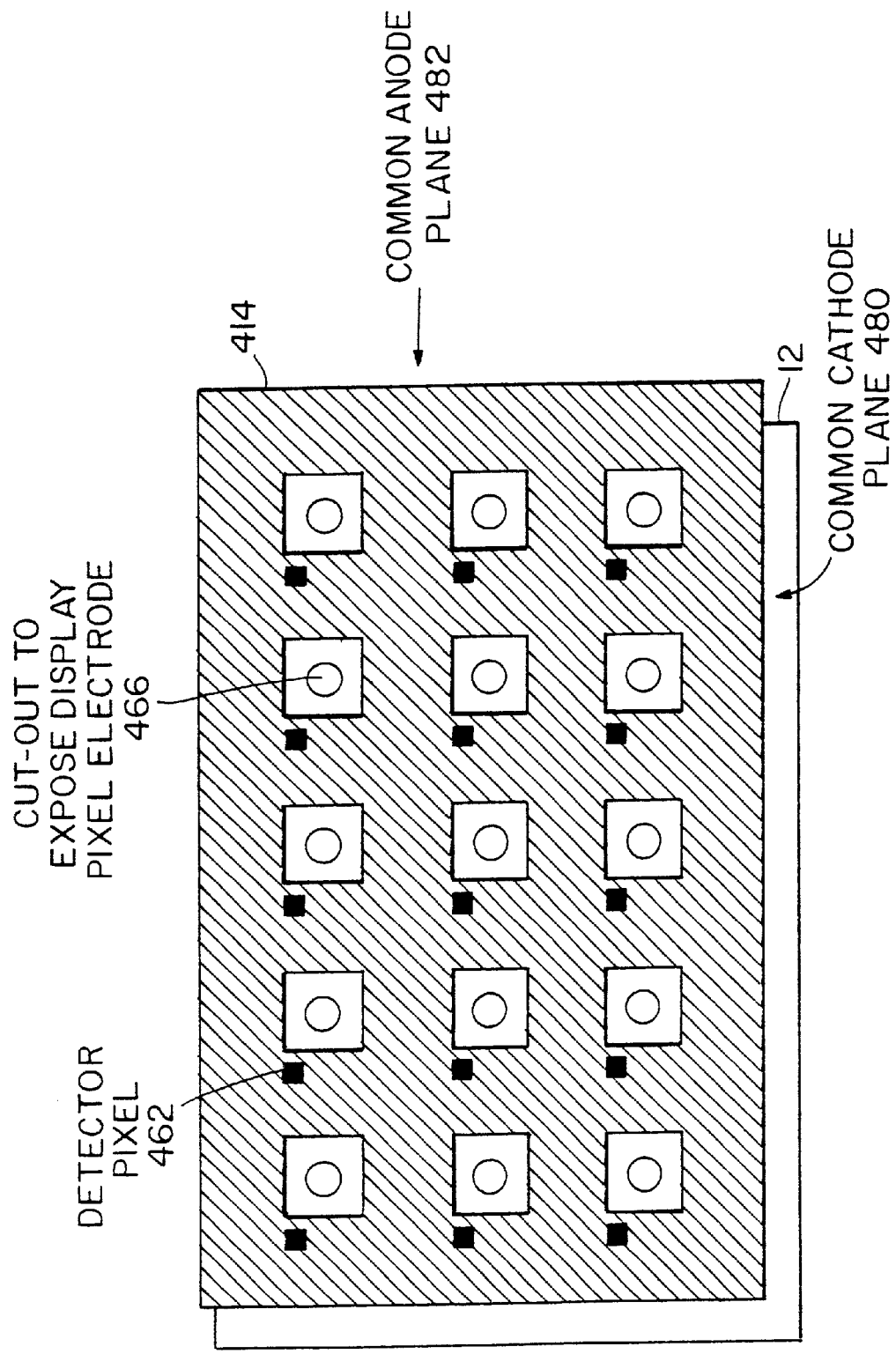
FIG. 12 is a plan view of a simplified version of the eye tracker in which the matrix array metallization is replaced by a common parallel interconnect.

Note that the cut-out shown in FIG. 12 is not required in practice since the detector array substrate 452 is made of transparent material such as glass or quartz.

For infrared detection, GaAs appears to be the best choice for the detector elements. The bandgap of GaAs is 1.43 eV, corresponding to an absorption edge of about 0.87 $\mu$m. This material may also be suitable for visible light; however, if it is desirable to suppress infrared absorption in the detector, the bandgap can be increased to about 1.9 eV (0.65 $\mu$m) by adding aluminum (Al) to form the ternary compound semiconductor $Al_xG_{x-1}As$. (A bandgap of 1.9 eV is obtained for x=0.38.)

The process used to form the detector array is based on an LED array process as a baseline. In this process, the detector material 470 is first grown on substrate 472 by OMCVD. A release layer 474 is formed that permits the epitaxial film 470 to be separated from the substrate 472, but separation is deferred until after the front side metallization 476 is formed (FIG. 13A). After metallization of rows of metallization and mesa etching to delineate the pixels 462, the surface of the wafer is bonded to a carrier 478 (FIG. 13B). This carrier is preferably the front panel 454 of display 412. The substrate 472 is then removed to yield a partially processed detector array 414 bonded to a display array 412. The processing is then completed to form a matrix addressed two-dimensional array 412 of detector pixels 462 aligned with the TFT's 464 (indicated by X's) but slightly displaced from corresponding pixel electrodes 466 (indicated by dots) of the display array 412 (FIG. 13C).

The fabrication of an X-Y multiplexed array, in accordance with the invention, begins with the epitaxial growth of the requited hetero-epi-layers of AlGaAs and GaAs layers on a GaAs or Ge substrate. In the case of the GaAs substrate 616, an optional layer 614 of AlAs is formed between the active AlGaAs layers 616 and the substrate 612 to facilitate substrate removal by the etch-off method. The AlAs forms an etch stop layer. [Alternatively, the X-Y array can be removed from the substrate by a CLEFT process or chemical epitaxial lift-off]. In the case of Ge substrates, a layer of AlAs can be used as an etch stop, but AlAs is not really necessary, since the Ge substrate can be dissolved in $H_2O_2$ without harm to the AlGaAs active layers.

Figure 14A:
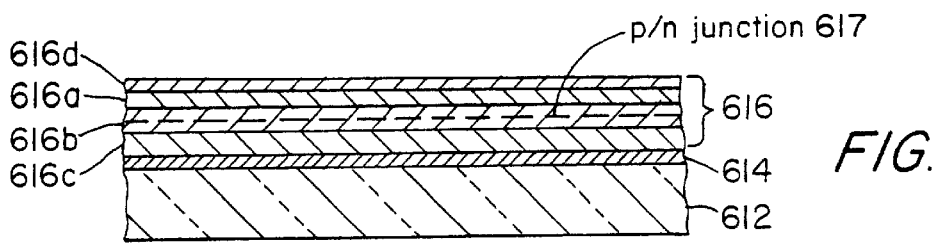
FIGS. 14A–B are schematic section views of a wafer being processing to form an X-Y addressable LED array.
Figure 14B:
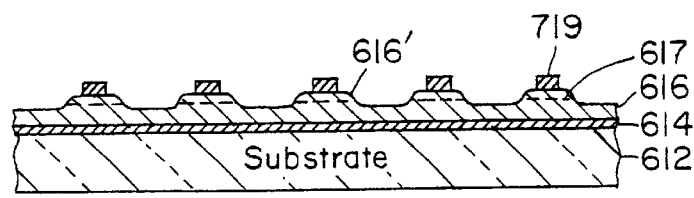

FIG. 14A shows the epitaxial layer structure to comprise a bottom cladding layer 616c of AlGaAs, an active GaAs (or AlGaAs) layer 616b in which a p-n junction 617 is formed by carbon doping during growth, a top cladding layer 616a of AlGaAs and thin GaAs contact layer 616d, all formed by OMCVD. A pattern of contact pads 719 and busbars (not shown) is formed by photolithographic techniques, evaporation, and/or electroplating on the front surface, as shown in FIG. 14B. Next, the p/n junctions 617 are isolated by etching part way into the epi-layers 616, as shown in FIG. 14B. This step is not absolutely required at this point, however, it simplifies a later etch step in the process.

Figure 14C:
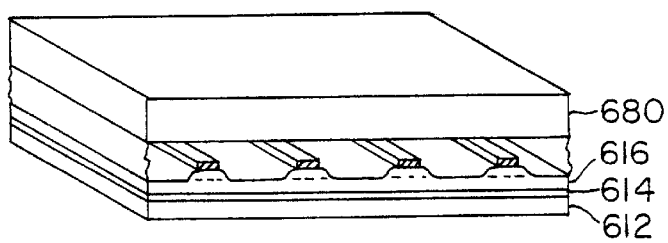
FIGS. 14C–E are schematic partial perspectives showing a wafer during successive additional process steps.
Figure 14D:
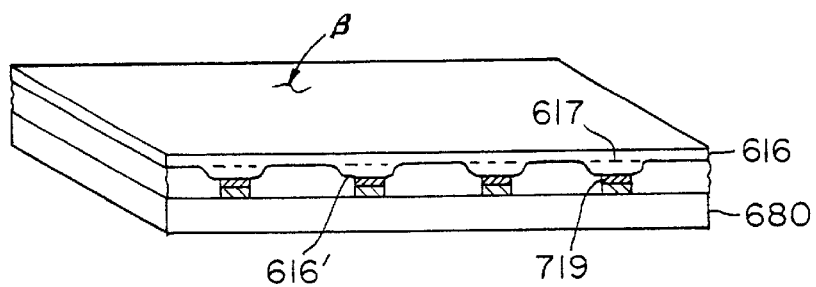

The next stage of the process consists of bonding of the wafer to a support 680, such as glass, ceramic, or thin stainless steel. (If the support is transparent to infrared radiation, downstream front-to-back alignments are facilitated, but the alignments can also be carried out by careful registration to the support edges.) The processed front side is bonded to the support 680 using a suitable adhesive (not shown) (FIG. 14C). After the support 680 is attached, the wafer or substrate 612 is etched off (or cleaved off) leaving the LED film 616 attached to the support 680, as shown in FIG. 14D, in which the structure has been flipped over onto the support to expose the backside B for processing.

Once the backside is exposed, any remaining non-essential material is removed from the back by selective etching in HF to expose a clean GaAs contact layer B. The backside (X-axis) contacts 721 and busbars 721x are now photolithographically patterned and electroplated or evaporated onto the contact regions 616'.

Figure 14E:
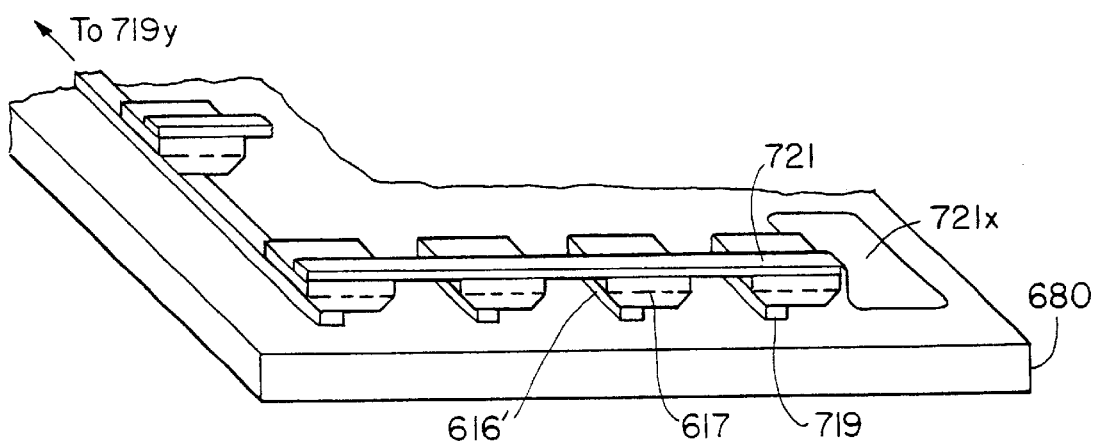
Figure 15A:
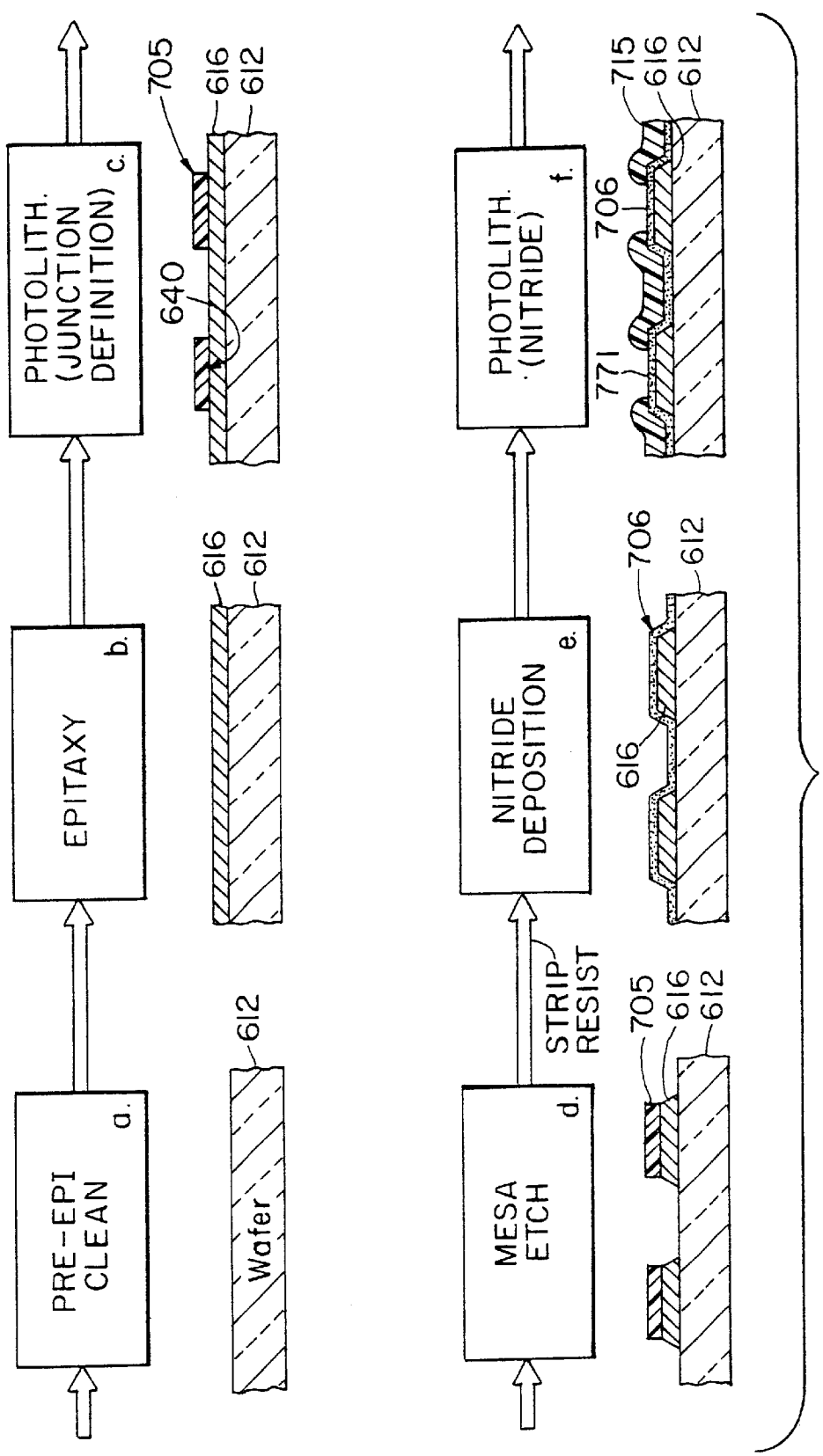
Figure 17:
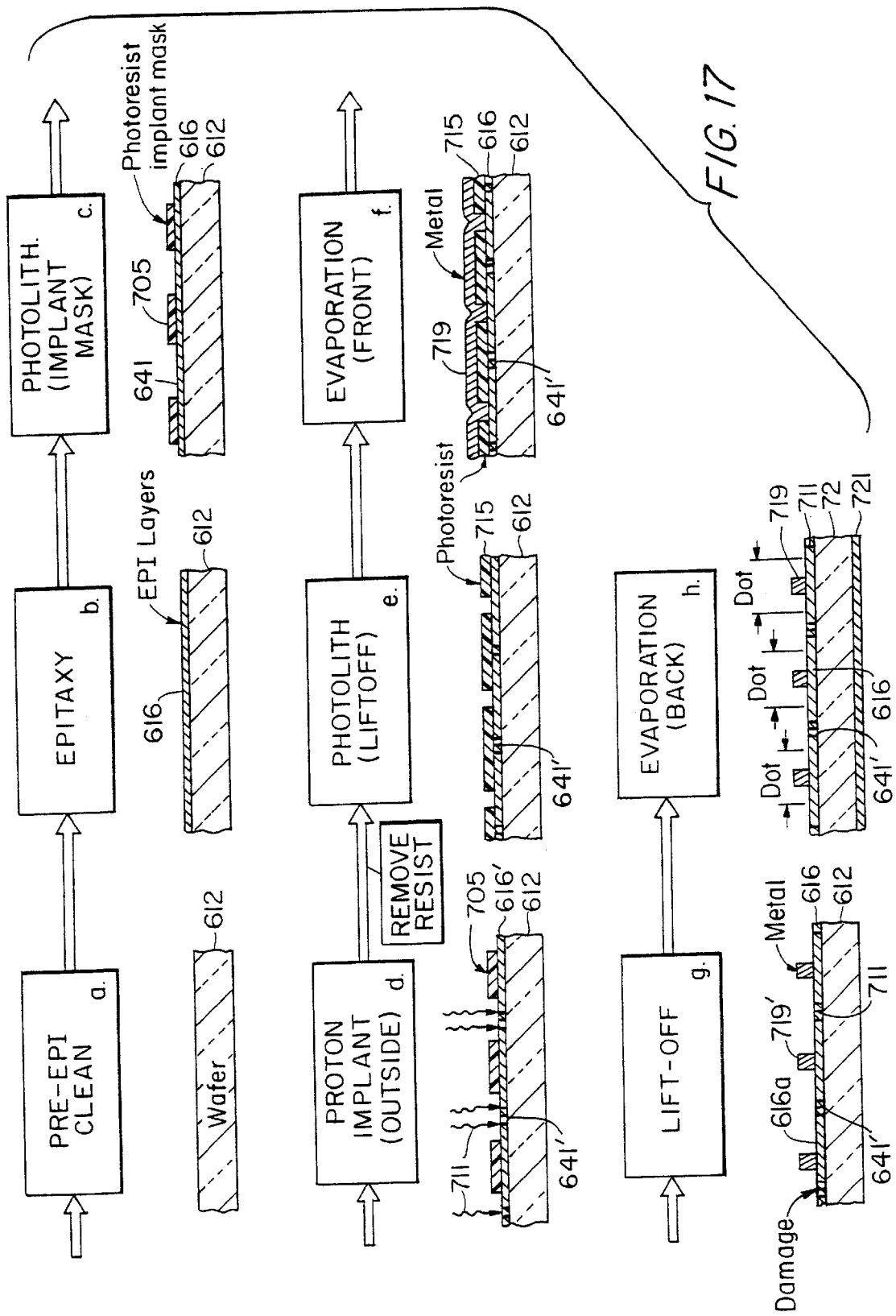
FIG. 17 is a process flow diagram of the main steps in fabricating an LED bar in accordance with an alternate process with a corresponding schematic sectional view of a wafer structure so processed shown beneath each step.
Figure 18A:
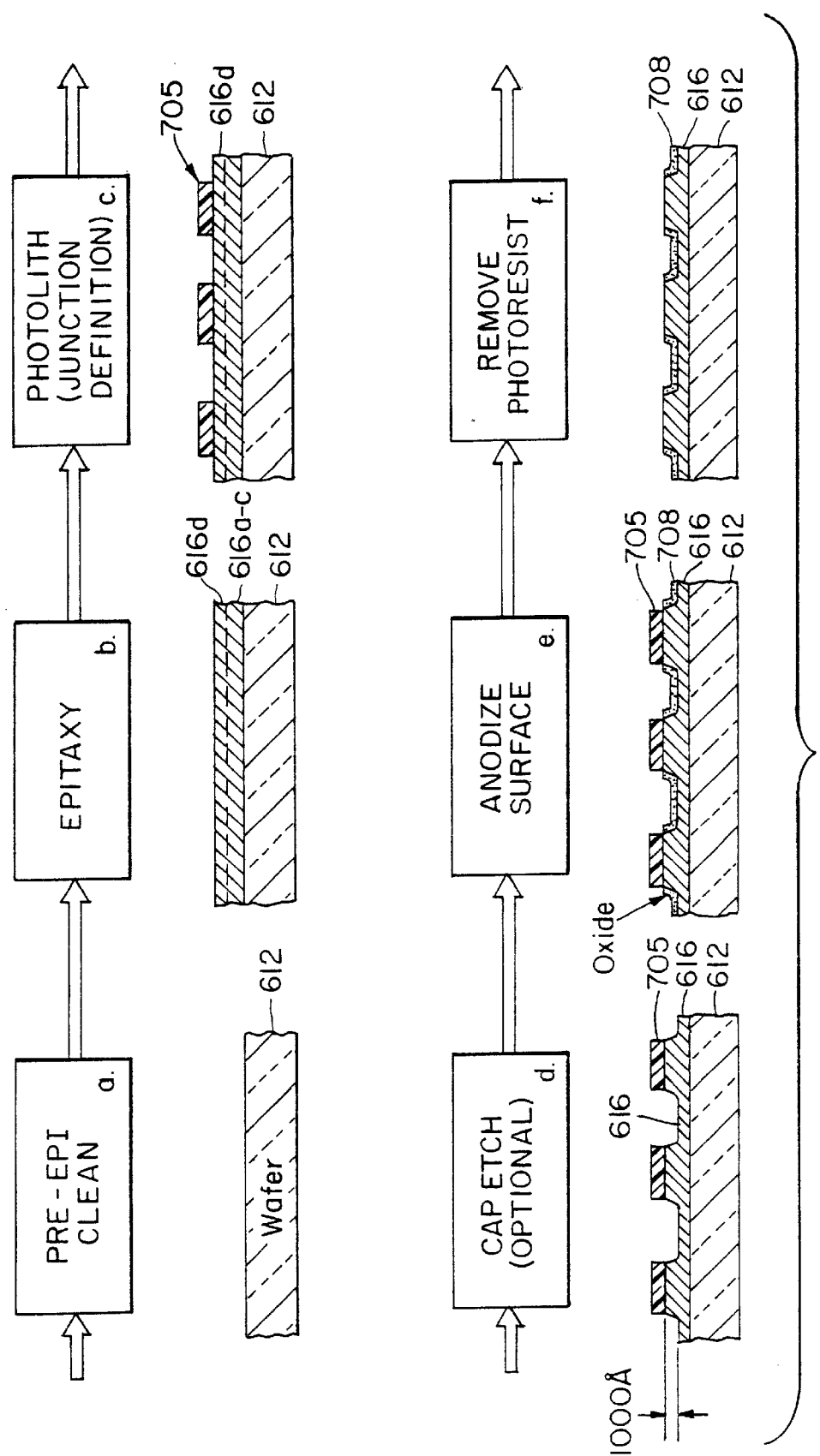
FIGS. 18A–18B is a process flow diagram of the main steps in fabricating an LED bar in accordance with yet another alternate process with a corresponding schematic sectional view of a wafer structure so processed shown beneath each step.
Figure 18B:
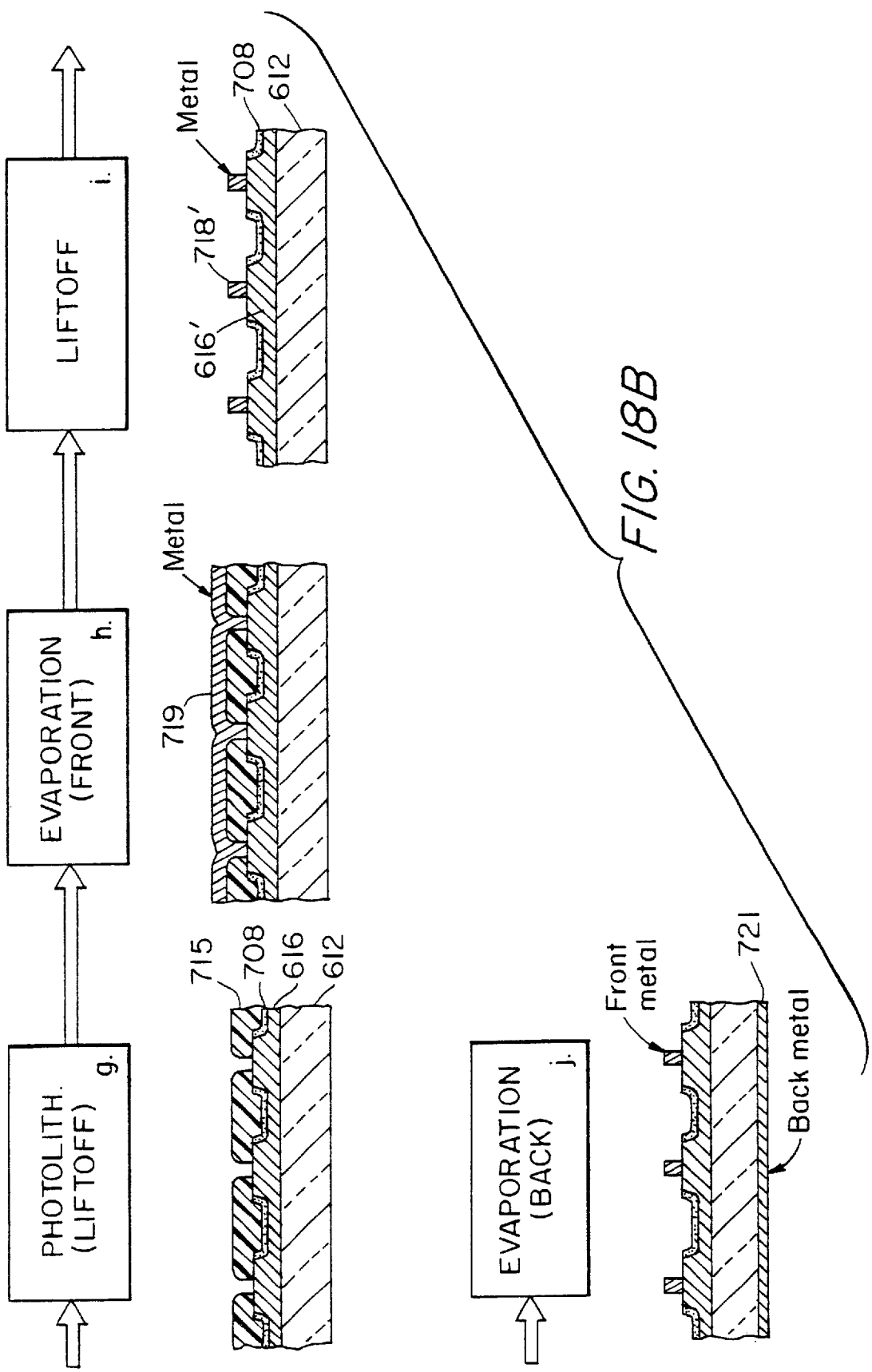

Finally, the backside is exposed to the mesa etch to totally separate the dots. At this point, all of the epi-material between the pixels is removed (FIG. 14E). Alternately, the isolation may be completed by implant isolation, or by limiting the current spreading. FIGS. 15, 17 and 18 summarize the important steps of three alternate processes for fabricating LED's in accordance with the invention. Beneath each step is the corresponding wafer structure shown in side view.

Referring now to FIG. 15, a mesa isolation method of dot definition is shown therein. Note that for each process step block, the corresponding structure is illustrated in section below. Step a comprises pre-epitaxial cleaning of wafer 612 using well known techniques, such as soaking in H$_2$SO$_4$/ H$_2$O$_2$ and H$_2$O followed by OMCVD deposition of AlGaAs/ GaAs epi-layers 616, in which a p-n junction is formed in the active GaAs layer (Step b).

Next, using well known photolithography techniques, individual dot junction areas 640 are defined over the surface of epi-layers 616 beneath areas of photoresist 705 (Step c). Next, the exposed epi-layers 616 are etched away down to just below the p/n junction or alternatively all the way down to substrate 612 (Step d). The resist 705 is removed and a protective coating 706 of Si$_3$N$_4$ or oxy-nitride (SiON) is formed over the top surface (Step e). Contact areas 771 are photolithographically defined by resist 715 over the nitride 706 (Step f). The nitride 706 is etched away beneath the resist openings (Step g). The resist is stripped away and a "lift-off" photo-resist layer 717 is formed over the top surface, except where the metal contacts will reside (Step h). Front metallization layer 719 is evaporated onto the resist contacting the exposed epi-layer surface aligned in the LED dot (Step i).

The resist 717 with metallization 719 is then removed using well-known photoresist stripper liquids, leaving metal contacts 719' remaining and applied to each dot 716 (Step j). These contacts extend over the nitride 716 to the edge of the chip (See FIG. 16) where individual bond pads are formed to address each dot 616'. Contact metallization 721 is then applied to the back of the substrate 612.

FIG. 17 illustrates an alternate dot definition method utilizing ion beam iraplantation. Steps a and b are as set forth in connection with FIG. 15. In step c, an implant mask of photoresist 705 is formed which defines regions 641 between LEDs which will be ion bombarded to implant protons 711 (Step d) to laterally isolate individual dots or pixels 616', separated by highly resistive bombarded regions 641' (See FIG. 17 notes). Next (Step e), a lift-off photoresist layer 715 is formed on the exposed top surface of epi-layers 716 with openings left where contact metallization 719 will be evaporated (Step f). The metallization is removed everywhere, except where desired, to form individual contacts 719' for each dot 616'. Contact metallization 721 is then applied to the backside (Step h).

FIG. 18 depicts an alternate dot definition process that does not require a separate deposit of a dielectric layer with associated photolithography, as in FIG. 15. Steps a-b are as above. In this alternate method, after defining the dot edges,(Step c), the cap or contact layer 616d is etched away (Step d). The exposed epilayer surface 616 is then anodized to form an insulating oxide 708, thus creating a dielectric in the proper pattern. This method, as in the method of FIG. 15, limits current spreading to the pixel area where it is desirable for uniform current injection. But, by removing the cap layer from regions between dots, illumination within the confines of each dot is maintained. Current spreading is further eliminated by growing an extremely thin upper cladding layer 616a, which will have very high lateral resistivity. Conventional cladding layers are 20 microns or higher. OMCVD enables fabrication of 0.5 micron, or less, layers with 0.2 micron being a preferred thickness for layer 16a.

The resist 705 is then removed (Step f) and a photoresist layer 715 formed, except where contacts are desired. Metal 719 is evaporated over and between the resist (Step h) and removed (Step leaving contacts 719' to each dot 616' The structure is then ready for back metallization 721, as previously described in connection with FIG. 15 (Step j).

In a variation of FIG. 18, the cap 616d and cladding layer 616a could both be anodized, eliminating the need for a cap etch step.

The above processes offer many advantages over other known systems of fabricating LEDs or LED bars. Some of these are the following:

Lattice-Matched System. The epitaxy process is very nearly perfectly lattice matched, since it is made in the GaAs/AiGaAs system rather than the GaAs/GaAsP system. Thus, compositional grading to achieve lattice matching is not required. The epi-layers are thin (less than 3 microns) as opposed to 20 to 30 microns in the GaAs/GaAsP system. Since the layers are thinner and are made by OMCVD, the layers yield much more uniform electroluminescence, making the LED bar more uniform. Since the epitaxial layers are lattice matched, it is also a simple matter to change the process to grow LEDs of any wavelength in the range of about 650 nm to 870 nm. The above processes can also utilize GaInP for the active epi layers and AIGaInP for the cladding layers. Another possible lattice matched system is GaInAsP/InP.

Better Confinement of Injected Carriers. The beneficial properties of AlGaAs layers can be used to enhance the optical output of the LED devices, in a manner similar to heterojunction lasers. The AlGaAs is used to reflect carriers so that they are confined to the volume In which the optical radiation is to be generated. This enables the generation of much higher efficiency and optical output than believed to be possible in the GaAs/GaAsP system.

Epitaxially-grown P/N Junction. The junctions are grown during the OMCVD process. In general, in GaAs/ GaAsP technology, the junction is diffused. The epitaxial junctions are of extremely high quality and can be placed anywhere in the structure-Diffused-zinc junctions used in GaAs/GaAsP have the following limitations: the zinc causes p-type doping, so the structure must be p-on-n (whereas epitaxial junctions can be p-on-n or n-on-p); the zinc concentration must be highest at the surface and must have a diffusion profile (whereas epitaxial doping can have any profile), the diffused Junctions are limited to zinc (whereas epitaxial structures can be zinc, or carbon, or other dopant as desired)Implant Isolation. In the FIG. 17 embodiment, the epitaxial wafers are implanted with protons to destroy the crystal quality of the regions between the dots. This isolation is used to prevent the current from spreading beyond the desired dot perimeter. (The GaAs/GaAsP technology uses patterned diffusion.) An additional advantage of implant isolation is that the surface becomes nonconducting so that the metallization can be placed directly-on the semiconductor, without dielectric insulators, and no short circuit will occur.

Use of GaAs Cap. A very thin layer 616d, about 10000A thick, of GaAs is provided on the top surface for three reasons: ease of contact, environmental stability, and improvement in current spreading. The GaAs is kept thin to allow most of the generated light to escape. If the cap is much thicker than 10000A, it will absorb a significant amount of light. Environmental stability is a factor because AlaAs can oxidize in air if left uncoated. The GaAs cap 16d provides the required coating.

By not removing all of the interpixel material, a path for lateral heat flow out of the pixel is preserved.

As shown in FIG. 19, the front and backside processed X-Y array 800 may be mounted directly to silicon wafer 823 in a precise location 810 with X and Y silicon driver circuits 820 and 822 formed in wafer 823 and coupled to the X and Y bonding pads 824 and 826, respectively. Bonding of array 800 to wafer 823 may also be accomplished by having the contact pads 826 replaced by cantilevered bars which extend over to pads on wafer 823 which can be trimmed to form circuit bonding pads.

Suitable silicon logic circuits 830 and interface circuits 832 are formed on wafer 823 to control which pixel 616 is illuminated in the X-Y matrix. Note that the driver circuits activate individual pixels by applying a positive voltage to a pixel in a top column, for example, pixel 1601 via bus bar 826a, while a negative voltage is applied to the same pixel 1601 via Y-driver 822 to bottom bus bar 824a, thus completing the current circuit through the LED 1601.

It should be noted that the substrate removal methods for fabrication of LED arrays include CLEFT, lift-off, and substrate etch-off. CLEFT and lift-off are appropriate if the substrate is to be reclaimed as a solid wafer. The etch-off process simply comprises the chemical dissolution of the substrate. Note that the substrate material may still be reclaimed in the etch-off process; however, it must be precipitated from the etch solution. The substrate can also be lapped off, as is conventionally done in the industry.

Also note that in the first step of the backside process, undesired epitaxial layers are removed; these layers are present to initiate the epitaxy, or may be buffer layers that are not needed in the final device. To make their removal simple, an AlAs etch stop layer (not shown) may be provided in the epitaxy between these layers and the epitaxial device structure. The layers can then be removed in etches that stop at AlAs, such as the well known PA etches. At a pH of about 8, these etches dissolve GaAs 1000 times faster than AlGaAs. After the etch stops at the AlAs, the AlAs can be removed in HF or HCl.

In the process described above, the backside of the substrate is provided with multiplex-compatible metallization to contact the back of each pixel. Note that this type of processing requires front-to-back alignment. The pixels are then separated by a mesa etch. Since the films are only about 5 microns thick, the mesa etch is straightforward and quick. The etching may be accomplished with either wet or dry processing. At this point, the exposed semiconductor may be coated with a dielectric to prevent oxidation.

Finally, the wafers are formed into individual dice. The dice 800 (See FIG. 19) are mounted in a pin grid array (PGA) or leadless chip carrier socket (neither shown). If the pixel count is sufficiently high (>1000), the X-Y drivers 820, 822 and logic multiplexing circuits 830 should be mounted within the chip carrier. The reason for this is that the wire count becomes excessive for high pixel numbers. The wire count is approximately the square root of the pixel count. Preferably, the array is mounted on the Si circuitry itself, and interconnected using thin film techniques and photolithographic processing. The circuit and array are then mounted in the leadless chip carrier or PGA.

As shown in FIG. 20, reflection from the back surface may be used to enhance emission. FIG. 20 is a perspective view of an LED array pixel showing the upper and lower cladding layers 616a and 616c with the active layer 616b between them. Thin contact layers 616d and 616e are formed on the front and back sides, respectively, and conductors 719a and b run orthogonal to each other on the contact layers. The back surface contact layer 616e of GaAs extends across the total pixel surface and serves as a back surface reflector. The back surface reflector reverses the light propagating toward the back of the pixel, so that it is directed toward the front surface. The back surface 16e may also serve to scatter light into the escape cone; which is a range of angles that rays, propagating within the LED crystal, must fall within for the ray to propagate beyond the semiconductor/air interface.

Tuning of individual epi-layers may also be provided to further improve LED efficiency. For example, assume a structure, such as the LED shown in FIG. 20, in which the epi-layers have the following properties:

| Layer | Refractive Index | Wavelength $\lambda/n$ (Å) | Composition AlGaAs |
|---|---|---|---|
| AIR | 1 | 6500 | N/A |
| 16d | 3.85 | 1688 | 0 |
| 16a | 3.24 | 2006 | 80% |
| 16b | 3.60 | 1806 | 38% |
| 16c | 3.24 | 2006 | 80% |
| 16e | N/A | N/A | Metal |

The active layer 16b, could be made "resonant" by making the active layer thickness a multiple of half the wavelength (i.e., a multiple of 903 Å). For example, an active layer thickness of 4510 Å or 5418 Å would be preferable to 5000 Å. Such a resonant structure could yield superluminescence or stimulated emission which would enhance the optical output. A benefit of stimulated emission in the resonant structure would be that all of the light thus generated would be in the escape cone.

The front (top) cladding layer 616a is set for maximum transmission (quarterwave or odd multiple). The quarterwave thickness is 503 Å, therefore the top layer should be 0.55 microns, or if better current spreading is needed, 1.05 microns.

The back cladding layer can be tuned for maximum reflection by using even multiples of 503 Å, such as 10×503 or 5030 Å.

Optional front and back Bragg reflector layers 616f and 616g, respectively, may be incorporated into the device of FIG. 20 during OMCVD growth, thereby converting the LED into a vertical cavity laser. The laser cavity is bounded by the Bragg reflectors 616f and 616g and the emitted light will be phase coherent. The Bragg reflectors are formed by alternating many $Al_xGaAs/Al_zGaAs$ layers. A sufficient number of layers will yield a high reflection coefficient. The electrical cavity is formed by the AlGaAs cladding layers. Thus, vertical cavity lasers can be in an X-Y array, or may be formed in a laser bar. The feature that makes this possible is the double-sided processing approach, which permits a wide range of pixel structures, including LEDs, lasers and detectors.

A light detector array 945 can be formed in a similar manner. To form a light detector array, the epitaxial films are doped so as to form a p-i-n structure, rather than an LED. The active layer comprises a semiconductor chosen for absorption over the wavelength range of interest. For example, long wavelength detection could utilize InAs grown on an InAs substrate. Alternatively, InGaAs grown on InP or GaAs could be utilized for mid-IR detection. Near IR is detected with GaAs or AlGaAs. The fabrication of the detector must include edge passivation to maintain minimal dark current, but is otherwise the same as the LED array processing previously described.

The multiplexing electronic detector circuitry is somewhat different than the LED driver circuit, since it must sense the current generated in each pixel in sequence, rather than supply current. The electronics is nevertheless straightforward, and is similar to charge coupled device (CCD) circuitry. In fact, the device could be formed using a CCD array instead of a p-i-n array.

An infrared-to-visible digital image converter can be formed from a detector 950 and light emitting diode array 800 (as shown in FIG. 22). The converter is useful for night vision devices, as well as for digital processing of IR and visible video data.

Current image converters utilize a photocathode based system that converts IR radiation to visible. The conversion process is a direct analog process. Owing to this design, the direct analog process is not particularly amenable to digital image enhancement. There are also various displays that could be superimposed over the night vision display to provide the user with communication or computer data. However, the photocathode display is not easily adaptable to display applications.

A digital pixel-based system, in accordance with FIGS. 21 and 22, functions both as an IR image converter, an image enhancing device, and a display.

The converter invention consists of three main elements' the IR detector array 950, the multiplexing electronics 970, and the light emitting diode (LED) array 800. A diagram of the IR image converter is shown in FIG. 22. An IR image is focused by lens 946 on a multiplexed X-Y array 950 of IR detectors. The pixel data from the detectors is processed by the electronics 970, which then drives a synchronous multiplexed LED array 800. Note that the processor can accept external data via data port 972 to add to or subtract from the image. In this way, image enhancement can be accomplished, or communications or other data can be superimposed on the display 800.

As noted above, the detector array 950 can comprise a Si charge coupled device, or if longer wavelength detection is required, can be made from p-i-n diodes formed from material in the InGaAs system. The array 950 is fabricated using substrate etch-off or lift-off processing. along with backside processing. to form very thin structures with metallization on both sides, as more fully described above in connection with the LED array 800.

The intensity of the image produced by array 300 may be controlled by varying the duty cycle timing or modulating the drive current of the LED pixels.

The electronics 970 consists of a multiplexing and sequencing circuit that first detects the charge or current in each IR detector and then couples this input data to a current amplifier that drives the corresponding LED pixel in the output array 800. The electronic processor 970 also accepts signals from an external source, such as a microprocessor that can be displayed on the LED array. Moreover, the electronics can supply that video data to the microprocessor for image enhancement and can accept a return signal to be displayed on the LED array 300.

The LED array consists of multiplexed thin film LED pixels formed from material in the AlGaInP' family, and more particularly, AlGaAs for bright red displays. The array is formed using the previously described processing array steps. The pixel size can be as small as 25 microns square and, consequently, the display can offer extremely high resolution or alternatively, fairly low cost.

As shown in FIG. 23, the detector 950 and LED array 800 can be stacked into a hybrid assembly comprised of a top thin film IR X-Y detector array 950 affixed by light transparent glue to lower thin film LED array 800 mounted on glass substrate 620. A glass lens 960 is affixed to the top surface of detector 950 and heat transfer openings 960 provided as necessary for cooling purposes. The entire structure can be quite thin (1 mil), with the electronics 970 provided around the periphery. Ultimately, the monolithic thin array can be mounted on ordinary glasses for image enhancement of visible light, as well as for display of data superimposed on video images.

The applications of the device of FIGS. 21–23 include military night vision systems, range finders, advanced military avionics, personal communications systems, and medical systems In which real-time image enhancement is useful.

As shown schematically in FIGS. 24 and 25, X-Y arrays can also be used to form a multicolor display. To make such a display, individual X-Y arrays labelled LED1, LED2 and LED3, are formed from two or more different epitaxial structures. The primary difference in the structure is in the active layer material 761, 762 and 763. which must have different band gaps to create different colors. For example, red 763 can be created with AlGaAs, and green 762 can be created with InAiGaP. The top device LED1 may be a blue LED formed of II–VI material, such as ZnSe, ZnSSe or a group IV alloy such as SiC.

The arrays must be stacked with the larger bandgap LED1 closer to the observer. The material with the larger bandgap will be transparent to the radiation from the smaller bandgap. Thus, in this way, the observer will be able to see both colors.

The creation of the stack of three LEDs is as follows: First, the three separate LED arrays LED1, LED2 and LED3 are formed, as previously described. Next, they are stacked together with glass 600 between them.

Transparent glue or epoxy 900 is used to bond the stacks on top of each other. The upper and lower bonding pads P1 and P2 on each LED are laterally staggered with respect to other LEDs, so that individual LED pixels may be addressed (See plan view FIG. 25).

Several points need to be emphasized regarding the formation of the integrated detector array 414 and display 412. First, the matrix metallization (not shown) of the detector must be positioned over the metallization of the display. In this way, no decrease in the optical aperture of the display is introduced by the metal interconnects of the detector array 414. Second, the detector pixels 462 can be made as small as a few microns square provided the detector sensitivity is high enough. Since the TFT's are also in the order of a few microns wide, detector pixels of such size would not block light. Third, the detector array 414 does not need to use an active matrix, because III–V materials, such as, GaAs and AlGaAs are extremely fast detectors (<1 $\mu$s decay time) and so the detector array can be scanned as fast or faster than the display. Since the detector pixels are small, they can be placed over the transistors in the active matrix display, resulting in very little reduction in optical aperture of the display.

The integrated eyetracker device 500 can consist of a pair of units that can be simultaneously scanned by computer 418 to obtain real time correlation between the probe or cursor signal and the detected LOS signal. This real-time signal correlation can be used to eliminate the complicated image processing software that is ordinarily needed to analyze a CCD dark pupil image.

The line-of-sight information obtained may be processed in computer 418 and coupled to control device 420 along line 422 to execute functions, or to display 412 along line 424 to present various images or for generating a high resolution image only in the line-of-sight vicinity.

The detector array may alternatively be mounted on the back panel of the display 412 or preferably integrated with the formation of the display array. In this integrated embodiment, the detector pixels are formed of Si on the TFT substrate in the same process in which the TFT's are formed. Each detector pixel is located adjacent a corresponding TFT pixel.

Figure 27A:
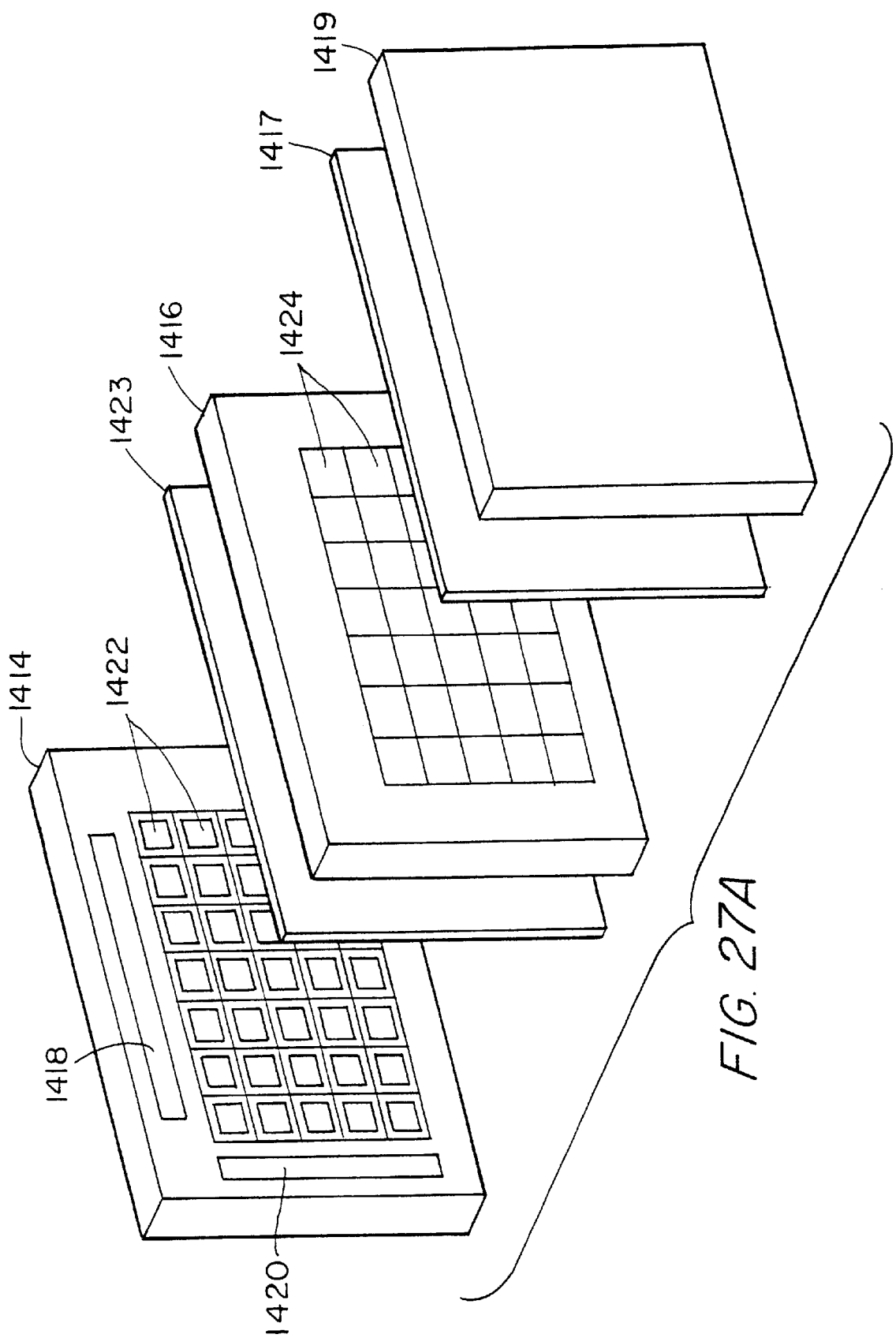
FIG. 27A is an exploded perspective view of an electroluminescent panel display in accordance with the present invention.

The display array may be comprised of an EL panel. As stated previously, other preferred embodiments employ an emissive material such as an electroluminescent film, light emitting diodes, porous silicon or any light emitting material to form each pixel element of the display. To that end, another preferred embodiment of the present invention is illustrated in the perspective view of an electroluminescent (EL) panel display in FIG. 27A. The basic components of the EL display include an active matrix circuit panel 1414, a bottom insulator 1423, an electroluminescent structure 1416, a top insulator 1417 and an optically transparent electrode 1419, which are secured in a layered structure. The EL structure 1416 is positioned between the two planar insulating layers 1417 and 1423 which prevent destructive electrical breakdown by capacitively limiting direct current flow through the EL structure and also serve to enhance reliability. The insulators 1417 and 1423 have high electrical breakdown so that they can remain useful at high fields which are required to create hot electrons in the EL phosphor layers. The capacitive structure of the display is completed by producing thin-film electrodes adjacent to each insulator. One of these electrodes is formed within the pixel array 1422 and the other electrode is the optically transparent electrode 1419 which allows light to exit the display.

The array of pixels 1422 formed on the circuit panel 1414 are individually actuated by a drive circuit. The circuit has first 1418 and second 1420 circuit components that are positioned adjacent to the array such that each pixel 1422 can produce an electric field in the electroluminescent structure 1416 between the pixel electrode and an element of the electrode 1419. The electric field causes an EL element 1424 to be illuminated.

Figure 27B:
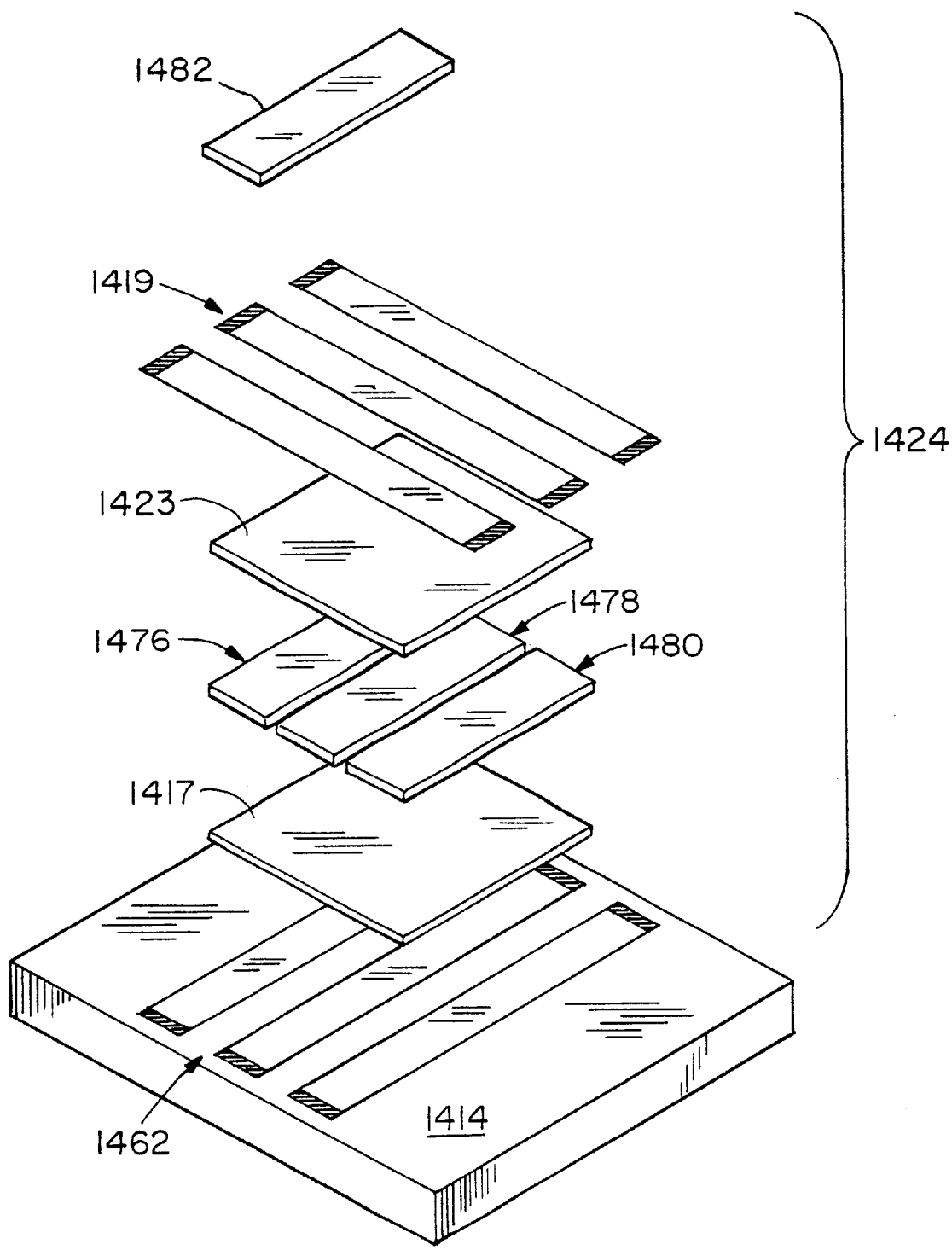
FIG. 27B is a perspective view of an electroluminescent color display element.

The electroluminescent structure 1416 may be formed of a single phosphor layer for a preferred embodiment having a monochrome EL display. In another preferred embodiment, the EL structure 1416 is formed of a plurality of patterned phosphor layers for providing color display. The phosphor layers are patterned such that each color pixel includes red, green and blue phosphor elements. The EL color display can be formed based on the EL display formation process disclosed in international application PCT/US88/01680 to Barrow et al. Referring to FIG. 27B, each EL element 1424 is divided into single color elements such as red 1476 and 1482, green 1478 and blue 1480.

To illuminate a single color element for a given EL element 1424, the drive circuit causes an electric field to be formed between one of the bottom electrodes 1462 and the transparent electrode 1419. For a selected illuminated single color element, the light emitting centers of the phosphor are impact excited by the flow of hot electrons through the phosphor layer when the electric field exceeds a known threshold. As such, the pixels 1422 can be selectively actuated to provide any illuminated color for that pixel group.

The active matrix pixel array employs transistors (TFTs) colocated with each pixel in the display to control the function of the pixel. As applied to EL displays, the active matrix approach offers significant advantages including reduced power dissipation in the circuit panel and increased frequency at which the AC resonant driver can operate. The formation of a useful EL active matrix requires TFTs that can operate at high voltages and high speeds. Single crystal silicon is preferred for achieving high resolution in a small (6 in× 6 in or less) active matrix EL display.

In an EL display, one or more pixels are energized by alternating current (AC) which is provided to each pixel by row and column interconnects connected to the drive circuitry. The efficient conduction of AC by the interconnects is limited by parasitic capacitance. The use of an active matrix, however, provides a large reduction of the interconnect capacitance and can enable the use of high frequency AC to obtain more efficient electroluminescence in the pixel phosphor and increased brightness. In accordance with the present invention, the TFTs that provide this advantage are formed in a single crystal wafer, such as bulk Si wafers, or thin-films of single crystal or essentially single crystal silicon. These high quality TFTs are employed in an EL panel display, providing high speed and low leakage as well as supporting the high voltage levels needed for electroluminescence.

In preferred embodiments, single crystal silicon formed on an insulator (SOI) is processed to permit the formation of high voltage circuitry necessary to drive the EL display. More specifically, thin-film single crystal silicon formed by the ISE process or other SOI processes allows for fabrication of high voltage DMOS circuitry for the TFTs as well as low voltage CMOS circuitry for the drivers and other logic elements.

Figure 27C:
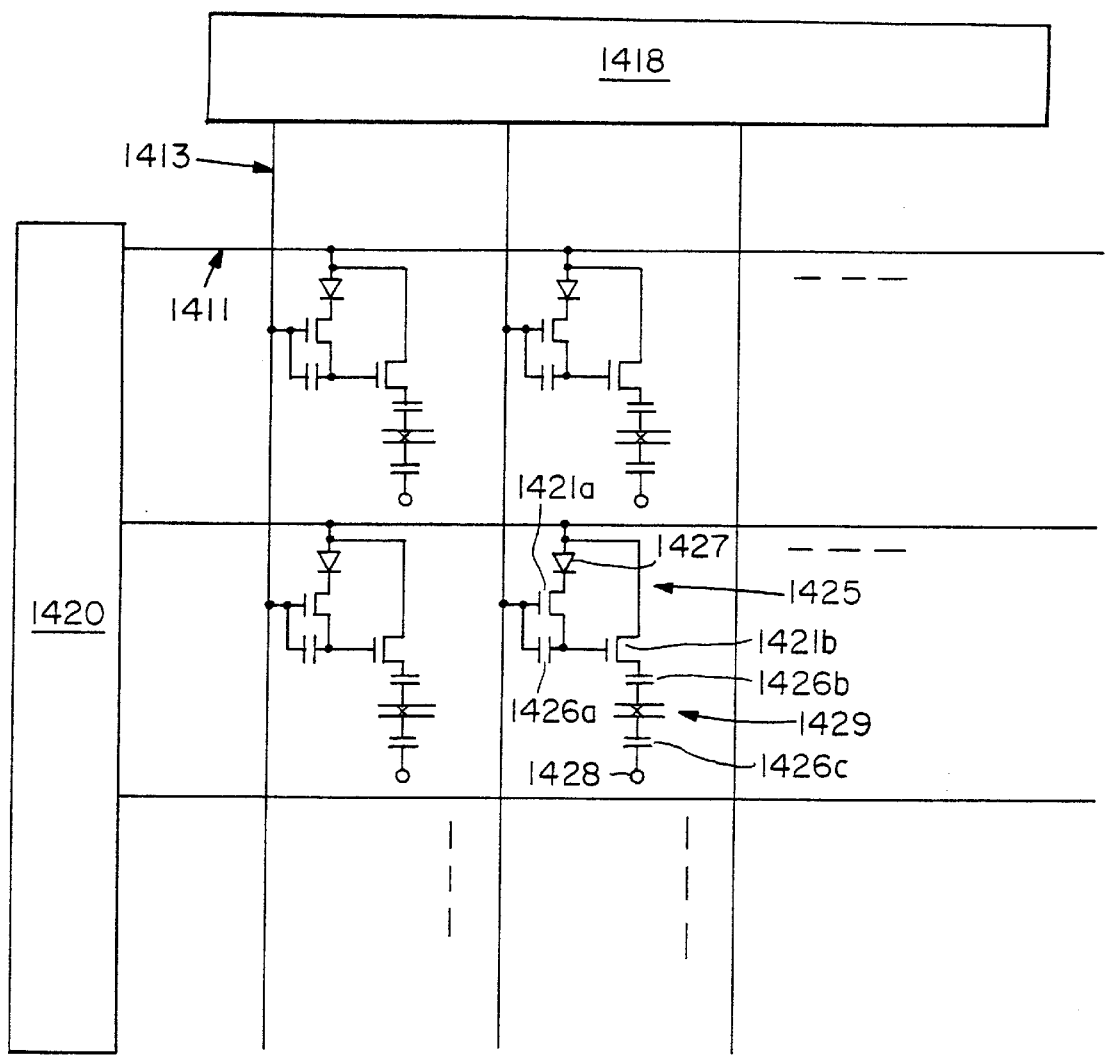
FIG. 27C is a circuit-diagram illustrating the driver system for the electroluminescent panel display.
Figure 27D:
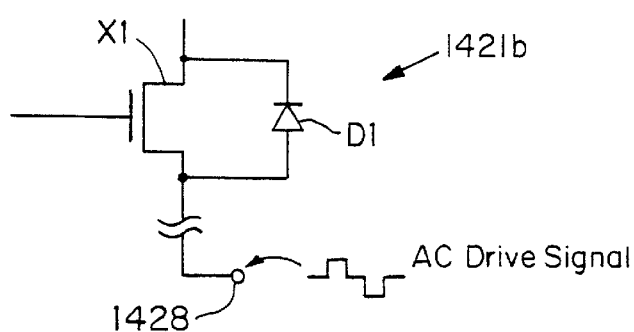
FIG. 27D is an equivalent circuit for a DMOS transistor of FIG. 16C.

The DMOS/CMOS drive circuitry configuration for controlling an EL monochrome display is illustrated in FIGS. 27C–27D. Each active matrix EL pixel circuit 1425 includes a CMOS and DMOS transistor (TFTs) 1421*a* and 1421*b* respectively. The capacitors 1426*a*, 1426*b* and 1426*c* represent the parasitic and blocking capacitors normally present in an AC EL structure. Despite its complicated appearance, each pixel circuit 1425 should actually occupy only a small fraction of the pixel area even with array densities of up to 1000 lines/inch. The drive circuitry for an EL monochrome display is shown for simplicity purposes only. For an EL color display, the drive circuitry for each pixel would comprise three pixel circuits 1425 selectively activated to drive the red, green or blue color elements.

Referring to FIG. 27C, there are two unique aspects of the pixel circuit 1425. The first is that the use of the DMOS transistor 1421*b* on the output of the drive circuit allows the EL display to be driven with an AC drive signal at 1428. This feature can be appreciated by considering just the DMOS transistor.

Referring to FIG. 27D, an equivalent circuit for a DMOS transistor 1421*b* includes an NMOS device Xi with a shunting diode D1. If the gate on the NMOS transistor Xi is raised to the threshold voltage above the source, current will flow through the transistor XI during the positive AC drive pulse. The presence of the shunt diode DI allows current to flow in the reverse direction regardless of the gate voltage, so that with a high gate voltage, current flows through the transistor Xi during both the positive and negative transitions. The EL layer 1429 is therefore being excited and will be illuminated as long as the gate is held high. If the gate is held low, that is at a voltage below the threshold voltage $V_t$, then the transistor X1 will not conduct during the positive drive pulse. Thus, the EL layer 1429 will only see a series of negative pulse and will charge to the pulse potential during the first negative pulses and be prevented from discharging during the positive pulse by the rectifying behavior of the diode D1. Therefore, after a single brief illumination period, the EL layer 1429 will remain passive since the total voltage across it and its isolation capacitors 1426*b* and 1426*c* remains constant.

Referring back to FIG. 27C, the second unique feature of the circuit 1425 is that it can be controlled by only two wires. The second feature is achieved in the present invention through the use of a p-channel MOS transistor 1421*a*, and a diode 1427. The diode 1427 may be fabricated as a lateral or vertical structure and would not add significantly to the overall area or complexity. The diode 1427 is needed because the NMOS transistor 1421*a* is a symmetric device and would otherwise discharge the capacitor 1426*a* during the illuminate period rendering the circuit and display inoperable.

To insure the performance of the circuit 1425, a circuit analysis was performed. The circuit 1425 operates by first charging the capacitors 1426*a* by applying a low signal to the select line 1413 (0 volts) in the analysis and then raising the data line 1411 to the desired voltage (in a range from 0.5 to 2 volts in this analysis). After the charging sequence, the capacitor 1426*a* will be charged to a voltage approximately equal to the difference between the data and select line signal levels and minus the diode 1427 forward voltage drop. To turn on the output transistor 1421*b*, the select line 1413 is first increased to about 1 volt and the data line 1411 is ramped from −2 volts to 0 volts. The output transistor 1421*b* remains on for a time which is directly proportional to the voltage that was stored on the capacitor 1426*a*. In this way, grey scale is achieved by the circuit 1425.

A preferred EL display formation process includes the formation of a single crystal silicon film, fabrication of active matrix circuitry on the silicon film and integration of EL materials to form the emissive elements. To that end, FIGS. 28A–28K illustrate the Isolated Silicon Epitaxy (ISE) process to form a silicon-on-insulator (SOI) film as well as a process for fabricating high voltage DMOS devices and low voltage CMOS devices on the ISE film to form circuit panel circuitry. Note that while the ISE process is shown herein, any number of techniques can be employed to provide a thin-film of single crystal Si.

Figure 28A:
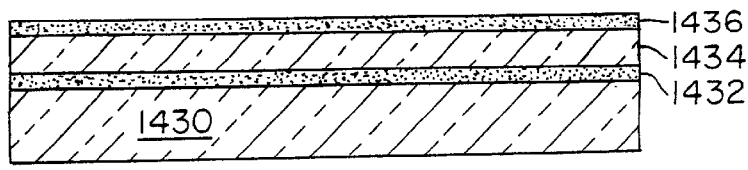
FIGS. 28A–28L is a preferred process flow sequency illustrating the fabrication of a circuit panel for an electroluminescent panel display.

An SOI structure, such as that shown in FIG. 28A, includes a substrate 1430 and an oxide 1432 (such as, for example $SiO_2$) that is grown or deposited on the substrate 1430. A polycrystalline silicon film is deposited on the oxide 1432, and the poly-Si film is capped with a capping layer 1436 (such as for example, $SiO_2$). The structure is the heated near melting point, and a thin movable strip heater (FIG. 6) is scanned above the top surface of the wafer. The heater melts and recrystallizes the silicon film that is trapped between the oxide layers, resulting in a full area single crystal silicon film 1434.

A thin single crystal layer of silicon 434 is thus formed over the oxide 1432 such that the oxide (or insulator) is buried beneath the Si surface layer. For the case of ISE SOI structures, after the capping layer is removed, the top layer is essentially single-crystal recrystallized silicon, from which CMOS circuits can be fabricated. The use of a buried insulator provides devices having higher speeds than can be obtained in conventional bulk material. Circuits containing in excess of 1.5 million CMOS transistors have been successfully fabricated in ISE material.

Figure 28B:
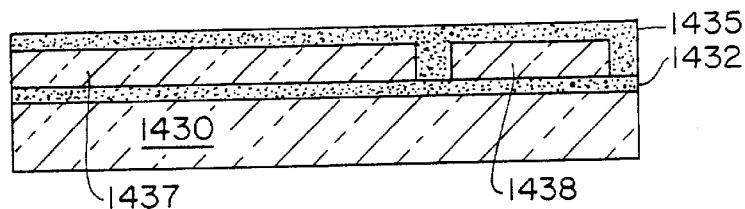
Figure 28C:
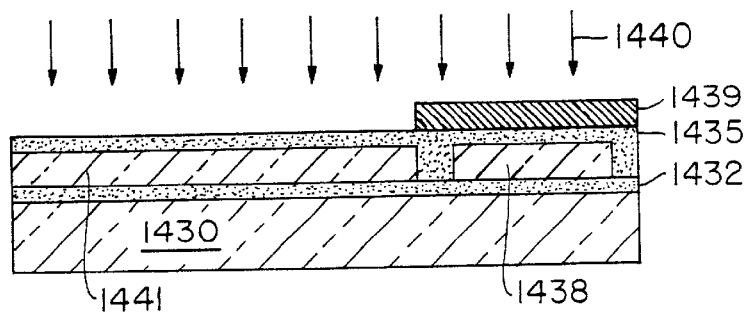
Figure 28D:
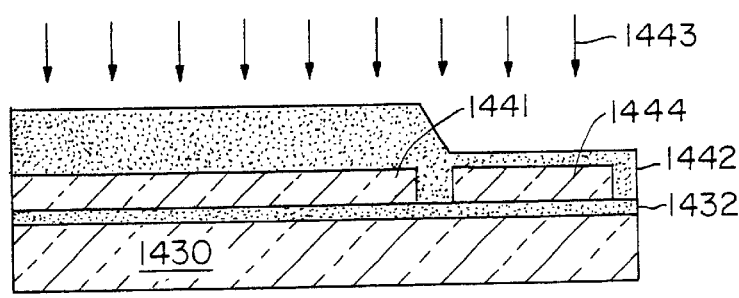

As shown in FIG. 28B, the silicon film 1434 is patterned to define discrete islands 1437 and 1438 for each pixel. An oxide layer 1435 is then formed over the patterned regions including channels 1448 between the islands 1437 and 1438. A twin well diffusion process is then employed to form both p and n wells. To form n wells, silicon nitride islands 1439 are formed to isolate those islands 1438 designated to be p wells (FIG. 17C). The remaining islands 1437 are subsequently implanted with an n-type dopant 1440 to form n wells 1441. To form p wells, a thick oxide layer 1442 is grown over the n wells to isolate those islands from the p-type dopant 1443, and the silicon nitride islands are removed (FIG. 28D). The non-isolated islands are then implanted with the p-type dopant 443 to form p wells 1444.

Figure 28E:
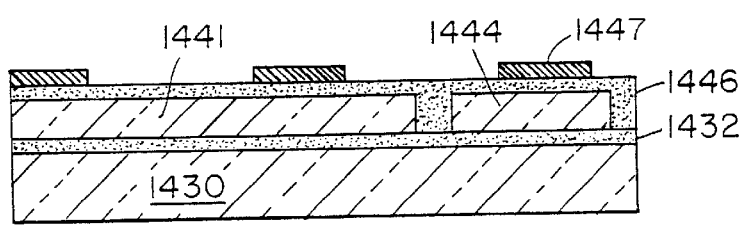
Figure 28F:
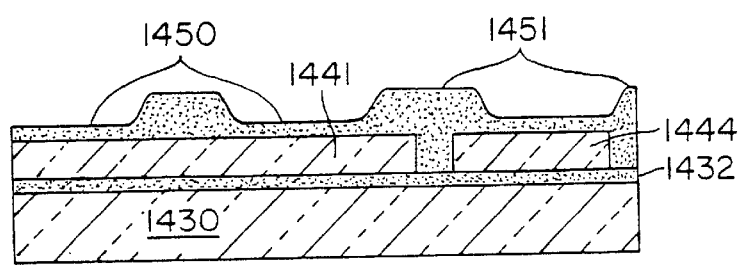
Figure 28G:
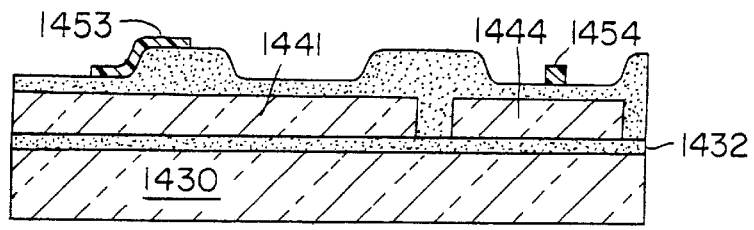

Following the twin well formation, a thick oxide film is grown over the surface of the silicon islands 1441 and 1444 to form active area regions. More specifically, the oxide layer 1446 is etched to a relatively even thickness and silicon nitride islands 1447 are deposited thereon (FIG. 28E). Next, a thick oxide film is grown around the surface of the silicon islands 1441 and 1444 to form active area regions 1450 between the thick LOCOS field oxide regions 1451 (FIG. 28F). Polysilicon is then deposited and patterned to form the gates 1453 of the high voltage DMOS devices and the gates 1454 of the low voltage CMOS devices (FIG. 28G). Note that the gate 1453 of the DMOS device extends from the active area region 1450 over the field oxide region 1451. The edge of the gate 1453 which is over the active region 1450 is used as a diffusion edge for the p-channel diffusion, while the portion of the gate which is over the field oxide region 1451 is used to control the electric field in the n well drift region.

Figure 28H:
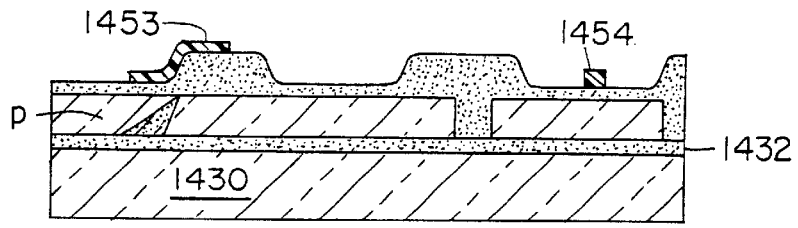
Figure 28I:
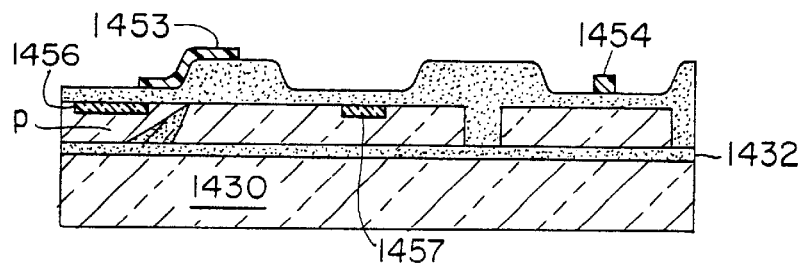
Figure 28J:
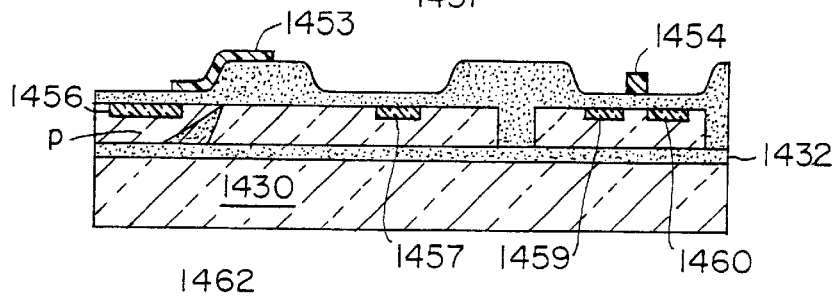
Figure 28K:
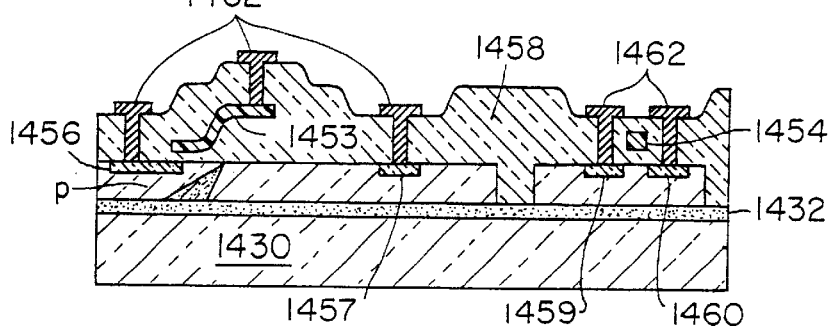

Following the channel diffusion, the n-channel and p-channel source 1456, 1459 and drain regions 1457, 1460 are formed using arsenic and boron implantation (FIGS. 28H–28J). Next, a borophosphorosilicate glass (BPSG) flow layer 1458 is formed and openings are formed through the BPSG layer 1458 to contact the source 1456, the drain 1457 and the gate 1453 of the DMOS device as well as the source 1459 and the drain 1460 of the CMOS device (FIG. 28K). Further, a patterned metallization 1462 of aluminum, tungsten or other suitable metal is used to connect the devices to other circuit panel components. The preferred process comprises nine masks and permits fabrication of both high voltage DMOS and low voltage CMOS devices.

Figure 28L:
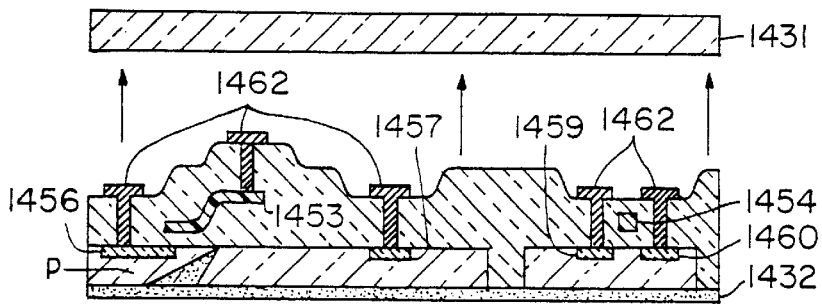

The high voltage characteristics of the DMOS devices depend on several dimensions of the structure as well as the doping concentrations of both the diffused p-channel and n-well drift region. The important physical dimensions are the length of the n-well drift region, the spacing between the edge of the polysilicon gate in the active region and the edge of the underlying field oxide, and the amount of overlap between the polysilicon gate over the field oxide and the edge of the field oxide. The degree of current handling in the DMOS devices is also a function of some of these parameters as well as a function of the overall size of the device. Since a preferred embodiment includes a high density array (1 M pixels/in$^2$), the pixel area, and hence the transistor size, is kept as small as possible. Referring to FIG. 28L, the circuit panel can optionally be removed from the substrate 1430 and transferred to a glass plate 1431 upon which EL phosphors have been formed. The removal process can comprise CEL, CLEFT or back etching and/or lapping.

FIGS. 28A–29D illustrate the details of the fabrication process of an electroluminescent color display. As stated earlier, this fabrication process is based on the EL color display formation process disclosed in international application PCT/US88 01680 to Barrows et al. The EL display formation process, whether for a monochrome or color display, comprises the sequential deposition of layers of an emissive thin-film stack. The phosphor layers are patterned such that each color pixel includes red, green and blue phosphor elements. The red color is obtained by filtering a yellow ZnS:Mn phosphor layer so as to only select the red component. The green and blue phosphor elements have components other than Mn for emitting in the desired spectral regions.

Figure 29A:
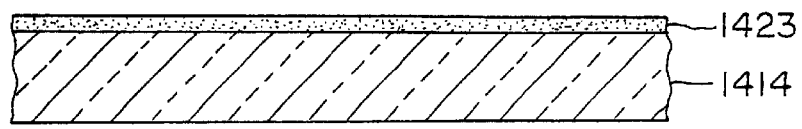
FIGS. 29A–29D is preferred process flow sequence illustrating the fabrication of an electroluminescent color display.
Figure 29B:
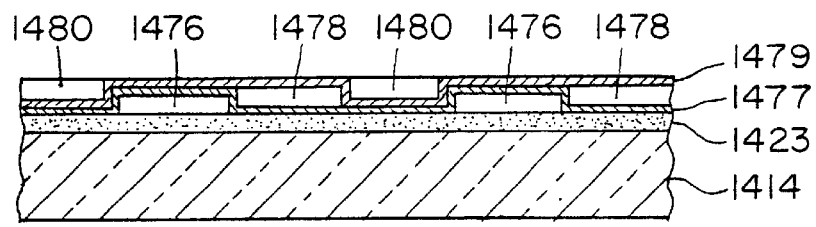

The first layer of the EL display is the bottom electrode. In a preferred EL display formation process, the bottom electrode comprises the source or drain metallization of the transistor in the drive circuit. This electrode may be optimized for high reflection of the desired wavelength to increase the luminous efficiency of the EL panel. Referring to FIG. 29A, the fabrication process begins with the deposition of the bottom insulator 1423, preferably covering the entire surface of the active matrix of the circuit panel 1414. The first color phosphor layer 1476 is then deposited onto the active matrix and patterned. A first etch stop layer 1477 is deposited, and a second color phosphor layer 1478 is deposited and patterned over the stop layer (FIG. 28B). A second etch stop layer 1479 is deposited, and a third color phosphor layer 1480 is deposited and patterned over the second stop layer.

Figure 29C:
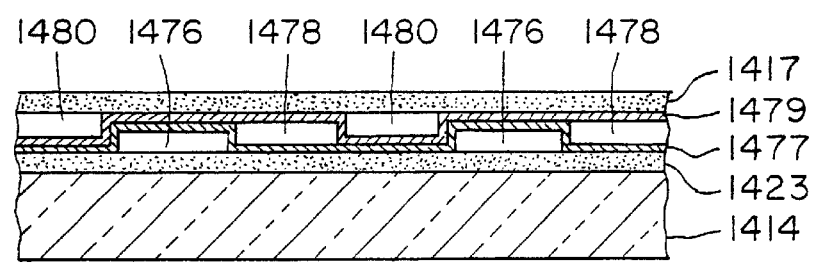
Figure 29D:
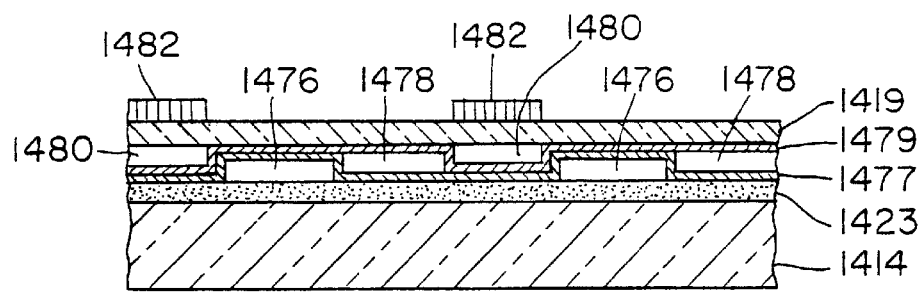

Referring to FIG. 29C, the array of patterned phosphor layers 1416 is then coated with the top insulator 1417. The two insulating layers 1417 and 1423 are then patterned to expose the connection points between the top electrodes and the active matrix circuit panel, and also to remove material from areas which external connections will be made to the drive logic. The top electrode 1419 formed of an optically transparent material such as indium tin oxide is then deposited and patterned over the top insulator 1417 (FIG. 29D). The deposition of the top electrode serves to complete the circuit between the phosphors 1416 and the active matrix circuitry 1414. A red filter 1482 is then deposited and patterned over the red pixels, or alternatively is incorporated on a seal cover plate if a cover is used. The red filter 1482 transmits the desired red portion of the ZnS:Mn phosphor (yellow) output to produce the desired red color.

Alternatively, the EL thin-film stack may be formed on a glass or other substrate to which the active matrix circuit panel is transferred by the aforementioned transfer processes. Yet another option comprises the transfer of both the circuit panel and the EL stack to another material such as a curved surface of a helmet-mounted visor. In a single-step transfer, the circuit is transferred to a flexible substrate. The flexible substrate is then bent to form a curved display. In a double-step transfer, the circuit is first bent to form a curved circuit and double transferred to a fixed curvature substrate. The curved direct view display makes use of the intrinsic stress on the silicon. The curved surface releases the stress on the circuit and may improve circuit performance.

Figure 30A:
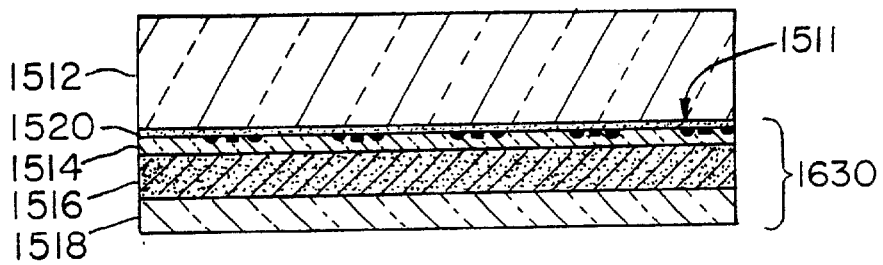
FIGS. 30A–30B is a preferred process flow sequence illustrating transfer and bonding of an SOI structure to a superstrate and removal of the substrate.
Figure 30B:
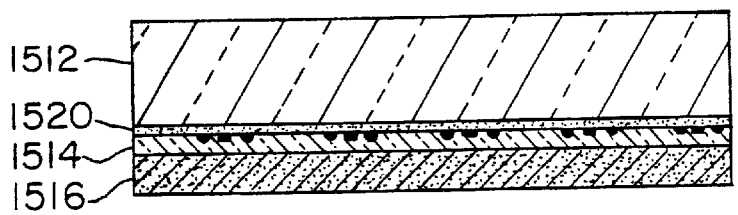

A preferred process for transferring and adhering thin-films of silicon from its support substrate to a different material is illustrated in FIGS. 30A–30B. This process may be employed for transferring a circuit panel formed in thin-film silicon (FIGS. 28A–28L) or an entire EL display (FIGS. 29A–29D) and adhering it to a different material such as glass or a curved surface of a material.

Referring to FIG. 30A, the starting structure is a silicon wafer 1500 upon which an oxide layer 1516 an a thin film of single crystal silicon 1514 is formed using any of the previously described techniques, such as ISE or CLEFT. A plurality of circuits 1511 such as pixel electrodes, TFTs, drivers and logic circuits are then formed in the thin-film silicon 1514. The SOI processed wafer is then attached to a superstrate 1512, such as glass or other transparent insulator or a curved surface of a material, using an adhesive 1520.

The wafer is then cleaned and the native oxide is etched off the back surface 1518. The wafer is put into a solution. The etchant has a very low etch rate on oxide, so that as the substrate is etched away and the buried oxide is exposed, the etching rate goes down. The selectivity of the silicon etch rate versus the oxide etch rate can be very high (200:1). This selectivity, combined with the uniformity of the silicon etching, allows the etcher to observe the process and to stop in the buried oxide layer 1516' without punching through to the thin silicon layer 1514 above it. Wafers up to 25 mils thick and oxides as thin as 4000 Å have been successfully etched using this process. One such etchant is hydrazine.

The thin film 514 transferred to the glass 1512 is now rinsed and dried. If not already provided with the circuitry 1511, it can be backside circuit processed. Also, if desired, the film can be transferred to another substrate and the glass superstrate can be etched off, allowing access to the front side of the wafer for further circuit processing.

Figure 31A:
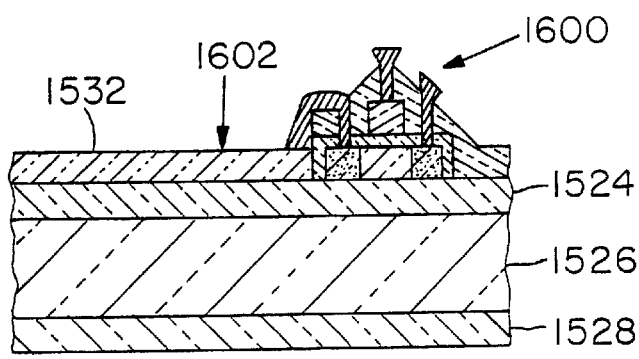
FIGS. 31A–31B is a preferred process flow sequence illustrating an alternative transfer process in which a GeSi alloy is used as an intermediate etch stop layer.
Figure 31B:
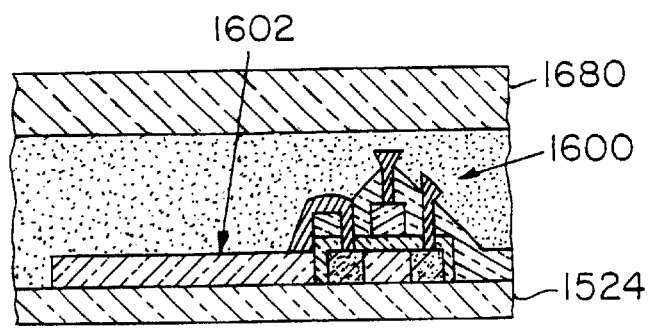

FIGS. 31A–31B illustrate an alternative silicon thin-film transfer process in which GeSi is used as an intermediate etch stop layer. Referring to FIG. 31A, in this process, a silicon buffer layer 1526 is formed on a single crystal silicon substrate 1528 followed by a thin GeSi layer 1524 and a thin single crystal silicon device or circuit layer 1532; using well-known CVD or MBE growth systems.

The layer 1532 is then IC processed in a manner previously described to form circuits such as TFTs 1600 or pixel electrodes 1602. Next, the processed wafer is mounted on a glass or other support 1680 using an epoxy adhesive. The epoxy fills in the voids formed by the previous processing and adheres the front face to the superstrate 1680.

Next, the original silicon substrate 1528 and the silicon buffer 1526 are removed by etching with KOH, which does not affect the GeSi layer 1524 (FIG. 31B). Finally, the GeSi layer 1524 is selectively etched away which does not affect the silicon film 1522.

In this case, the detector array would be transferred to the EL panel 1419.

The eye tracking device of the invention offers numerous system simplifications. One simplification is made possible by the use of the high speed III–V detector array 414. Scanning of the array can be synchronized with the display scan. This eliminates the complex software needed for pattern recognition in the typical CCD approach. This is because the reflected light can be analyzed pixel-by-pixel in real time to determine the area on which the viewer is focusing. Moreover, depending on the angular resolution needed, it may be possible to replace the detector matrix array with a much simpler array of pixels interconnected in a common parallel circuit, as shown in FIG. 12 comprising anode plane 482 and cathode plane 480. Only two terminals are used for connection to the detector plane 482. Light reflection from the non-macular portion of the retina largely falls beyond the detector array 414 and macular reflection returns to some location on the array 414. The display 413 is scanned row by row while the computer simultaneously monitors the reflected signal at the detector. The row yielding the highest signal is the row upon which the viewer is focused. A similar scan is performed for the columns to determine the column pixels upon which the viewer is focused.

Figure 26:
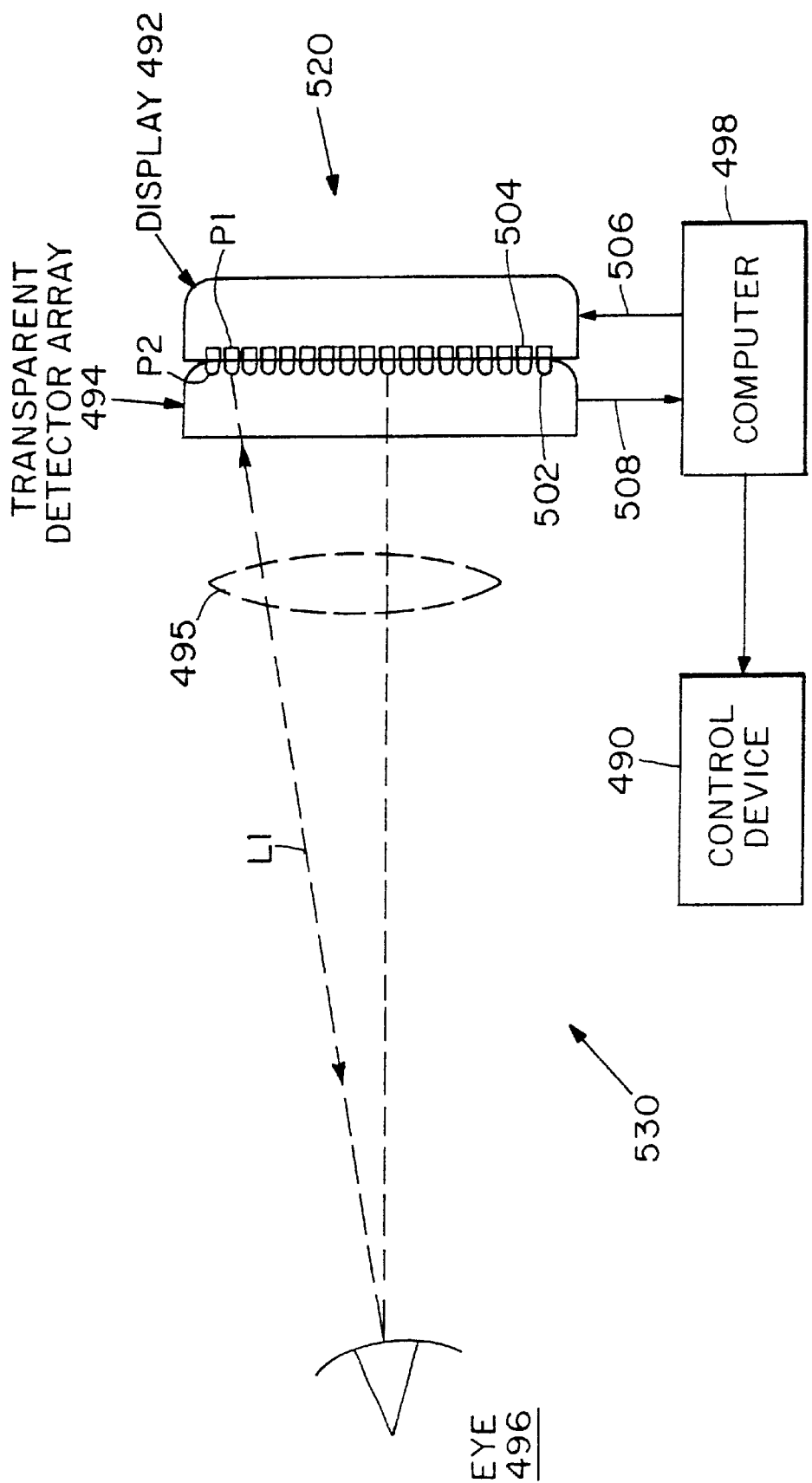
FIG. 26 is a schematic diagram of an alternate embodiment of an eye tracking device of the invention.

Referring now to the schematic diagram of FIG. 26, an alternate embodiment of the present invention will now be described. This embodiment relates to a direct viewing eye tracking system 530 that combines a flat panel display device 492 with a substantially transparent array of optical detectors 494 to form an eye tracker device 520. As in FIG. 9, flat panel display device 492 is used as a monolithic substrate for the detector array and as a light source for determining the position of the eye 496. The detector array 494 and display 492 are preferably formed as described above. The array is aligned and transferred onto the active matrix electronics of the flat panel display 492. A test pattern and software in computer 498 analyzes the sensed data generated by the individual detectors 502 of the array 494 and determines the position of the eye based upon which detector(s) senses light reflected from the eye.

Light from display 492 is used to project an image for viewing by the eye(s) 492 of a viewer. The image to be displayed is generated in computer 498 and is coupled as an electrical input video signal to display 492 along line 506. Image light rays from display 492 pass through detector array 494 and are viewed by the eye 496.

A light ray emanating from a particular pixel P1 of display 492 is shown as line L1. This ray impinges on the fovea of the eye 496 and is reflected back along line L1. The ray returns to the display 492 in the vicinity of the original pixel because reflection from the fovea is approximately normal to the retina and therefore nearly axial. Non-axial rays which impinge on the retina beyond the fovea will not be reflected back along the axial optical path.

Once the axial ray L1 returns to the display 492, the detector array 494 identifies the portion of the array at which the axial ray returns by generating a voltage signal from a detector pixel P2 located in the array nearest the returned ray. That portion of the array is, of course, the part of the display focussed upon by the eye 496 of the user. This voltage signal, indicative of eye position, is coupled on line 508 to computer 498. A test pattern from computer 98 is then generated by computer 418 and interlaced with the display image to indicate to the user the eye's position. Software, in computer 418, provides a test pattern in the form of cursor image on display 492 which is formed at the line-of-sight location. The cursor is interlaced to provide constant feedback to the detector array 494. The interlace frequency can be adjusted to make the cursor visible or not visible to the user. An optional lens system 495 may be employed between the eye and array to enhance the image projected from the display 492. The line-of-sight information obtained in array 494 may be processed in computer 498 and coupled to control device 490 to execute functions or may be coupled to present various images, such as, the previously mentioned cursor.

V. Optics For Head-Mounted System

Figure 32:
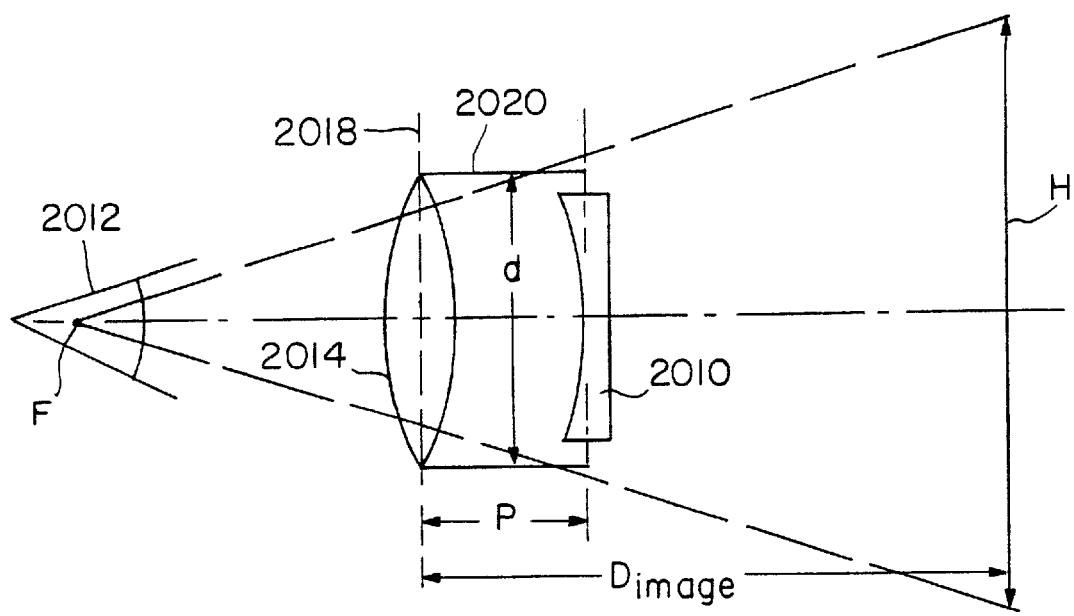
FIG. 32 shows a schematic illustration of a head mounted display system.

A preferred embodiment of the invention is illustrated in the direct view, helmet mounted display system of FIG. 32. An active matrix single crystal silicon display device 2010 is mounted in close proximity to the eye 2012. A lens 2014 is used to deliver a focussed image to the eye. Lens 2014 has a given thickness and a diameter d. Table 1 lists characteristics of commercially available lens including diameter, F# and center thickness. Other lenses having the desired dimensions are easily manufactured to provide the thickness and focal length necessary.

TABLE 1

| Diam. in. (mm) | Nom. f @ 589 nm (mm) | Nom. BFL @ 589 nm (mm) | F/# | Ctr. Thk. (mm) | Edge Thk. (mm) |
|---|---|---|---|---|---|
| 0.5 (12.7) | 11 | 9 | 0.8 | 5.7 | 1.34 |
| | 13.7 | 12.2 | 1.0 | 4.3 | 1.1 |
| | 16.6 | 15.4 | 1.3 | 3.6 | 1.1 |
| | 20.5 | 19.5 | 1.5 | 3.1 | 1.1 |
| | 26.4 | 25.6 | 2.0 | 2.6 | 1.1 |
| | 38.4 | 37.7 | 3.0 | 2.1 | 1.1 |
| | 51.3 | 50.7 | 4.0 | 2.0 | 1.2 |
| 1.0 (25.4) | 20 | 18 | 0.8 | 11.0 | 2.3 |
| | 27.4 | 24.6 | 1.0 | 8.2 | 1.8 |
| | 33 | 30.7 | 1.3 | 6.7 | 1.6 |
| | 39 | 37 | 1.5 | 5.8 | 1.6 |
| | 51.7 | 50.2 | 2.0 | 4.7 | 1.6 |
| | 63.6 | 62.3 | 2.5 | 4.0 | 1.6 |

TABLE 1-continued

| Diam. in. (mm) | Nom. f @ 589 nm (mm) | Nom. BFL @ 589 nm (mm) | F/# | Ctr. Thk. (mm) | Edge Thk. (mm) |
|---|---|---|---|---|---|
| | 76.6 | 75.2 | 3.0 | 4.0 | 1.9 |
| | 101.6 | 100.3 | 4.0 | 4.0 | 2.4 |
| 1.5 (38.1) | 34.4 | 29.4 | 0.85 | 14.0 | 1.9 |
| | 40 | 36 | 1.0 | 12.0 | 2.1 |
| | 52.5 | 49.4 | 1.3 | 9.1 | 2.0 |
| | 64.2 | 61.7 | 1.7 | 7.5 | 1.8 |
| | 77 | 74.8 | 2.0 | 6.5 | 1.8 |
| | 101.8 | 100 | 2.6 | 5.3 | 1.8 |
| | 127.2 | 125.6 | 3.3 | 5.0 | 2.2 |
| 2.0 (50.8) | 42 | 34.2 | 0.8 | 21.0 | 2.4 |
| | 53.6 | 48.4 | 1.0 | 15.0 | 2.0 |
| | 65 | 61 | 1.2 | 12.0 | 1.7 |
| | 77.8 | 74 | 1.5 | 11.0 | 2.6 |
| | 102 | 100 | 2.0 | 8.3 | 2.0 |
| | 127.6 | 125.3 | 2.5 | 7.0 | 2.0 |
| | 176.5 | 174.4 | 3.5 | 6.4 | 2.8 |

The distance from the center axis 2018 of lens 2014 to the display 2010 is denoted by P. The active matrix display has a high pixel density so as to match the resolution of the human eye. By increasing the resolution, or the density of pixels in the active matrix display 2010, and at the same time reduce the size of the display it is possible to position the display closer to the eye.

Where the distance P is less than 2.5 centimeters, the pixel density is at least 200 lines per centimeter and preferably over 400 lines per centimeter to provide the desired resolution.

Where P=1.5 centimeters, the display 10 is about 1.27 centimeters in diameter and has a pixel density of about 400 lines per centimeter. The focal length $F_L$ between the lens 2014 and focal point F is generally defined by the Expression:

$$\frac{1}{F_L} = \frac{1}{P} + \frac{1}{D_{IMAGE}}$$

Solving for the distance to the image we obtain $$D_{image} = \left(\frac{1}{F_L} - \frac{1}{P}\right)^{-1}$$

As the human eye will optimally focus an image at a distance of about 400 centimeters (about 15 feet), and as the focal length of the lens is preferably small enough to focus the image onto the eye over a short distance, the diameter of the lens should be less than 3 centimeters and preferably under 2.0 centimeters.

Table 2 defines the relationship between lens diameter d, and the distance between the lens and the display P in accordance with the invention where $D_{IMAGE}$ is about 400 centimeters:

TABLE 2

| Lens Diameter, d | Object Distance P (all in cm) |
|---|---|
| 0.6 | 0.48 |
| 0.8 | 0.64 |
| 1 | 0.80 |
| 1.2 | 0.96 |

TABLE 2-continued

| Lens Diameter, d | Object Distance P (all in cm) |
|---|---|
| 1.4 | 1.12 |
| 1.6 | 1.28 |
| 1.8 | 1.43 |
| 2 | 1.59 |
| 2.2 | 1.75 |
| 2.4 | 1.91 |
| 2.6 | 2.07 |
| 2.8 | 2.23 |
| 3 | 2.39 |

The above summarizes the preferred elements of a head mounted display where the active matrix display and lens system are mounted in close proximity to the eye. Note that the lens need not be circular in shape, however, but can be of a different shape to provide more peripheral information to the eye.

The following embodiment comprises a simple optical approach to attain a brightness increase of up to 100% by reducing a common parasitic loss. This loss obtains in all liquid crystal display light valves at the first polarizing filter, which attenuates one half of the unpolarized light emanating from the lamp. In other words, the light source of the display generates light of two polarizations; one polarization (half of the light) is absorbed by the polarizing filter to make it suitable for modulation by the liquid crystal.

Figure 33:
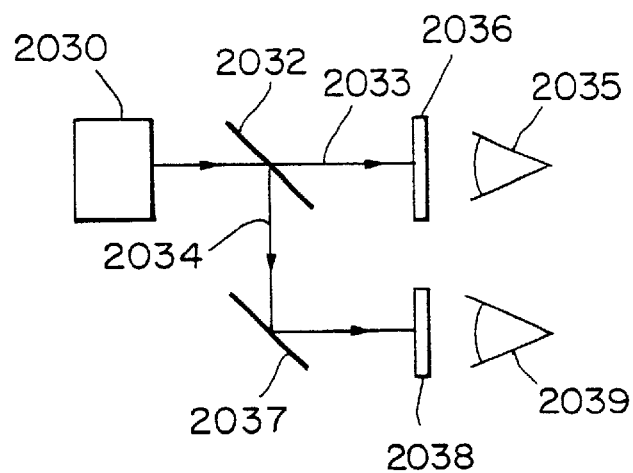
FIG. 33 illustrates a preferred embodiment of a head mounted display where two components of polarized light are separated for improved optical efficiency.

In this embodiment, as shown in FIG. 33, the light from source 30 is polarized, not by a polarizing filter, but by a Brewster polarizing window 2032 which passes one polarization 2033 only to light valve 2036. The other polarization 2034 is reflected, at window 2032 and reflected again at mirror 2037 and directed to a second light valve 2038. There are at least two implementations of this invention, as follows:

In a head-mounted display the Brewster window 2032 can be used to pass polarized light, TE polarized for example, to the right eye 2035 light valve liquid crystal display 2036. The reflected light, TM polarized in this example, is passed to the left eye 2039 light valve liquid crystal display 2038. Neither light valve requires a "first" polarizer, although the presence of one introduces only a slight reduction in fluence since the light is already polarized. Thus, substantially all of the incident light is passed to the liquid crystal, leading to near doubling of the optical efficiency. Of course, the liquid crystal in the left and right liquid crystal display must be rotated 90° with respect to each other to account for the polarization of the TE and TM polarizations of the light. The absence of a "first" polarizing filter can reduce the cost of the display.

Figure 34:
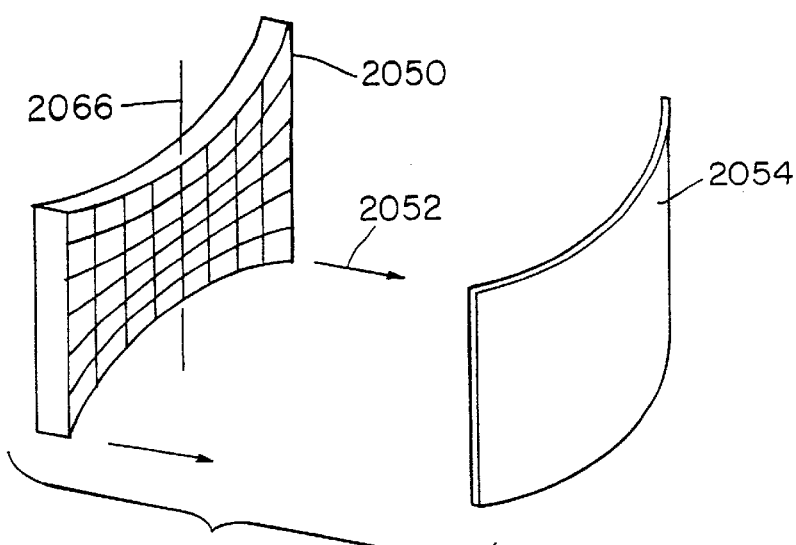
FIG. 34 illustrates an active matrix for a wide angle field of view head mounted display system.

Another preferred embodiment of the invention is illustrated in FIG. 34. In this embodiment the active matrix 2050 is fabricated where the pixel geometry and pixel area is variable as a function of the position of the pixel within the matrix. This provides a wide angle field of view image that can be projected onto the internal surface of the face shield 2054 of the head mounted display. This visual effect can also be done electronically by transforming the video input such that the intensity of appropriate pixels is adjusted to conform to the viewer's perception. The eye tracking system described previously can be used to adjust intensity depending upon the direction in which each eye is looking.

Figure 35:
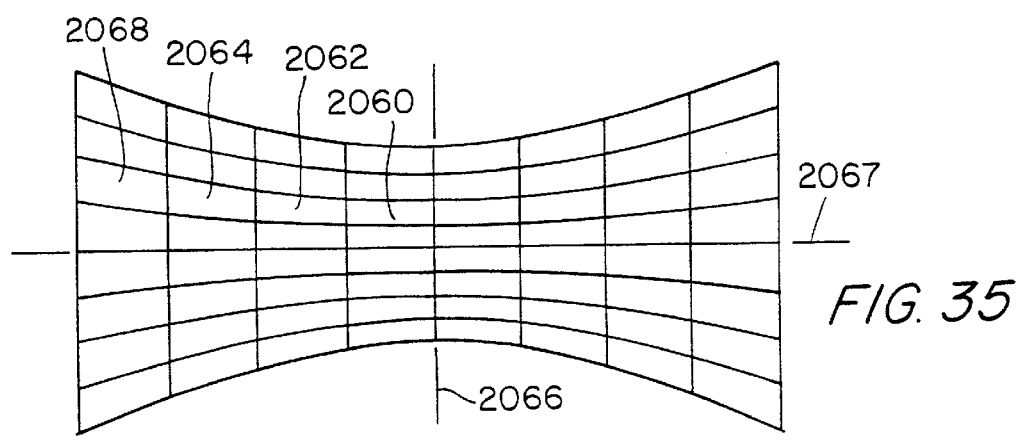
FIG. 35 provides a detailed view of a portion of the active matrix area of the device shown in FIG. 34.

FIG. 35 illustrates a detailed view of a portion of the active matrix surface area. Pixels 2060, 2062, 2064 and 2068 have an increasing surface area as the distance from the pixel to the matrix center 2066 axis is increased. The distance between adjacent column lines and between adjacent row lines also increases as a function of the distance from center axis 2066. The matrix can be a backlit transmission display or an emission type display. The active matrix can be formed on a first substrate and transferred onto either a flat or curved substrate prior to mounting onto the optical support assembly of the helmet. The active matrix can also be transferred to a flat substrate that is subjected to a low temperature anneal in the range of 300–400° F. and preferably at about 350° F. that will provide a desired curvature to the active matrix.

Figure 36:
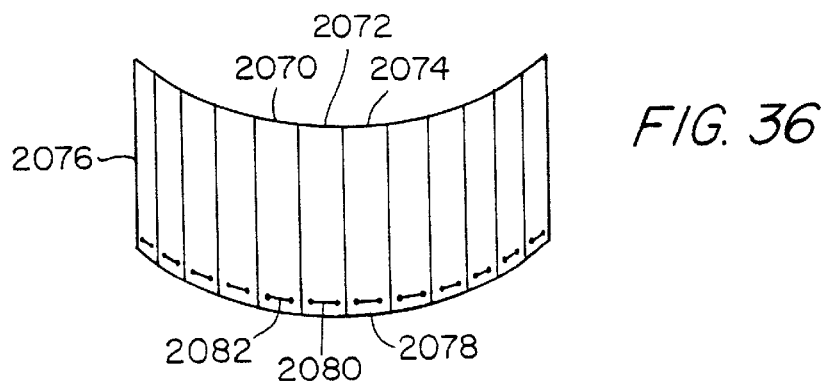
FIG. 36 illustrates an active matrix mounted or tiled onto a visor screen.

A further embodiment is illustrated in FIG. 36 wherein separate active matrix display elements 2070, 2072, 2074 etc. are mounted or tiled onto a plastic visor screen 2076. The visor screen can be polycarbonate, polyethylene or polyester material. Each display element 2070, 2072, 2074 can have driver circuitry 2082, 2080, 2078, respectively, formed separately on the edge.

Figure 37A:
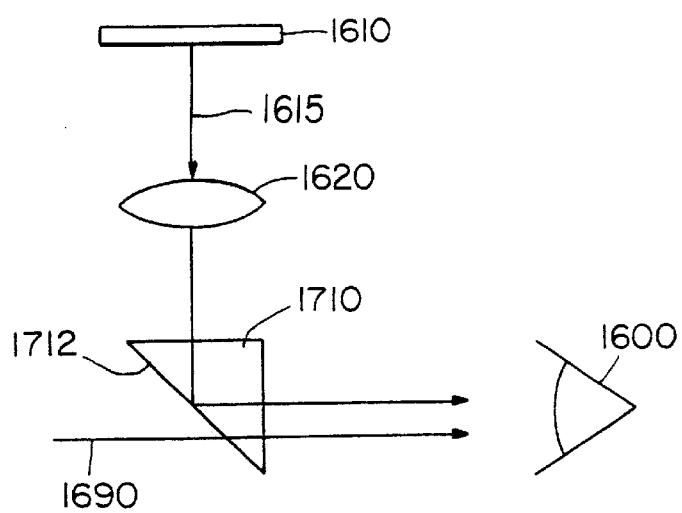
FIGS. 37A–37C illustrates other preferred embodiments of a direct-view display system.
Figure 37B:
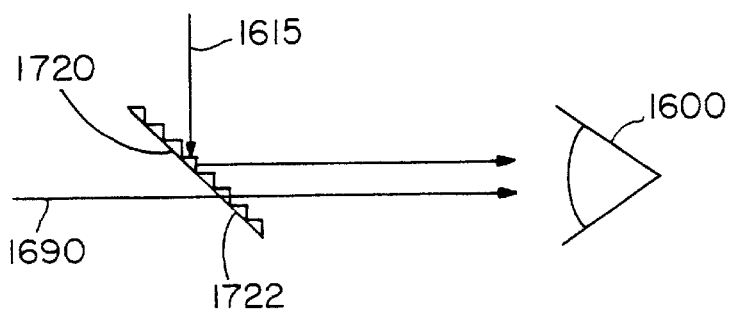
Figure 37C:
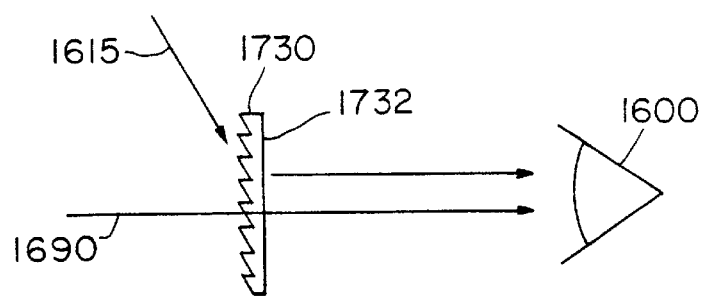

FIGS. 37A–37C illustrate other preferred embodiments of a direct-view display system. Light from a display device 1610 is represented by light ray 1615. The light ray 1615 from the display 1610 may pass through an optical system or lens 1620. The ray of light 1615 from the display 1610 is combined with ambient light 1690 before becoming incident on a viewer's eye 1600. Thus, the image created by the display device 1610 appears to the viewer to float in the viewer's field of vision.

There are various means of combining the display image 1615 with the ambient image 1690, which will now be described. FIG. 37A illustrates a preferred embodiment of the invention using a prism 1710 to combine the images. The hypotenuse of the prism may,be coated with a partial reflector or electrochromatic material 1712 to attenuate ambient light 1690. FIG. 37B illustrates a preferred embodiment of the invention using a lenticular structure 1720 as an image combiner. The gradings are spaced such that the eye 1600 cannot distinguish lines in the structure 1620. In a preferred embodiment, the grating density is greater than or equal to 150 per inch. FIG. 37C is similar to the lenticular structure in FIG. 37B except that a Fresnel lenticular structure 1730 is used. In both lenticular structures 1720, 1730, the flat surface 1722, 1732 may also be coated with a partial reflector or electrochromatic material. In either of FIGS. 37A–37C, the display system 1610 may be mounted adjacent to the viewer's head. In a preferred embodiment of the invention, the display device 1610 is mounted adjacent to the sides of the viewer's head, such as on the sides of a viewer. The head mounted systems described herein utilize audio circuitry and acoustic speakers to deliver sounds to the user's ears and can employ sensor systems such as cameras, magnetic position sensors, LED's or ultrasound for determining the position of the user's head. Additional sensors on a user's glove or other actuators can be electronically connected to a system data processor to provide interactive capabilities.

Equivalents

The preceding description is particular to the preferred embodiments and may be changed or modified without substantially changing the nature of the invention. For example, while the invention has been illustrated primarily by use of a passive substantially transparent LCD display, other type displays both active and passive are within the contemplation of the invention; such as, without limitation, the following: active displays, e.g., plasma display panels, electroluminescent displays, vacuum fluorescent displays and light emitting diode displays; passive displays: electrophoretic image displays, suspended particle displays, twisting ball displays or transparent ceramic displays. In each case, the eye tracking photodetector system can be formed in the same film as the display pixel or monolithically formed above or below the pixel to sense which pixel or group of pixels receive eye reflected light. While the invention has been particularly shown and described with reference to preferred embodiments thereof, it will be understood by those skilled in the art that various changes in form and details may be made therein without departing from the spirit and scope of the invention as defined by the appended claims.

What is claimed is:

1. A head mounted display system comprising:
   a support frame for positioning on a user's head;
   an active matrix display mounted on the support frame to direct an image emitted from a display surface onto any eye of the user and having a plurality of row address lines and a plurality of column address lines, the active matrix display further comprising an array of pixel circuits and an array of pixel electrodes, each pixel circuit being formed in a thin film of single crystal material and being electrically connected to one row address line and one column address line;
   a lens positioned near the active matrix display to focus an image from the display; and
   an array of photodetectors located adjacent the display for detecting light reflected from the eye of the viewer, the light emanating from the display pixels and reflected by the eye along an optical path.

2. The head mounted display system of claim 1 wherein the active matrix display further comprises at least 1000 row address lines.

3. The head mounted display system of claim 1 wherein the lens comprises a center axis and is positioned such that the lens center axis is 1.52 centimeters or less from the display surface.

4. The head mounted display system of claim 1 wherein the active matrix display is positioned to direct an image onto the user's left eye and further comprising a second active matrix display mounted on the support frame such that the second active matrix display directs light onto the user's right eye.

5. The head mounted display system of claim 1 further comprising a driver circuit in the thin film of single crystal silicon.

6. The head mounted display system of claim 1 wherein the active matrix display comprises a color display.

7. The head mounted display system of claim 1 wherein the display comprises an electroluminescent display.

8. The head mounted display system of claim 1 wherein the display comprises a liquid crystal display.

9. The head mounted display system of claim 1 wherein the active matrix is mounted on a curved substrate secured to the support frames.

10. The head mounted display system of claim 1 wherein the pixels comprise light emitting diodes.

11. The head mounted system of claim 1 further comprising a viewing screen for viewing an image such that the display projects the image on the viewing screen along the optical path.

12. The system of claim 11 wherein the array of photodetectors detect light reflected from an eye of a viewer to determine the direction in which the eye of the viewer is looking, the light emanating from the display and reflected by the eye along an optical path.

13. The system of claim 12 further comprising a computer-readable medium having instructions for determining the direction of the eye by identifying which detectors detect the reflected light.

14. The system of claim 13 further comprising a filter that filters frequencies other than a predetermined image frequency for viewing on the viewing screen, the image comprising a cursor and projected at the predetermined image frequency.

15. The system of claim 14 further comprising a polarizer that polarizes the projected light in one plane and polarizes the light from an external scene in an opposite plane.

16. The system of claim 12 wherein each photodetector is aligned with a respective pixel to convert light from the pixels reflected by the eye into a electrical signal indicative of line-of-sight position and to generate signal for revising the image in response to eye position determinations.

17. The system of claim 11 wherein the viewing screen comprises a visor through which a viewer can see an external scene and the image is superimposed upon the viewing screen.

18. The system of claim 17 further comprising a polarizer that polarizes the projected light in one plane and polarizes the light from the external scene in an opposite plane.

19. The system of claim 11 further comprising a filter that filters frequencies other than a predetermined image frequency for viewing on the viewing screen, the image comprising a cursor and projected at the predetermined image frequency.

20. The system of claim 1 in which the display is a panel display taken from the group comprising an electroluminescent, liquid crystal or dot matrix displays.

21. The system of claim 1 in which the display is a flat panel display formed of a back panel having an active matrix array of pixels formed of Si thin film transistors transferred onto the back panel, a front display panel having an array of diodes formed of III–V materials transferred onto the front panel, and liquid crystal material enclosed between the front and back panels.

22. A head mounted detector/display module system comprising:
   a support frame for positioning on a user's head; and
   a flat panel display mounted on the support frame, the display comprised of a front panel, a back panel, and a display array of pixels disposed between said panels with an array of photodetectors disposed on one of the panels, each photodetector being aligned with a respective pixel of the display array.

23. The module of claim 22 in which the photodetectors are formed of III–V materials.

24. The module of claim 22 wherein the photodetectors are formed on a thin film of III–V material and transferred to a carrier and then transferred onto one of the panels.

25. The module of claim 22 wherein the array of photodetectors are disposed on the front panel.

26. The module of claim 22 wherein the display is an AMLCD, or EL display.

27. The module of claim 22 further comprising a viewing screen having a curved visor through which the viewer can view an external scene and upon which the display image may be superimposed upon the external scene.

28. The module of claim 27 wherein a frequency rejection filter is formed on the external side of the screen and a narrow pass-band frequency filter for passing the frequencies rejected by the rejection filter is formed on the photodetector array.

29. The module of claim 27 wherein the light from the display signals is polarized in one plane and the light from the external scene is polarized in an opposite plane.

30. The module of claim 22 in which the photodetectors of the array are interconnected in a common parallel circuit.

* * * * *

UNITED STATES PATENT AND TRADEMARK OFFICE
CERTIFICATE OF CORRECTION

PATENT NO. : 6,636,185 B1 Page 1 of 1
DATED : October 21, 2003
INVENTOR(S) : Mark B. Spitzer, Ronald Gale and Jeffrey Jacobsen It is certified that error appears in the above-identified patent and that said Letters Patent is hereby corrected as shown below:

Column 31,
Line 24, delete "near" and insert -- between --.
Lines 24 and 25, after "display" insert -- and the user's eye --.

Column 32,
Line 37, delete "a support frame for positioning on a user's head; and
Lines 38-39, delete "mounted on the support frame, the display".

Signed and Sealed this

Sixth Day of June, 2006

JON W. DUDAS
*Director of the United States Patent and Trademark Office*